(12) United States Patent
Kumar et al.

(10) Patent No.: US 7,705,185 B2
(45) Date of Patent: Apr. 27, 2010

(54) ALKYLATED AND POLYMERIC MACROMOLECULAR ANTIOXIDANTS AND METHODS OF MAKING AND USING THE SAME

(75) Inventors: Rajesh Kumar, Dracut, MA (US); Ashok L. Cholli, Chelmsford, MA (US)

(73) Assignee: Polnox Corporation, Lowell, MA (US)

( * ) Notice: Subject to any disclaimer, the term of this patent is extended or adjusted under 35 U.S.C. 154(b) by 369 days.

(21) Appl. No.: 11/389,564

(22) Filed: Mar. 24, 2006

(65) Prior Publication Data

US 2006/0233741 A1    Oct. 19, 2006

Related U.S. Application Data

(60) Provisional application No. 60/665,638, filed on Mar. 25, 2005.

(51) Int. Cl.
C07C 209/00    (2006.01)
A61K 31/74    (2006.01)

(52) U.S. Cl. .................................. 564/414; 424/78.27

(58) Field of Classification Search ................. None
See application file for complete search history.

(56) References Cited

U.S. PATENT DOCUMENTS

| | | | |
|---|---|---|---|
| 3,294,836 A | 12/1966 | Peterson et al. | |
| 3,441,545 A | 4/1969 | Blatz et al. | |
| 3,459,704 A | 8/1969 | Peterson et al. | |
| 3,557,245 A | 1/1971 | Phillips et al. | |
| 3,632,785 A | 1/1972 | Bornstein | |
| 3,645,970 A | 2/1972 | Kleiner | |
| 3,649,667 A | 3/1972 | Song et al. | |
| 3,655,831 A | 4/1972 | Friedman | |
| 3,870,680 A | 3/1975 | Schurdak | |
| 3,907,939 A | 9/1975 | Robin, et al. | |
| 3,953,402 A | 4/1976 | Kline | |
| 3,965,039 A | 6/1976 | Chaplits et al. | |
| 3,983,091 A | 9/1976 | Gloth et al. | |
| 3,996,160 A | 12/1976 | Dale et al. | |
| 3,996,198 A | 12/1976 | Wang et al. | |
| 4,054,676 A | 10/1977 | Weinshenker et al. | |
| 4,094,857 A * | 6/1978 | Wolfe, Jr. .................. | 524/222 |
| 4,096,319 A | 6/1978 | Willette et al. | |
| 4,097,464 A | 6/1978 | Kline | |
| 4,098,829 A | 7/1978 | Weinshenker et al. | |
| 4,107,144 A | 8/1978 | Russell et al. | |
| 4,136,055 A | 1/1979 | Lyons | |
| 4,202,816 A | 5/1980 | Moser et al. | |
| 4,205,151 A | 5/1980 | Dale et al. | |
| 4,213,892 A | 7/1980 | Scott | |
| 4,219,453 A | 8/1980 | Sakurai et al. | |
| 4,267,358 A | 5/1981 | Hechenbleikner et al. | |
| 4,281,192 A | 7/1981 | Jacquet et al. | |
| 4,283,572 A | 8/1981 | Klicker | |
| 4,317,933 A | 3/1982 | Parker | |
| 4,341,879 A | 7/1982 | Sugio et al. | |
| 4,355,148 A | 10/1982 | Layer et al. | |
| 4,377,666 A | 3/1983 | Farrar | |
| 4,380,554 A | 4/1983 | Serres, Jr. | |
| 4,447,657 A | 5/1984 | Firth et al. | |
| 4,465,871 A | 8/1984 | Firth et al. | |
| 4,510,296 A | 4/1985 | Hergenrother | |
| 4,511,491 A | 4/1985 | Ishii et al. | |
| 4,690,995 A | 9/1987 | Keskey et al. | |
| 4,761,247 A | 8/1988 | Rei et al. | |
| 4,824,929 A | 4/1989 | Arimatsu et al. | |
| 4,849,503 A | 7/1989 | Cotter et al. | |
| 4,855,345 A | 8/1989 | Rosenberger et al. | |
| 4,857,596 A | 8/1989 | MacLeay et al. | |
| 4,870,214 A | 9/1989 | Mina et al. | |
| 4,894,263 A | 1/1990 | Dubois et al. | |
| 4,897,438 A | 1/1990 | Kikuchi et al. | |
| 4,900,671 A | 2/1990 | Pokora et al. | |
| 4,925,591 A * | 5/1990 | Nakauchi et al. ....... | 252/299.66 |
| 4,968,759 A | 11/1990 | Kikuchi et al. | |
| 4,977,004 A | 12/1990 | Bettle, III et al. | |
| 4,981,917 A | 1/1991 | MacLeay et al. | |
| 4,994,628 A | 2/1991 | Goddard et al. | |
| 5,013,470 A | 5/1991 | Benfaremo | |
| 5,017,727 A | 5/1991 | Olivier | |

(Continued)

FOREIGN PATENT DOCUMENTS

CS    111291    6/1964

(Continued)

OTHER PUBLICATIONS

Spano et al, Substituted Anilides of 3-Monoethyl Ester of 4-Hydroxyisophthalic Acid, Journal of Medicinal Chemistry, 1972, 15(5), 5, 552-553.*

(Continued)

*Primary Examiner*—Michael G Hartley
*Assistant Examiner*—Paul Dickinson
(74) *Attorney, Agent, or Firm*—Hamilton, Brook, Smith & Reynolds, P.C.

(57) ABSTRACT

Alkylated antioxidant macromolecules are represented by Structural Formula 1:

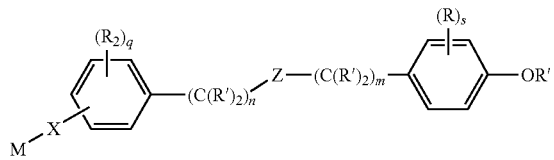

wherein the variables are described herein. Also included are methods of making the molecules and methods of using the molecules as antioxidants.

4 Claims, 9 Drawing Sheets

U.S. PATENT DOCUMENTS

| | | | |
|---|---|---|---|
| 5,082,358 A | 1/1992 | Tabata et al. |
| 5,102,962 A | 4/1992 | Kikuchi et al. |
| 5,117,063 A | 5/1992 | Stern et al. |
| 5,143,828 A | 9/1992 | Akkara et al. |
| 5,185,391 A | 2/1993 | Stokich, Jr. |
| 5,185,407 A | 2/1993 | Wong |
| 5,188,953 A | 2/1993 | Johnson et al. |
| 5,191,008 A | 3/1993 | Frost et al. |
| 5,196,142 A | 3/1993 | Mollet et al. |
| 5,206,303 A | 4/1993 | Tse et al. |
| 5,207,939 A | 5/1993 | Farng et al. |
| 5,274,060 A | 12/1993 | Schadeli |
| 5,278,055 A | 1/1994 | Cyrus, Jr. et al. |
| 5,304,589 A | 4/1994 | Davidson et al. |
| 5,320,889 A | 6/1994 | Bettle, III |
| 5,449,715 A | 9/1995 | Plochocka et al. |
| 5,498,809 A | 3/1996 | Emert et al. |
| RE35,247 E | 5/1996 | Cyrus, Jr. et al. |
| 5,516,856 A | 5/1996 | Sanchez |
| 5,541,091 A | 7/1996 | Wheeler et al. |
| 5,565,300 A | 10/1996 | Uenishi et al. |
| 5,574,118 A | 11/1996 | Olivier |
| 5,652,201 A | 7/1997 | Papay et al. |
| 5,739,341 A | 4/1998 | Dubs et al. |
| 5,834,544 A | 11/1998 | Lin et al. |
| 5,837,798 A | 11/1998 | Hutchings et al. |
| 5,869,592 A | 2/1999 | Gagne et al. |
| 5,911,937 A | 6/1999 | Hekal |
| 5,994,498 A | 11/1999 | Tripathy et al. |
| 6,018,018 A | 1/2000 | Samuelson et al. |
| 6,046,263 A | 4/2000 | Rasberger et al. |
| 6,096,695 A | 8/2000 | Lam et al. |
| 6,096,859 A | 8/2000 | Akkara et al. |
| 6,150,491 A | 11/2000 | Akkara |
| 6,232,314 B1 | 5/2001 | Jarrott et al. |
| 6,342,549 B1 | 1/2002 | Hirose et al. |
| 6,444,450 B2 | 9/2002 | Akkara et al. |
| 6,646,035 B2 | 11/2003 | Koch et al. |
| 6,723,815 B2 | 4/2004 | Callaghan et al. |
| 6,743,525 B2 | 6/2004 | Berntsen et al. |
| 6,770,785 B1 | 8/2004 | Desai et al. |
| 6,794,480 B2 | 9/2004 | Goto et al. |
| 6,800,228 B1 | 10/2004 | Semen |
| 6,828,364 B2 | 12/2004 | Gugumus |
| 7,132,496 B2 | 11/2006 | Kerres et al. |
| 7,169,844 B2 | 1/2007 | Inokami |
| 7,205,350 B2 | 4/2007 | Thibaut |
| 7,223,432 B2 | 5/2007 | Cholli et al. |
| 7,262,319 B2 | 8/2007 | Rehm et al. |
| 2001/0041203 A1 | 11/2001 | Uno et al. |
| 2002/0007020 A1 | 1/2002 | Higashimura et al. |
| 2002/0128493 A1 | 9/2002 | Romanczyk, Jr. et al. |
| 2002/0143025 A1 | 10/2002 | Pratt et al. |
| 2002/0183470 A1 | 12/2002 | Tripathy et al. |
| 2003/0030033 A1 | 2/2003 | Duyck et al. |
| 2003/0078346 A1 | 4/2003 | Nakamura et al. |
| 2003/0091837 A1 | 5/2003 | Aoki |
| 2003/0176620 A1 | 9/2003 | Romanczyk, Jr. et al. |
| 2003/0191242 A1 | 10/2003 | Zedda et al. |
| 2003/0229196 A1 | 12/2003 | Braat et al. |
| 2003/0230743 A1 | 12/2003 | Cholli et al. |
| 2004/0015021 A1 | 1/2004 | Adams et al. |
| 2004/0164279 A1 | 8/2004 | Stevenson et al. |
| 2004/0180994 A1 | 9/2004 | Pearson et al. |
| 2004/0186167 A1 | 9/2004 | Dou et al. |
| 2004/0186214 A1 | 9/2004 | Li et al. |
| 2004/0198875 A1 | 10/2004 | Kaprinidis et al. |
| 2004/0214935 A1 | 10/2004 | Cholli et al. |
| 2005/0170978 A1 | 8/2005 | Migdal et al. |
| 2005/0209379 A1 | 9/2005 | Botkin et al. |
| 2005/0238789 A1 | 10/2005 | Cholli et al. |
| 2005/0242328 A1 | 11/2005 | Baranski |
| 2006/0029706 A1 | 2/2006 | Cholli et al. |
| 2006/0040833 A1 | 2/2006 | Al-Akhdar et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1 | 6/2006 | Kumar et al. |
| 2006/0128939 A1 | 6/2006 | Kumar et al. |
| 2006/0154818 A1 | 7/2006 | Destro et al. |
| 2006/0189820 A1 | 8/2006 | Rehm et al. |
| 2006/0189824 A1 | 8/2006 | Kumar et al. |
| 2006/0208227 A1 | 9/2006 | Shiraki |
| 2007/0010632 A1 | 1/2007 | Kaplan et al. |
| 2007/0106059 A1 | 5/2007 | Cholli et al. |
| 2007/0135539 A1 | 6/2007 | Cholli et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |
| 2008/0249335 A1 | 10/2008 | Cholli et al. |
| 2008/0293856 A1 | 11/2008 | Kumar et al. |
| 2008/0311065 A1 | 12/2008 | Cholli |
| 2009/0184294 A1 | 7/2009 | Cholli et al. |

FOREIGN PATENT DOCUMENTS

| | | | |
|---|---|---|---|
| DE | 197 47 644 A1 | 5/1999 |
| DE | 198 43 875 A1 | 3/2000 |
| EP | 0 181 023 A1 | 5/1986 |
| EP | 0 289 077 A2 | 11/1988 |
| EP | 0 358 157 A1 | 3/1990 |
| EP | 0 404 039 A1 | 12/1990 |
| EP | 0 618 203 A1 | 10/1994 |
| EP | 0 688 805 A1 | 12/1995 |
| EP | 1 067 144 A1 | 1/2001 |
| EP | 1 468 968 A1 | 10/2004 |
| FR | 2 183 973 | 12/1973 |
| GB | 1 283 103 | 7/1972 |
| GB | 1 320 169 | 6/1973 |
| GB | 1 372 042 | 10/1974 |
| GB | 1 389 442 | 4/1975 |
| GB | 1 469 245 | 4/1977 |
| GB | 1 482 649 | 8/1977 |
| JP | 69002715 B | 1/1966 |
| JP | 43016392 B4 | 7/1968 |
| JP | 44024274 | 10/1969 |
| JP | 44028850 | 11/1969 |
| JP | 45 2980 | 1/1970 |
| JP | 49 29339 | 3/1974 |
| JP | 57085366 A | 5/1982 |
| JP | 59025814 | 2/1984 |
| JP | 59197447 | 11/1984 |
| JP | 60-199832 | 10/1985 |
| JP | 05 199858 | 8/1993 |
| JP | 06135876 A * | 5/1994 |
| JP | 06 247959 | 9/1994 |
| JP | 08027226 A | 1/1996 |
| JP | 09262069 | 10/1997 |
| JP | 09 328519 | 12/1997 |
| JP | 09 328521 | 12/1997 |
| JP | 9322784 A | 12/1997 |
| JP | 11-80063 | 3/1999 |
| JP | 11-158103 | 6/1999 |
| JP | 2003138258 | 5/2003 |
| NL | 7 905 000 | 3/1980 |
| WO | WO 92/20734 | 11/1992 |
| WO | WO 00/39064 A1 | 7/2000 |
| WO | WO 01/18125 A1 | 3/2001 |
| WO | WO 01/48057 A1 | 7/2001 |
| WO | WO 02/079130 A1 | 10/2002 |
| WO | WO 03/087260 A1 | 10/2003 |

| WO | WO 03/102004 A1 | 12/2003 |
| --- | --- | --- |
| WO | WO 2004/024070 A2 | 3/2004 |
| WO | WO 2004/050795 A2 | 6/2004 |
| WO | WO 2005/025513 A2 | 3/2005 |
| WO | WO 2005/025646 A2 | 3/2005 |
| WO | WO 2005/060500 A2 | 7/2005 |
| WO | WO 2005/070974 A2 | 8/2005 |
| WO | WO 2005/071005 A1 | 8/2005 |
| WO | WO 2006/018403 A1 | 2/2006 |
| WO | WO 2006/060801 A2 | 6/2006 |
| WO | WO 2006/104957 A2 | 10/2006 |
| WO | WO 2008/005358 | 1/2008 |

OTHER PUBLICATIONS

Machine translation of JP 06135876 A.*
Hatayama et al, Anti-ulcer Effect of Isoprenyl Flavonoids. III. Synthesis and Anti-ulcer Activity of Metabolites of 2'-Carboxymethoxy-4,4'-bis(3-methyl-2-butyenyloxy)chalcone, Chemical & Pharmaceutical Bulletin, 1985, 33(4), 1327-1333.*
Dordick, J.S., et al., "Polymerization of Phenols Catalyzed by Peroxidase in Nonaqueous Media," *Biotechnology and Bioengineering*, XXX:31-36 (1987).
Kazandjian, R.Z., et al., "Enzymatic Analyses in Organic Solvents," *Biotechnology and Bioengineering*, XXVIII:417-421 (1986).
Klibanov, A.M., et al., "Enzymatic Removal of Toxic Phenols and Anilines from Waste Waters," *J. of Applied Biochemistry*, 2(5):414-421 (1980).
Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).
Akkara, J.A., et al., "Synthesis and Characterization of Polymers Produced by Horseradish Peroxidase in Dioxane," *J. of Polymer Science: Part A: Polymer Chemistry*, 29(11):1561-1574 (1991).
Ayyagari, M.S., et al., "Controlled Free-Radical Polymerization of Phenol Derivatives by Enzyme-Catalyzed Reactions in Organic Solvents," *Macromolecules*, 28(15):5192-5197 (1995).
Ryu, K., et al., "Peroxidase-Catalyzed Polymerization of Phenols," Biocatalysis in Agricultural Biotechnology, Chapter10:141-157 (1988).
Bruno, F.F., et al., "Enzymatic Template Synthesis of Polyphenol," Materials Research Society Symposium Proceedings vol. 600, Electroactive Polymers (EAP):255-259 (1999).
Akkara, J.A., et al., "Hematin-Catalyzed Polymerization of Phenol Compounds," Macromolecules, 33(7):2377-2382 (2000).
Dordick, J.S., "Enzymatic Catalysis in Monophasic Organic Dolvents," *Enzyme Microb. Technol.*, 11(4):194-211 (1989).
FS&T 821 "Food Lipids," [online], Oct. 2001 [retrieved on Oct. 29, 2002]. Retrieved from the Internet <URL: http://class.fst.ohio-state.edu/fst821/>.
FST 821 "Course Schedule," [online], [retrieved on Oct. 29, 2002]. Retrieved from the Internet <URL: http://class.fst.ohio-state.edu/fst821/>.
FS&T 821 "Antioxidant," [online], [retrieved on Oct. 29, 2002]. Retrieved from the Internet <URL: http://class.fst.ohio-state.edu/fst821/>.
Jialanella, G.and Pilrma, I., "Synthesis of Poly(vinyl alcohol-co-vinyl gallate) by the Chemical Modification of Poly(vinyl alcohol)," Polymer Bulletin 18:385-389 (1987).
Jayaprakasha, G.K., et al., "Antioxidant Activity of Grape Seed (*Vitis vinifera*) Extracts on Peroxidation Models In Vitro," *Food Chemistry*, 73:285-290 (2001).
Hidalgo, M.E., et al., "Antioxidant Activity of Depsides and Depsidones," Phytochemistry, 37(6):1585-1587 (1994).
Khan, K.M., et al., "An Expedient Esterification of Aromatic Carboxylic Acids Using Sodium Bromate and Sodium Hydrogen Sulfite," *Tetrahedron* 59(29):5549-5554 (2003).
March, J., Advanced Organic Chemistry, McGraw Hill Book Company, New York, pp. 251-259 (1977).
Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.
Database Beilstein [online] Beilstein Institut Zur Förderung Der Chemischen Wissenschaften; XP002420027, Beilstein Registry No. 3517906.
Database Beilstein [online] Beilstein Institut Zur Förderung Der Chemischen Wissenschaften; XP002420028, Beilstein Registry No. 5840042.
Database Beilstein [online] Beilstein Institut Zur Förderung Der Chemischen Wissenschaften; XP002420029, Beilstein Registry No. 2311871.
Database Beilstein [online] Beilstein Institut Zur Förderung Der Chemischen Wissenschaften; XP002420030, Beilstein Registry No. 8876646.
Database Beilstein [online] Beilstein Institut Zur Förderung Der Chemischen Wissenschaften; XP002420031, Beilstein Registry No. 2271400.
Database Beilstein [online] Beilstein Institut Zur Förderung Der Chemischen Wissenschaften; XP002420032, Beilstein Registry No. 2212095.
Database Beilstein [online] Beilstein Institut Zur Förderung Der Chemischen Wissenschaften; XP002420033, Beilstein Registry No. 8941955.
Database Beilstein [online] Beilstein Institut Zur Förderung Der Chemischen Wissenschaften; XP002420034, Database Accession No. 2312425.
Database Beilstein [online] Beilstein Institut Zur Förderung Der Chemischen Wissenschaften; XP002420035, Beilstein Registry No. 905950.
Database Beilstein [online] Beilstein Institut Zur Förderung Der Chemischen Wissenschaften; XP002420036, Beilstein Registry No. 2140308.
Database Beilstein [online] Beilstein Institut Zur Förderung Der Chemischen Wissenschaften; XP002420037, Beilstein Registry No. 134886.
Database Beilstein [online] Beilstein Institut Zur Förderung Der Chemischen Wissenschaften; XP002420038, Beilstein Registry No. 1961007.
Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.
Masada, H. and Oishi, Y., "A New Synthesis of aryl *t*-butyl Ethers," *Chem. Letters*, 57-58 (1978).
Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).
Masada, H., et al., "A New Method for the Williamson Ether Synthesis Using *t*-alkyl Halides in Nonpolar Solvents," *The Chemical Society of Japan*, 2:164-166 (1995).
Masada, H. et al., "A New Heterogeneous Williamson Synthesis of Ethers Using *t*-alkyl Substrates," *The Chemical Society of Japan* 3:275-282 (1996).
Tsvetkov, O.N., et al., "Alkylation of Phenols with Higher Olefins. Part I," *Int Chem. Eng.* 7(1):104-121 (1967).
Sartori G., et al., "Highly Selective Mono-*tert*-butylation of Aromatic Compounds," *Chem. Ind.*, (London), (22):762-763 (1985).
Koshchii, V.A., et al. "Alkylation of Phenol by Alcohols in the Presence of Alumium Phenolate," *Org. Chem.* 24(7):1358-1361 (1988).
Chandra, K.G. and Sharma, M.M., "Alkylation of Phenol with MTBE and Other tert-butylethers:Cation Exchange Resins as Catalysts," *Catal. Lett.* 19(4):309-317 (1993).
Sakthivel, A., et al., "Vapour Phase Tertiary Butylation of Phenol Over Sulfated Zirconia Catalyst," *Catal. Lett.*, 72(3-4):225-228 (2001).
Quaschning, V., et al., "Properties of Modified Zirconia Used as Friedel-Crafts-Acylation Catalysts," *J. Catal.* 177:164-174 (1998).
Badamali, S.K., et al., "Influence of Aluminium Sources on the Synthesis and Catalytic Activity of Mesoporous AlMCM-41 Molecular Sieves," *Catal. Today* 63:291-295 (2000).
Heidekum, A., et al., "Nafion/Silica Composite Material Reveals High Catalytic Potential in Acylation Reactions," *J. Catal.* 188:230-232 (1999).

Kamitori, Y., et al., "Silica Gel as an Effective Catalyst for the Alkylation of Phenols and Some Heterocylic Aromatic Compounds," *J. Org. Chem.* 49: 4161-4165 (1984).

Armengol, E., et al., "Acid Zeolites as Catalysts in Organic Reactions, *tert*-Butylation of Anthracene, Naphthalene and Thianthrene," *Appl. Catal. A* 149:411-423 (1997).

Lalancette, J.M., et al. "Metals Intercalated in Graphite. II. The Friedel-Crafts Reactions with $ALCL_3$-Graphite," *Can. J. Chem.* 52:589-591 (1974).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Devassy, B.M., et al., "Zirconia Supported Phosphotungstic Acid as an Efficient Catalyst for Resorcinol *tert*-Butylation and *n*-Heptane Hydroisomerization," *J. Mol. Catalysis A: Chemical* 221:113-119(2004).

XP-002419239, "Discover Our World of Effects for Polyolefins," *Ciba Speciality Chemicals*, (2003).

Pirozhenko, V.V., et al., "NMR Study of Topomerization of *N*-Aroyl-*p*-Benzoquinonemonoimines," *Russian J. of Organic Chem.*, 31(11):1514-1519 (1995).

Coppinger, G.B., et al., "Photo-Fries Rearrangement of Aromatic Esters. Role of Steric and Electronic Factors" *J. of Phy. Chem.*, 70(11):3479-3489 (1966).

Spano, R., et al., "Substituted Anilides of 3-Monoethyl Ester of 4 Hydroxyisophthalic Acid," *J. of Med. Chem.*, 15(5):552-553 (1972).

Mejias, L., et al. "New Polymers From Natural Phenols Using Horseradish or Soybean Peroxidase," *Macromol. Biosci.*, 2:24-32 (2002).

Ismail, M.N. and Wazzan, A.A., "Evaluation of New Thermal Stabilizers and Antifatigue Agents for Rubber Vulcanizates," *Polymer-Plastics Tech. and Eng.*, 45:751-758 (2006).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Belyaev, A., et al., "Structure-Activity Relationship of Diaryl Phosphonate Esters as Potent Irreversible Dipeptidyl Peptidase IV Inhibitors," *J. Med Chem.*, 42:1041-1052 (1999).

Blokhin, Y.I, et al., "Phosphorylation of Dihydric Phenols with Amides of Phosphorous Acid," *Russian Chem. Bulletin*, 45(9):2250-2251 (1996).

Pätoprstý, V., et al., "$^{13}C$ NMR Study of 3,9-Di(alkylphenoxy)-2,4,8,10-tetraoxa-3,9-diphosphaspiro[5.5]undecanes," *Magnetic Resonance in Chem*, 23(2):122-126 (1985).

Singh, A. and Kaplan, D. L., "Biocatalytic Route to Ascorbic Acid-Modified Polymers for Free-Radical Scavenging," *Adv. Matter.*, 15(15):1291-1294 (2003).

Kim, T. H., et al., "Melt Free-Radical Grafting of Hindered Phenol Antioxidant onto Polyethylene," *J. Applied Polymer Science*, 77:2968-2973 (2000).

Faber, K., "Biotransformations in Organic Chemistry," A Textbook, Fourth Completely Revised and Extended Edition, Springer-Verlag pp. 347-349 (1953).

English Abstract of Kovalev, G. I., et al., "Study of the Effectiveness of Inhibitors in Oxidation of Jet Fuel in a Closed Volume, "*Deposited Doc.*, Viniti: 443-82 (1981).

English Abstract of Kovalev, G.I., et al., "Effectiveness of Inhibitors in the Oxidation of Jet Fuel With an Initiator," *J. Neftekhimiya (Petroleum Chemistry)*, 21(2): 287-298 (1981).

Thompson, C.R., et al., "Stability of Carotene in Alfalfa Meal: Effect of Antioxidants," *Industrial and Engineering Chemistry*, Western Regional Research Laboratory, Albany, Calif., 42(5); 922-925 (May 1950).

Scharpe, S.L., et al., "Serine Peptidase Modulators, Their Preparation, and Their Therapeutic Use," Chemical Abstracts Service, ZCAPLUS, document No. 131:223514 (1999).

Maki, M., et al., "Weather-Resistant Colored Polypropylene," Chemical Abstracts Service, ZCAPLUS, document No. 89:111364 (1978).

Hofer, K., et al., "[[(Anilinooxalyl)amino]phenyl] Phosphite Stabilizers for Polypropylene," Chemical Abstracts Service, ZCAPLUS, document No. 77:62780 (1972).

Ding, et al., "Chemical Trapping Experiments Support a Cation-Radical Mechanism for the Oxidative Polymerization of Aniline," *Journal of Polymer Science: Part A: Polymer Chemistry*, 37:2569-2579 (1999).

Ciric-Marjanovic, et al., "Chemical Oxidative Polymerization of Aminodiphenylamines," *Journal of Physical Chemistry B*, 112(23): 6976-6987 (2008).

Li, et al., "Novel Multifunctional Polymers," Chemical Reviews, 102(9): 2925-2943 (2002).

Translation of Nakatsuka et al. (JP 45-2980), Schreiber Translation, Inc., Jul. 2009.

* cited by examiner

ALKYLATED AND POLYMERIC MACROMOLECULAR ANTIOXIDANTS AND METHODS OF MAKING AND USING THE SAME

RELATED APPLICATIONS

This application claims the benefit of U.S. Provisional Application No. 60/665,638, filed on Mar. 25, 2005. The entire teachings of the above application are incorporated herein by reference.

BACKGROUND OF THE INVENTION

Antioxidants are employed to prevent oxidation in a wide range of materials, for example, plastics, elastomers, lubricants, petroleum based products (lubricants, gasoline, aviation fuels, and engine oils), cooking oil, cosmetics, processed food products, and the like. While many antioxidants exist, there is a continuing need for new antioxidants that have improved properties.

SUMMARY OF THE INVENTION

The present invention relates to alkylated and polymeric antioxidant macromolecules that in general have improved antioxidant properties.

In one embodiment the present invention is directed to compounds represented Structural Formula 1:

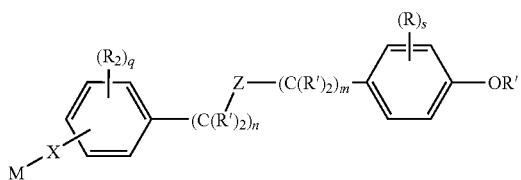

Z is —C(O)NR'—, —NR'C(O)—, —NR'—, —CR'=N—, —C(O)—, —C(O)O—, —OC(O)—, —O—, —S—, —C(O)OC(O)— or a bond. Each R' is independently —H or optionally substituted alkyl. Each R is independently an optionally substituted alkyl, optionally substituted aryl, optionally substituted alkoxycarbonyl, optionally substituted ester, —OH, —NH$_2$, —SH, or

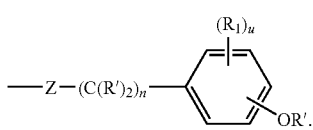

Each R$_1$ is independently an optionally substituted alkyl, optionally substituted aryl, optionally substituted alkoxycarbonyl, optionally substituted ester, —OH, —NH$_2$ or —SH. Each R$_2$ is independently an optionally substituted alkyl, optionally substituted aryl, optionally substituted alkoxycarbonyl, optionally substituted ester, —OH, —NH$_2$ or —SH. X is —C(O)O—, —OC(O)—, —C(O)NR'—, —NR'C(O)—, —NR'—, —CH=N—, —C(O)—, —O—, —S—, —NR'— or —C(O)OC(O)—. M is an alkyl or

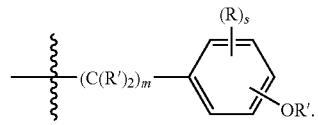

Each n and m are independently integers from 0 to 6. Each s, q and u are independently integers from 0 to 4. In certain embodiments M is not

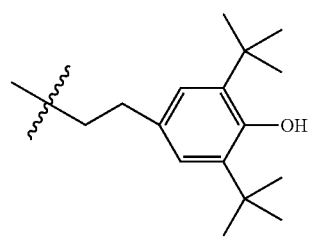

when X is —C(O)O— or —OC(O)—.

In another embodiment, the present invention is directed to polymers represented by Structural Formula 2:

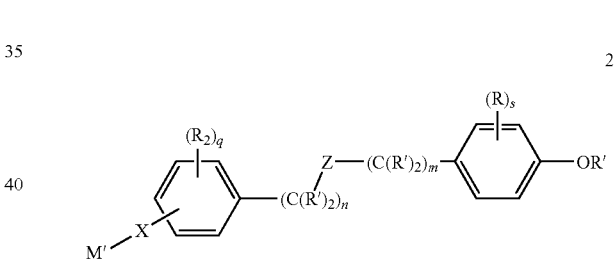

Z is —C(O)NR'—, —NR'C(O)—, —NR'—, —CR'=N—, —C(O)—, —C(O)O—, —OC(O)—, —O—, —S—, —C(O)OC(O)— or a bond. Each R' is independently —H or optionally substituted alkyl. Each R is independently an optionally substituted alkyl, optionally substituted aryl, optionally substituted alkoxycarbonyl, optionally substituted ester, —OH, —NH$_2$, —SH, or

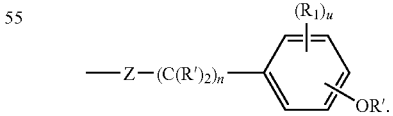

Each R$_1$ is independently an optionally substituted alkyl, optionally substituted aryl, optionally substituted alkoxycarbonyl, optionally substituted ester, —OH, —NH$_2$ or —SH. Each R$_2$ is independently an optionally substituted alkyl, optionally substituted aryl, optionally substituted alkoxycarbonyl, optionally substituted ester, —OH, —NH$_2$ or —SH or

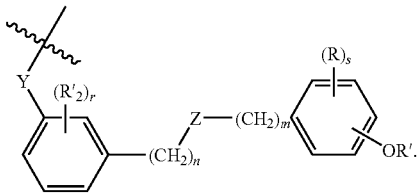

Each R'$_2$ is independently —M'—X, an optionally substituted alkyl, optionally substituted aryl, optionally substituted alkoxycarbonyl, optionally substituted ester, —OH, —NH$_2$, —SH or

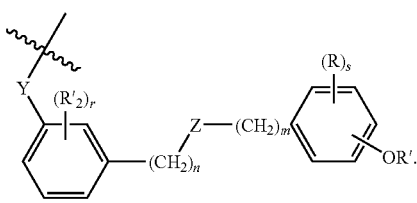

X is —C(O)O—, —OC(O)—, —C(O)NR'—, —NR'C(O)—, —NR'—, —CR'═N—, —C(O)—, —O—, —S—, —NR'— or —C(O)OC(O)—. Each Y is independently Q—W—Q'. Each Q is independently an optionally substituted C1-C20 alkylene group. Each Q' is independently a bond or an optionally substituted C1-C20 alkylene group. Each W is independently arylene, —O—, —S—, —NR'—, —N(OR')—, —C(═N(OR'))—, —C(O)NR'—, —NR'C(O)—, —CR'═N—, —C(O)—, —C(O)O—, —OC(O)—, —C(O)OC(O)—, or a bond. Each M' is independently —H, alkyl, or

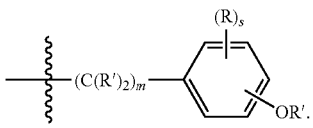

Each n and m are independently integers from 0 to 6. Each s, q and u are independently integers from 0 to 4. r is an integer from 0 to 4.

In another embodiment, the present invention is directed to compositions comprising a compound represented by Structural Formula 1 (as defined herein) and a compound represented by Structural Formula 3:

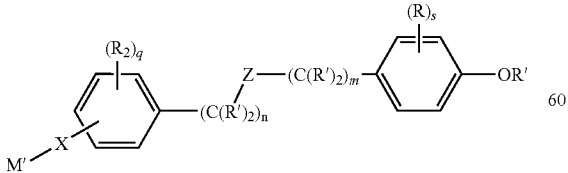

Z is —C(O)NR'—, —NR'C(O)—, —NR'—, —CR'═N—, —C(O)—, —C(O)O—, —OC(O)—, —O—, —S—, —C(O)OC(O)— or a bond. Each R' is independently —H or optionally substituted alkyl. Each R is independently an optionally substituted alkyl, optionally substituted aryl, optionally substituted alkoxycarbonyl, optionally substituted ester, —OH, —NH$_2$, —SH, or

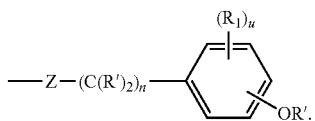

Each R$_1$ is independently an optionally substituted alkyl, optionally substituted aryl, optionally substituted alkoxycarbonyl, optionally substituted ester, —OH, —NH$_2$ or —SH. Each R$_2$ is independently an optionally substituted alkyl, optionally substituted aryl, optionally substituted alkoxycarbonyl, optionally substituted ester, —OH, —NH$_2$ or —SH. X is —C(O)O—, —OC(O)—, —C(O)NR'—, —NR'C(O)—, —NR'—, —CH═N—, —C(O)—, —O—, —S—, —NR'— or —C(O)OC(O)—. M' is a —H, alkyl or

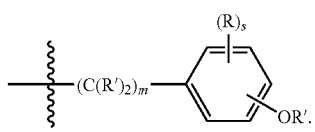

Each n and m are independently integers from 0 to 6. Each s, q and u are independently integers from 0 to 4.

In another embodiment the present invention is directed to methods of inhibiting oxidation in an oxidizable material comprising combining the oxidizable material with a compound represented Structural Formula 1.

In another embodiment the present invention is directed to methods of inhibiting oxidation in an oxidizable material comprising combining the oxidizable material with a polymer represented Structural Formula 2.

In another embodiment the present invention is directed to methods of inhibiting oxidation in an oxidizable material comprising combining the oxidizable material with a composition comprising a compound represented Structural Formula 1 and a compound represented Structural Formula 3.

In another embodiment the present invention is a method of making a compound represented by Structural Formula 1, comprising the steps of alkylating a compound represented by the following structural formula:

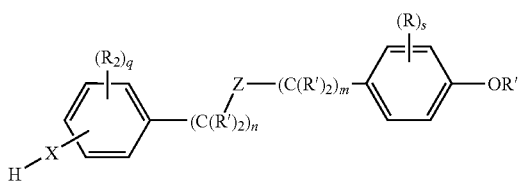

where the variables are described herein, with a haloalkyl and isolating the alkylated compound.

In another embodiment the present invention is a method of making a polymer represented by the following Structural Formula 3, comprising the steps of polymerizing a compound represented by the following structural formula:

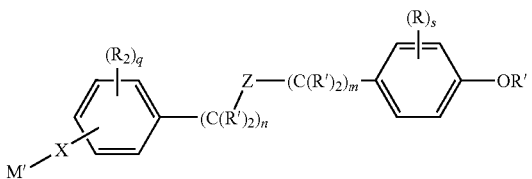

where the variables are described herein, in the presence of an aldehyde and isolating the polymer.

In certain embodiments, the alkylated antioxidant macromolecules of the present invention can have enhanced antioxidant activity and better thermal stability compared to commercially available antioxidants.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
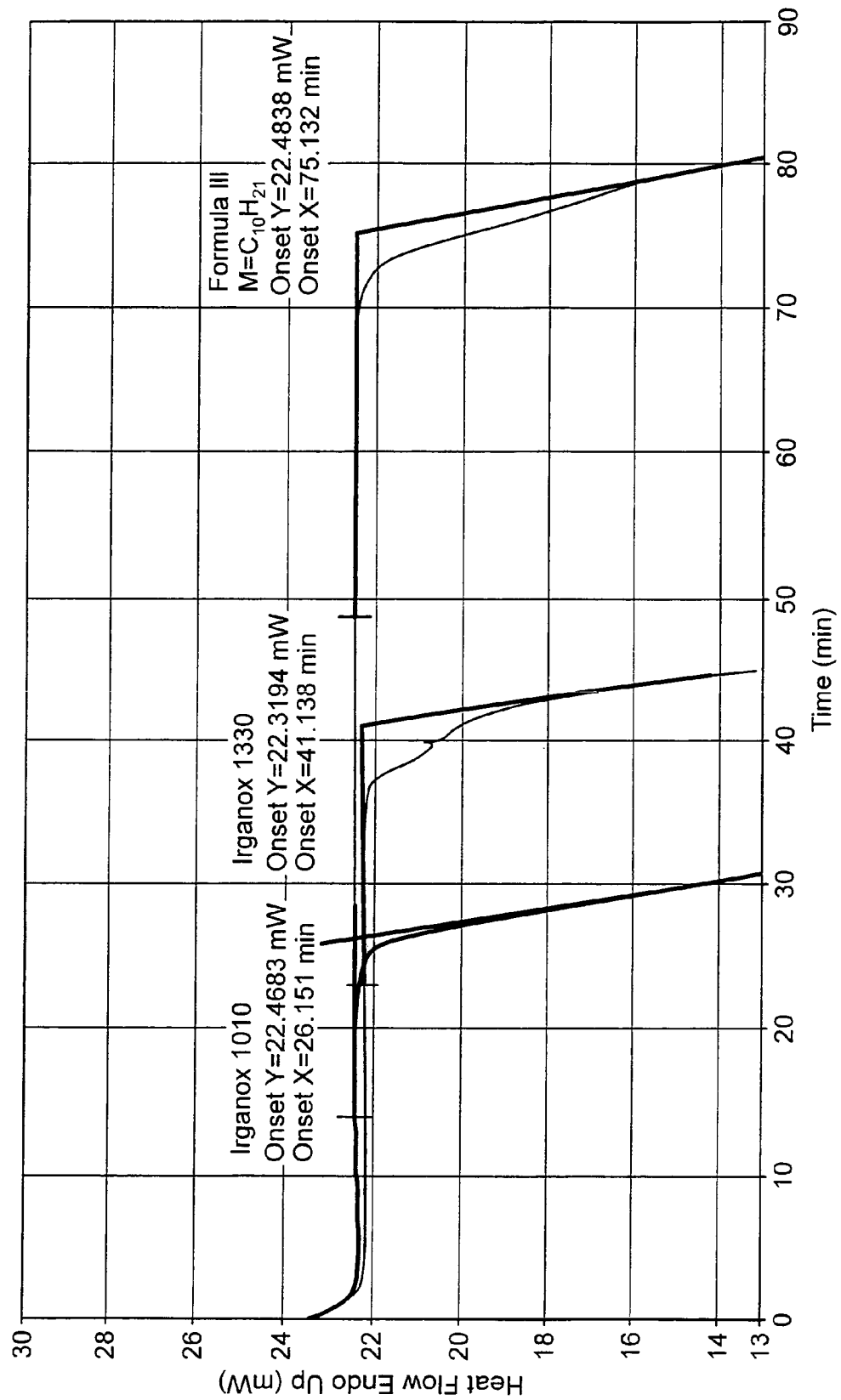
FIG. 1 is a graph showing superior performance of an alkylated macromolecule of Formula III of the present invention with M=$C_{10}H_{21}$, compared with commercially available antioxidants.

A description of preferred embodiments of the invention follows.

In certain embodiments the compounds and polymers of the present invention comprise sterically hindered groups such as phenol groups. Sterically hindered, as used herein means that the substituent group (e.g., bulky alkyl group) on a ring carbon atom adjacent (or alternatively para) to a ring carbon atom substituted with a phenolic hydroxy group (or thiol or amine group), is large enough to sterically hinder the phenolic hydroxy group (or thiol or amine groups). This steric hindrance, in certain embodiments results in more labile or weak bonding between the oxygen and the hydrogen (or sulfur or nitrogen and hydrogen) and in turn enhances the stability and antioxidant activity (proton donating activity) of the sterically hindered antioxidant.

Repeat units of the antioxidants of the invention include substituted benzene molecules. Some of these benzene molecules are typically based on phenol or a phenol derivative, such that they have at least one hydroxyl or ether functional group. In certain embodiments, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant can exert its antioxidant effect. The repeat units can also include analogous thiophenol and aniline derivatives, e.g., where the phenol —OH can be replaced by —SH, —NH—, and the like.

Substituted benzene repeat units of an antioxidant of the invention are also typically substituted with a bulky alkyl group or an n-alkoxycarbonyl group. In certain embodiments, the benzene monomers are substituted with a bulky alkyl group. In certain other embodiments, the bulky alkyl group is located ortho or meta to a hydroxyl group on the benzene ring, typically ortho. A "bulky alkyl group" is defined herein as an alkyl group that is branched alpha- or beta- to the benzene ring. In certain other embodiments, the alkyl group is branched alpha to the benzene ring. In certain other embodiments, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. In certain other embodiments, the bulky alkyl groups are unsubstituted, but they can be substituted with a functional group that does not interfere with the antioxidant activity of the molecule. Straight chained alkoxylcarbonyl groups include methoxycarbonyl, ethoxycarbonyl, n-propoxycarbonyl, n-butoxycarbonyl and n-pentoxycarbonyl. N-propoxycarbonyl is a preferred group. Similar to the bulky alkyl groups, n-alkoxycarbonyl groups are optionally substituted with a functional group that does not interfere with the antioxidant activity of the molecule.

In certain embodiments for compounds represented by Structural Formula 1:

Z is —C(O)NR'—, —NR'C(O)—, —NR'—, —CR'=N—, —C(O)—, —C(O)O—, —OC(O)—, —O—, —S—, —C(O)OC(O)— or a bond. In certain other embodiments Z is —C(O)O—, —OC(O)—, —C(O)NH—, —NHC(O)—, —NH—, —O— or —C(O)—. In certain other embodiments, Z is —C(O)NH— or —NHC(O)—. Optionally, Z is not —C(O)O—, —OC(O)—, —O— or —NH—. In various embodiments, the present invention relates to a compound of Structural Formula 1 and the attendant definitions, wherein Z is —OC(O)—. In another embodiment, Z is —C(O)O—. In another embodiment, Z is —C(O)NH—. In another embodiment, Z is —NHC(O)—. In another embodiment, Z is —NH—. In another embodiment, Z is —CH=N—. In another embodiment, Z is —C(O)—. In another embodiment, Z is —O—. In another embodiment, Z is —C(O)OC(O)—. In another embodiment, Z is a bond.

Each R' is independently —H or optionally substituted alkyl. In certain other embodiments R' is —H or an alkyl group. In certain other embodiments R' is —H or a C1-C10 alkyl group. In certain other embodiments R' is —H.

Each R is independently an optionally substituted alkyl, optionally substituted aryl, optionally substituted alkoxycarbonyl, optionally substituted ester, —OH, —$NH_2$, —SH, or

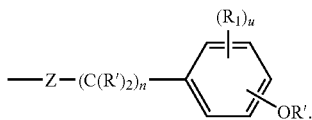

In certain other embodiments, each R is independently an optionally substituted alkyl or optionally substituted alkoxycarbonyl. In certain other embodiment each R is independently an alkyl or alkoxycarbonyl. In certain other embodiments each R is independently a C1-C6 alkyl or a C1-C6 alkoxycarbonyl. In certain other embodiments each R is independently tert-butyl or propoxycarbonyl. In certain other embodiments each R is independently an alkyl group. In certain embodiments each R is independently a bulky alkyl group. Suitable examples of bulky alkyl groups include butyl, sec-butyl, tert-butyl, 2-propyl, 1,1-dimethylhexyl, and the like. In certain embodiments each R is tert-butyl. In certain embodiments at least one R adjacent to the —OH group is a bulky alkyl group (e.g., butyl, sec-butyl, tert-butyl, 2-propyl, 1,1-dimethylhexyl, and the like). In certain other embodiments both R groups adjacent to —OH are bulky alkyl groups (e.g., butyl, sec-butyl, tert-butyl, 2-propyl, 1,1-dimethylhexyl, and the like). In another embodiment, both R groups are tert-butyl. In another embodiment, both R groups are tert-butyl adjacent to the OH group.

Each $R_1$ is independently an optionally substituted alkyl, optionally substituted aryl, optionally substituted alkoxycarbonyl, optionally substituted ester, —OH, —$NH_2$ or —SH. In certain other embodiments, each $R_1$ is independently an optionally substituted alkyl or optionally substituted alkoxycarbonyl. In certain other embodiment each $R_1$ is independently an alkyl or alkoxycarbonyl. In certain other embodiments each $R_1$ is independently a C1-C6 alkyl or a C1-C6 alkoxycarbonyl. In certain other embodiments each $R_1$ is independently tert-butyl or propoxycarbonyl. In certain other embodiments each $R_1$ is independently an alkyl group. In certain embodiments each $R_1$ is independently a bulky alkyl group. Suitable examples of bulky alkyl groups include butyl, sec-butyl, tert-butyl, 2-propyl, 1,1-dimethylhexyl, and the like. In certain embodiments each $R_1$ is tert-butyl. In certain embodiments at least one $R_1$ adjacent to the —OH group is a bulky alkyl group (e.g., butyl, sec-butyl, tert-butyl, 2-propyl, 1,1-dimethylhexyl, and the like). In certain other embodiments both $R_1$ groups adjacent to —OH are bulky alkyl groups (e.g., butyl, sec-butyl, tert-butyl, 2-propyl, 1,1-dimethylhexyl, and the like). In another embodiment, both $R_1$ groups are tert-butyl. In another embodiment, both $R_1$ groups are tert-butyl adjacent to the OH group.

Each $R_2$ is independently an optionally substituted alkyl, optionally substituted aryl, optionally substituted alkoxycarbonyl, optionally substituted ester, —OH, —$NH_2$ or —SH. In certain other embodiments, each $R_2$ is independently an optionally substituted alkyl or optionally substituted alkoxycarbonyl. In certain other embodiment each $R_2$ is independently an alkyl or alkoxycarbonyl. In certain other embodiments, each $R_2$ is independently an optionally substituted alkyl. In certain other embodiment each $R_2$ is independently an alkyl. In certain other embodiments each $R_2$ is independently a C1-C10 alkyl. In certain other embodiments each $R_2$ is independently a C1-C6 alkyl. In certain other embodiments each $R_2$ is independently a bulky alkyl group or a straight chained alkyl group. In certain other embodiments each $R_2$ is independently methyl, ethyl, propyl, butyl, sec-butyl, tert-butyl, 2-propyl or 1,1-dimethylhexyl. In certain embodiments each $R_2$ is methyl or tert-butyl.

X is —C(O)O—, —OC(O)—, —C(O)NR'—, —NR'C(O)—, —NR'—, —CH=N—, —C(O)—, —O—, —S—, —NR'— or —C(O)OC(O)—. In certain embodiments X is —NH—, —S— or —O—. In certain embodiments X is —O—. Optionally X is a bond.

M is an alkyl or

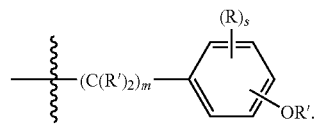

In certain embodiment M is alkyl. In certain other embodiments M is a C1-C20 linear or branched chain alkyl. In certain other embodiments M is a C5-C20 linear or branched chain alkyl. In certain other embodiments M is decane.

Each n and m are independently integers from 0 to 6. In certain embodiments each n and m are independently integers from 0 to 2.

In another embodiment, the present invention relates to a compound of Structural Formula 1 wherein n is 0.

In another embodiment, the present invention relates to a compound of Structural Formula 1 wherein m is 1.

In another embodiment, the present invention relates to a compound of Structural Formula 1 and the attendant definitions, wherein n is 0 and m is 1.

In another embodiment, the present invention relates to a compound of Structural Formula 1 wherein n is 0, m is 1, and Z is —C(O)O—.

In another embodiment, the present invention relates to a compound of Structural Formula 1 wherein n is 0, m is 1, Z is —C(O)O—, and the two R groups adjacent to the OH are tert-butyl.

Each s, q and u are independently integers from 0 to 4. In certain embodiments, each s and q are independently integers from 0 to 2. In certain embodiments, s is 2.

In certain embodiments for compounds represented by Structural Formula 1 M is not

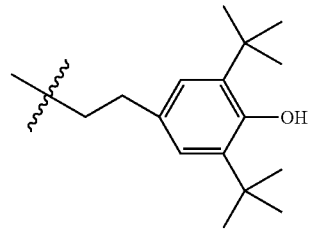

when X is —C(O)O— or —OC(O)—.

In certain embodiments for polymers represented by Structural Formula 2:

Z is —C(O)NR'—, —NR'C(O)—, —NR'—, —CR'=N—, —C(O)—, —C(O)O—, —OC(O)—, —O—, —S—, —C(O)OC(O)— or a bond. In certain other embodiments Z is —C(O)O—, —OC(O)—, —C(O)NH—, —NHC(O)—, —NH—, —O— or —C(O)—. In certain other embodiments, Z is —C(O)NH— or —NHC(O)—. Optionally, Z is not —C(O)O—, —OC(O)—, —O— or —NH—. In various embodiments, the present invention relates to a compound of Structural Formula 1 and the attendant definitions, wherein Z is —OC(O)—. In another embodiment, Z is —C(O)O—. In another embodiment, Z is —C(O)NH—. In another embodiment, Z is —NHC(O)—. In another embodiment, Z is —NH—. In another embodiment, Z is —CH=N—. In another embodiment, Z is —C(O)—. In another embodiment, Z is —O—. In another embodiment, Z is —C(O)OC(O)—. In another embodiment, Z is a bond.

Each R' is independently —H or optionally substituted alkyl. In certain other embodiments R' is —H or an alkyl group. In certain other embodiments R' is —H or a C1-C10 alkyl group. In certain other embodiments R' is —H.

Each R is independently an optionally substituted alkyl, optionally substituted aryl, optionally substituted alkoxycarbonyl, optionally substituted ester, —OH, —NH$_2$, —SH, or

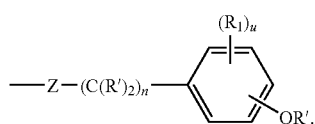

In certain other embodiments, each R is independently an optionally substituted alkyl or optionally substituted alkoxycarbonyl. In certain other embodiment each R is independently an alkyl or alkoxycarbonyl. In certain other embodiments each R is independently a C1-C6 alkyl or a C1-C6 alkoxycarbonyl. In certain other embodiments each R is independently tert-butyl or propoxycarbonyl. In certain other embodiments each R is independently an alkyl group. In certain embodiments each R is independently a bulky alkyl group. Suitable examples of bulky alkyl groups include butyl, sec-butyl, tert-butyl, 2-propyl, 1,1-dimethylhexyl, and the like. In certain embodiments each R is tert-butyl. In certain embodiments at least one R adjacent to the —OH group is a bulky alkyl group (e.g., butyl, sec-butyl, tert-butyl, 2-propyl, 1,1-dimethylhexyl, and the like). In certain other embodiments both R groups adjacent to —OH are bulky alkyl groups (e.g., butyl, sec-butyl, tert-butyl, 2-propyl, 1,1-dimethylhexyl, and the like). In another embodiment, both R groups are tert-butyl. In another embodiment, both R groups are tert-butyl adjacent to the OH group.

Each $R_1$ is independently an optionally substituted alkyl, optionally substituted aryl, optionally substituted alkoxycarbonyl, optionally substituted ester, —OH, —NH$_2$ or —SH. In certain other embodiments, each $R_1$ is independently an optionally substituted alkyl or optionally substituted alkoxycarbonyl. In certain other embodiment each $R_1$ is independently an alkyl or alkoxycarbonyl. In certain other embodiments each $R_1$ is independently a C1-C6 alkyl or a C1-C6 alkoxycarbonyl. In certain other embodiments each $R_1$ is independently tert-butyl or propoxycarbonyl. In certain other embodiments each $R_1$ is independently an alkyl group. In certain embodiments each $R_1$ is independently a bulky alkyl group. Suitable examples of bulky alkyl groups include butyl, sec-butyl, tert-butyl, 2-propyl, 1,1-dimethylhexyl, and the like. In certain embodiments each $R_1$ is tert-butyl. In certain embodiments at least one $R_1$ adjacent to the —OH group is a bulky alkyl group (e.g., butyl, sec-butyl, tert-butyl, 2-propyl, 1,1-dimethylhexyl, and the like). In certain other embodiments both $R_1$ groups adjacent to —OH are bulky alkyl groups (e.g., butyl, sec-butyl, tert-butyl, 2-propyl, 1,1-dimethylhexyl, and the like). In another embodiment, both $R_1$ groups are tert-butyl. In another embodiment, both $R_1$ groups are tert-butyl adjacent to the OH group.

Each $R_2$ is independently an optionally substituted alkyl, optionally substituted aryl, optionally substituted alkoxycarbonyl, optionally substituted ester, —OH, —NH$_2$, —SH or

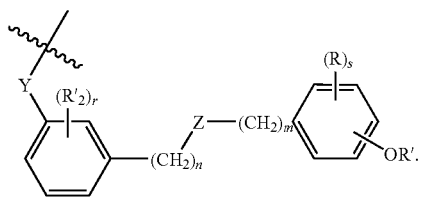

In certain other embodiments, each $R_2$ is independently an optionally substituted alkyl, optionally substituted alkoxycarbonyl or

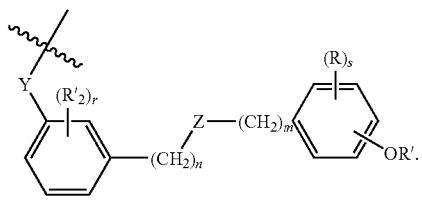

In certain other embodiment each $R_2$ is independently an alkyl or alkoxycarbonyl or

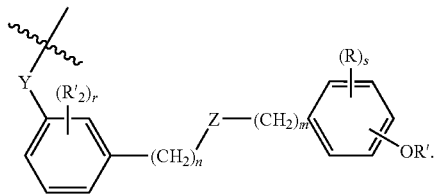

In certain other embodiments, each $R_2$ is independently an optionally substituted alkyl or

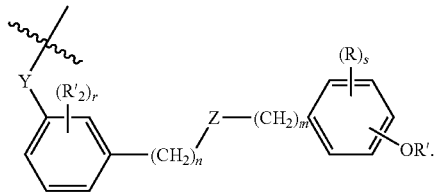

In certain other embodiment each $R_2$ is independently an alkyl or

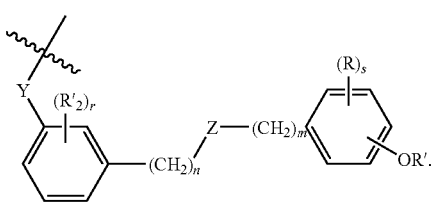

In certain other embodiments each $R_2$ is independently a C1-C10 alkyl or

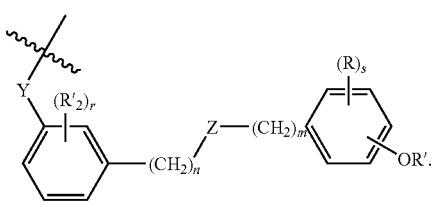

In certain other embodiments each $R_2$ is independently a C1-C6 alkyl or

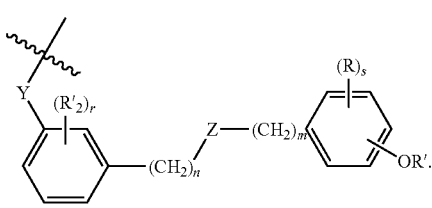

In certain other embodiments each $R_2$ is independently a bulky alkyl group, a straight chained alkyl group or

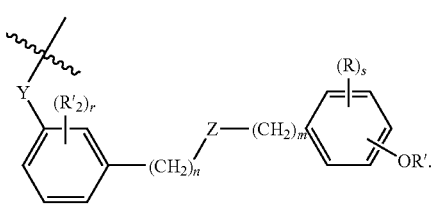

In certain other embodiments each $R_2$ is independently methyl, ethyl, propyl, butyl, sec-butyl, tert-butyl, 2-propyl, 1,1-dimethylhexyl or

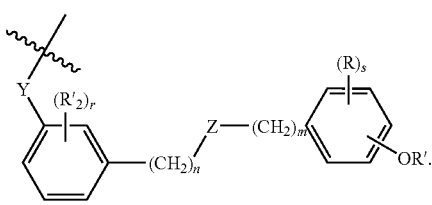

In certain embodiments each $R_2$ is methyl, tert-butyl or

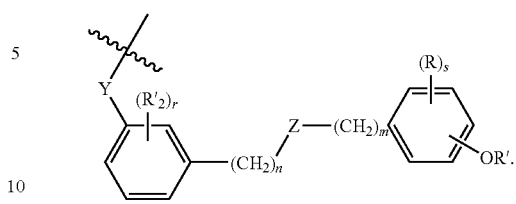

In certain embodiments described in this paragraph one $R_2$ is:

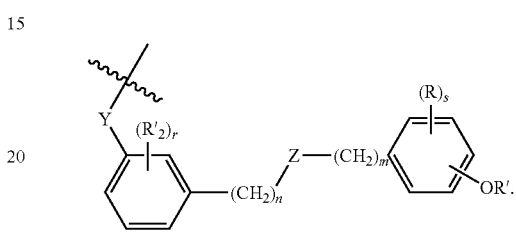

In certain embodiments described in this paragraph at least one $R_2$ is:

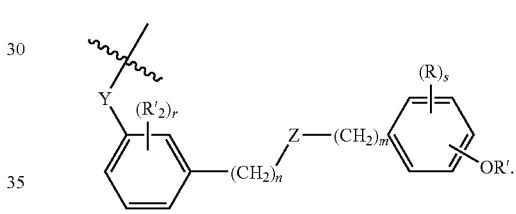

Each $R'_2$ is independently —M'—X, an optionally substituted alkyl, optionally substituted aryl, optionally substituted alkoxycarbonyl, optionally substituted ester, —OH, —NH$_2$, —SH or

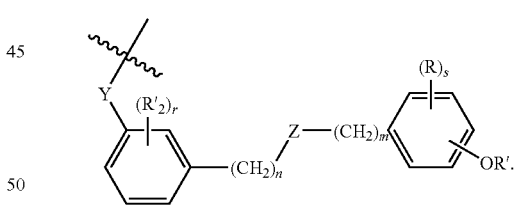

In one alternative embodiment for polymers represented by Structural Formula 2, each $R'_2$ is independently —M'—X, an optionally substituted alkyl, optionally substituted aryl, optionally substituted alkoxycarbonyl, optionally substituted ester, —OH, —NH$_2$ or —SH. In certain embodiments, each $R'_2$ is independently —M'—X, an optionally substituted alkyl, or optionally substituted alkoxycarbonyl. In certain embodiments, each $R'_2$ is independently —M'—X, an alkyl, or alkoxycarbonyl. In certain embodiments, each $R'_2$ is independently —M'—X or an alkyl. In certain embodiments, each $R'_2$ is independently —M'—X or a C1-C10 alkyl. In certain embodiments, each $R'_2$ is independently —O—(C1-C20-alkyl), —O—H or C1-C6 alkyl. In certain other embodiments each $R'_2$ is independently —O—(C5-C20-alkyl), —OH, a linear alkyl group or a bulky alkyl group. Suitable examples of bulky alkyl groups include butyl, sec-butyl, tert-butyl, 2-propyl, 1,1-dimethylhexyl, and the like. In certain other embodiments each $R'_2$ is independently —O—(C5-C20-alkyl), —OH, methyl, ethyl, propyl, butyl, sec-butyl, tert-butyl, 2-propyl, 1,1-dimethylhexyl, and the like.

In another alternative embodiment for polymers represented by Structural Formula 2, each $R'_2$ is independently —M'—X, an optionally substituted alkyl, optionally substituted aryl, optionally substituted alkoxycarbonyl, optionally substituted ester, —OH, —NH$_2$, —SH or

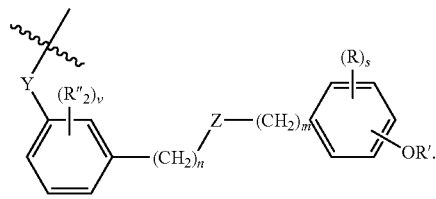

In certain embodiments, each $R'_2$ is independently —M'—X, an optionally substituted alkyl, optionally substituted alkoxycarbonyl or

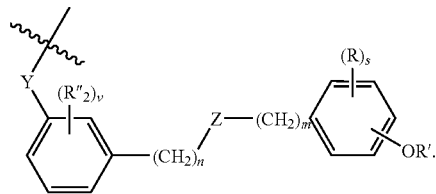

In certain embodiments, each $R'_2$ is independently —M'—X, an alkyl, alkoxycarbonyl or

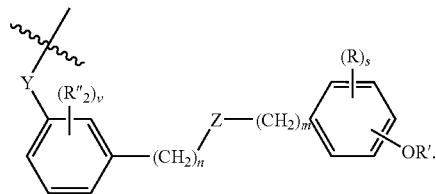

In certain embodiments, each $R'_2$ is independently —M'—X, an alkyl or

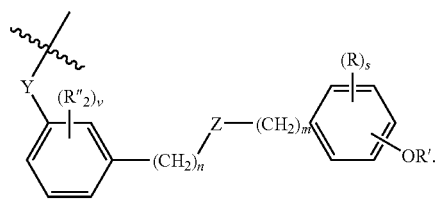

In certain embodiments, each $R'_2$ is independently —M'—X or a C1-C10 alkyl. In certain embodiments, each $R'_2$ is independently —O—(C1-C20-alkyl), —O—H, C1-C6 alkyl or

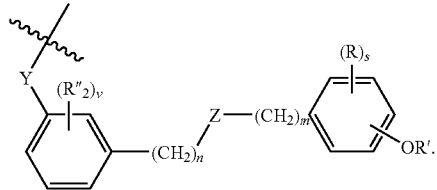

In certain other embodiments each $R'_2$ is independently —O—(C5-C20-alkyl), —OH, a linear alkyl group or a bulky alkyl group, or

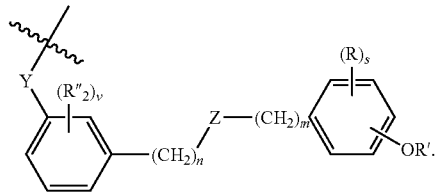

Suitable examples of bulky alkyl groups include butyl, sec-butyl, tert-butyl, 2-propyl, 1,1-dimethylhexyl, and the like. In certain other embodiments each $R'_2$ is independently —O—(C5-C20-alkyl), —OH, methyl, ethyl, propyl, butyl, sec-butyl, tert-butyl, 2-propyl, 1,1-dimethylhexyl, and the like or

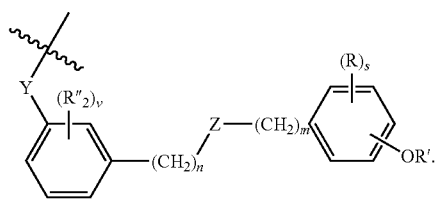

In certain embodiments described in this paragraph at least one $R'_2$ is:

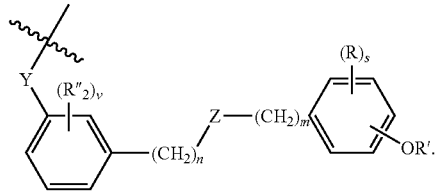

In certain embodiments, for polymers represented by Structural Formula 2, each $R''_2$ is independently —M'—X, an optionally substituted alkyl, optionally substituted aryl, optionally substituted alkoxycarbonyl, optionally substituted ester, —OH, —NH$_2$, —SH or

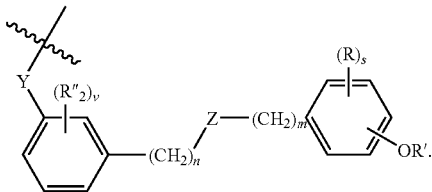

In certain embodiments, each R"$_2$ is independently —M'—X, an optionally substituted alkyl, optionally substituted alkoxycarbonyl or

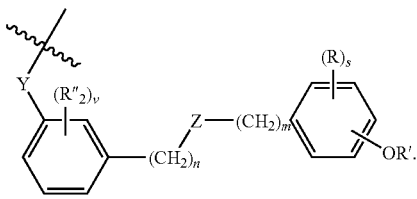

In certain embodiments, each R"$_2$ is independently —M'—X, an alkyl, alkoxycarbonyl or

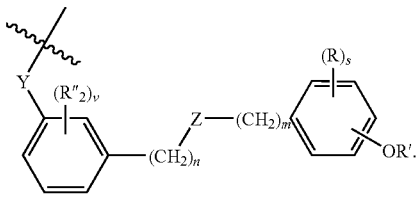

In certain embodiments, each R"$_2$ is independently —M'—X, an alkyl or

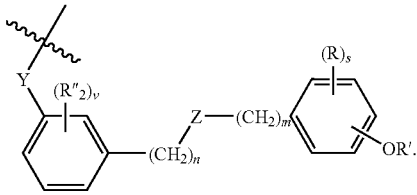

In certain embodiments, each R"$_2$ is independently —M'—X or a C1-C10 alkyl. In certain embodiments, each R"$_2$ is independently —O—(C1-C20-alkyl), —O—H, C1-C6 alkyl or

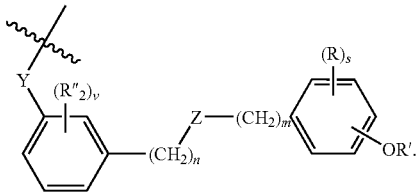

In certain other embodiments each R"$_2$ is independently —O—(C5-C20-alkyl), —OH, a linear alkyl group or a bulky alkyl group, or

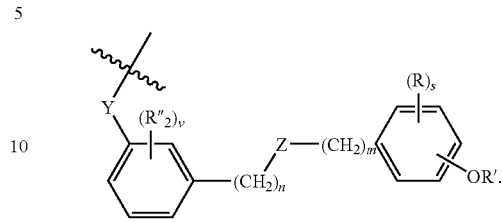

Suitable examples of bulky alkyl groups include butyl, sec-butyl, tert-butyl, 2-propyl, 1,1-dimethylhexyl, and the like. In certain other embodiments each R"$_2$ is independently —O—(C5-C20-alkyl), —OH, methyl, ethyl, propyl, butyl, sec-butyl, tert-butyl, 2-propyl, 1,1-dimethylhexyl, and the like or

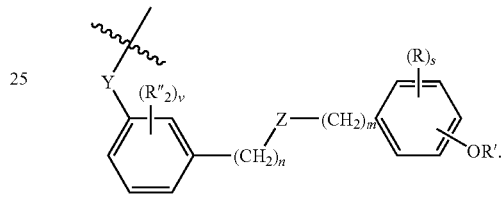

X is —C(O)O—, —OC(O)—, —C(O)NR'—, —NR'C(O)—, —NR'—, —CH=N—, —C(O)—, —O—, —S—, —NR'— or —C(O)OC(O)—. In certain embodiments X is —NH—, —S— or —O—. In certain embodiments X is —O—. Optionally X is a bond.

Each M' is independently —H, alkyl or

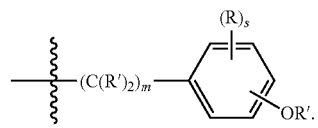

In certain embodiments each M' is independently —H or alkyl. In certain other embodiments each M' is independently —H or a C1-C20 linear or branched chain alkyl. In certain other embodiments each M' is independently —H or a C5-C20 linear or branched chain alkyl. In certain other embodiments each M' is independently —H or decane. In certain embodiments for polymers of the present invention represented by Structural Formula 2 at least one M' is not —H. In certain embodiments for polymers of the present invention represented by Structural Formula 2 at least one R'$_2$ is —M'—X.

Each Y is independently Q—W—Q'. In certain embodiments, Y is Q—W—Q' as defined below, which in certain embodiments is —(C(R")$_2$)$_p$—, —(C(R")$_2$)$_p$-phenylene-(C(R")$_2$)$_p$— or —(C(R")$_2$)$_p$N(OH)(C(R")$_2$)$_p$—. In certain embodiments, Y is Q—W—Q' as defined below, which in certain embodiments is —C(R")$_2$—, —C(R")$_2$-phenylene-C(R")$_2$— or —C(R")$_2$N(OH)C(R")$_2$—. In certain embodiments Y is Q—W—Q' as defined below, which in certain embodiments is —CH$_2$, —CH$_2$N(OH)CH$_2$— or

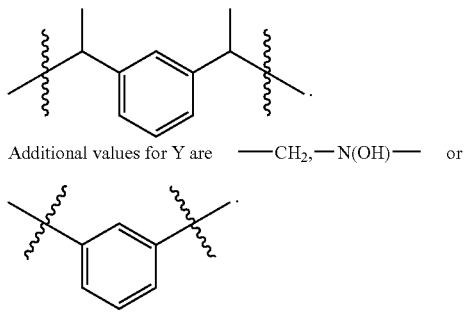

Additional values for Y are —CH₂—N(OH)— or

Each Q is independently an optionally substituted C1-C20 alkylene group. In certain embodiments, each Q is independently an optionally substituted C1-C10 alkylene group. In certain embodiments, each Q is independently —(CH₂)₁₋₁₀—, CH(CH₃) or C(CH₃)₂. In certain embodiments, each Q is independently —CH₂—, CH(CH₃) or C(CH₃)₂.

Each Q' is independently a bond or an optionally substituted C1-C20 alkylene group. In certain embodiments, each Q' is independently a bond or an optionally substituted C1-C10 alkylene group. In certain embodiments, each Q' is independently —(CH₂)₁₋₁₀—, CH(CH₃) or C(CH₃)₂. In certain embodiments, each Q' is independently a bond, —CH₂—, CH(CH₃) or C(CH₃)₂.

Each W is independently arylene, —O—, —S—, —NR'—, —N(OR')—, —C(=N(OR'))—, —C(O)NR'—, —NR'C(O)—, —CR'=N—, —C(O)—, —C(O)O—, —OC(O)—, —C(O)OC(O)— or a bond. In certain embodiments, each W is independently arylene, —O—, —S—, —NH—, —N(OH)—, —C(=N(OH))— or a bond. In certain embodiments W is a bond, phenylene or —N(OH)—.

Each R" is independently —H or optionally substituted alkyl. In certain embodiments, each R" is independently —H or alkyl. In certain embodiments, each R" is independently —H or a linear or branched C1-C10 alkyl. In certain embodiments, each R" is —H or a C1-C3 linear or branched alkyl. In certain embodiments each R" is —H.

Each n and m are independently integers from 0 to 6. In certain embodiments, each n and m are independently integers from 0 to 2.

In another embodiment, the present invention relates to a polymer of Structural Formula 2 wherein n is 0.

In another embodiment, the present invention relates to a polymer of Structural Formula 2 wherein m is 1.

In another embodiment, the present invention relates to a polymer of Structural Formula 2 wherein n is 0 and m is 1.

In another embodiment, the present invention relates to a polymer of Structural Formula 2 wherein n is 0, m is 1, and Z is —C(O)O—.

In another embodiment, the present invention relates to a polymer of Structural Formula 2 wherein n is 0, m is 1, Z is —C(O)O—, and the two R groups adjacent to the OH are tert-butyl.

Each s, q and u are independently integers from 0 to 4. In certain embodiments, q is an integer from 1 to 3. In certain embodiments, s is 2.

Each r is an integer from 0 to 4. In certain embodiments, each s and r are independently integers from 0 to 2. In certain embodiments each r and q are independently integers from 1 to 3.

Each v is an integer from 0 to 4. In certain embodiments each s and v are independently integers from 0 to 2.

Each p is independently an integer of 1 to 5.

In certain embodiments for compounds represented by Structural Formula 3:

Z is —C(O)NR'—, —NR'C(O)—, —NR'—, —CR'=N—, —C(O)—, —C(O)O—, —OC(O)—, —O—, —S—, —C(O)OC(O)— or a bond. In certain other embodiments Z is —C(O)O—, —OC(O)—, —C(O)NH—, —NHC(O)—, —NH—, —O— or —C(O)—. In certain other embodiments, Z is —C(O)NH— or —NHC(O)—. Optionally, Z is not —C(O)O—, —OC(O)—, —O— or —NH—. In various embodiments, the present invention relates to a polymer of Structural Formula 2 and the attendant definitions, wherein Z is —OC(O)—. In another embodiment, Z is —C(O)O—. In another embodiment, Z is —C(O)NH—. In another embodiment, Z is —NHC(O)—. In another embodiment, Z is —NH—. In another embodiment, Z is —CH=N—. In another embodiment, Z is —C(O)—. In another embodiment, Z is —O—. In another embodiment, Z is —C(O)OC(O)—. In another embodiment, Z is a bond.

Each R' is independently —H or optionally substituted alkyl. In certain other embodiments R' is —H or an alkyl group. In certain other embodiments R' is —H or a C1-C10 alkyl group. In certain other embodiments R' is —H.

Each R is independently an optionally substituted alkyl, optionally substituted aryl, optionally substituted alkoxycarbonyl, optionally substituted ester, —OH, —NH₂, —SH, or

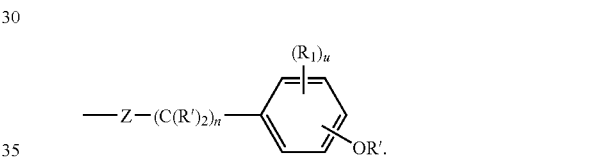

In certain other embodiments, each R is independently an optionally substituted alkyl or optionally substituted alkoxycarbonyl. In certain other embodiment each R is independently an alkyl or alkoxycarbonyl. In certain other embodiments each R is independently a C1-C6 alkyl or a C1-C6 alkoxycarbonyl. In certain other embodiments each R is independently tert-butyl or propoxycarbonyl. In certain other embodiments each R is independently an alkyl group. In certain embodiments each R is independently a bulky alkyl group. Suitable examples of bulky alkyl groups include butyl, sec-butyl, tert-butyl, 2-propyl, 1,1-dimethylhexyl, and the like. In certain embodiments each R is tert-butyl. In certain embodiments at least one R adjacent to the —OH group is a bulky alkyl group (e.g., butyl, sec-butyl, tert-butyl, 2-propyl, 1,1-dimethylhexyl, and the like). In certain other embodiments both R groups adjacent to —OH are bulky alkyl groups (e.g., butyl, sec-butyl, tert-butyl, 2-propyl, 1,1-dimethylhexyl, and the like). In another embodiment, both R groups are tert-butyl. In another embodiment, both R groups are tert-butyl adjacent to the OH group.

Each $R_1$ is independently an optionally substituted alkyl, optionally substituted aryl, optionally substituted alkoxycarbonyl, optionally substituted ester, —OH, —NH₂ or —SH. In certain other embodiments, each $R_1$ is independently an optionally substituted alkyl or optionally substituted alkoxycarbonyl. In certain other embodiment each $R_1$ is independently an alkyl or alkoxycarbonyl. In certain other embodiments each $R_1$ is independently a C1-C6 alkyl or a C1-C6 alkoxycarbonyl. In certain other embodiments each $R_1$ is independently tert-butyl or propoxycarbonyl. In certain other embodiments each $R_1$ is independently an alkyl group. In certain embodiments each $R_1$ is independently a bulky alkyl group. Suitable examples of bulky alkyl groups include butyl, sec-butyl, tert-butyl, 2-propyl, 1,1-dimethylhexyl, and the like. In certain embodiments each $R_1$ is tert-butyl. In certain embodiments at least one $R_1$ adjacent to the —OH group is a bulky alkyl group (e.g., butyl, sec-butyl, tert-butyl, 2-propyl, 1,1-dimethylhexyl, and the like). In certain other embodiments both $R_1$ groups adjacent to —OH are bulky alkyl groups (e.g., butyl, sec-butyl, tert-butyl, 2-propyl, 1,1-dimethylhexyl, and the like). In another embodiment, both $R_1$ groups are tert-butyl. In another embodiment, both $R_1$ groups are tert-butyl adjacent to the OH group.

Each $R_2$ is independently an optionally substituted alkyl, optionally substituted aryl, optionally substituted alkoxycarbonyl, optionally substituted ester, —OH, —$NH_2$ or —SH. In certain other embodiments, each $R_2$ is independently an optionally substituted alkyl or optionally substituted alkoxycarbonyl. In certain other embodiment each $R_2$ is independently an alkyl or alkoxycarbonyl. In certain other embodiments, each $R_2$ is independently an optionally substituted alkyl. In certain other embodiment each $R_2$ is independently an alkyl. In certain other embodiments each $R_2$ is independently a C1-C10 alkyl. In certain other embodiments each $R_2$ is independently a C1-C6 alkyl. In certain other embodiments each $R_2$ is independently a bulky alkyl group or a straight chained alkyl group. In certain other embodiments each $R_2$ is independently methyl, ethyl, propyl, butyl, sec-butyl, tert-butyl, 2-propyl or 1,1-dimethylhexyl. In certain embodiments each $R_2$ is methyl or tert-butyl.

X is —C(O)O—, —OC(O)—, —C(O)NR'—, —NR'C(O)—, —NR'—, —CH=N—, —C(O)—, —O—, —S—, —NR'— or —C(O)OC(O)—. In certain embodiments X is —NH—, —S— or —O—. In certain embodiments X is —O—. Optionally X is a bond.

Each M' is independently —H, alkyl or

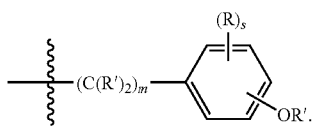

In certain embodiments each M' is independently —H or alkyl. In certain other embodiments each M' is independently —H or a C1-C20 linear or branched chain alkyl. In certain other embodiments each M' is independently —H or a C5-C20 linear or branched chain alkyl. In certain other embodiments each M' is independently —H or decane. In certain other embodiments each M' is —H.

Each n and m are independently integers from 0 to 6. In certain embodiments each n and m are independently integers from 0 to 2.

In another embodiment, the present invention relates to a composition comprising a compound of Structural Formula 1 and a compound of Structural Formula 3 wherein n is 0.

In another embodiment, the present invention relates to a composition comprising a compound of Structural Formula 1 and a compound of Structural Formula 3 wherein m is 1.

In another embodiment, the present invention relates to a composition comprising a compound of Structural Formula 1 and a compound of Structural Formula 3 wherein n is 0 and m is 1.

In another embodiment, the present invention relates to a composition comprising a compound of Structural Formula 1 and a compound of Structural Formula 3 wherein n is 0, m is 1, and Z is —C(O)O—.

In another embodiment, the present invention relates to a composition comprising a compound of Structural Formula 1 and a compound of Structural Formula 3 wherein n is 0, m is 1, Z is —C(O)O—, and the two R groups adjacent to the OH are tert-butyl.

Each s, q and u are independently integers from 0 to 4. In certain embodiments, each s and q are independently integers from 0 to 2. In certain embodiments, s is 2.

In a first embodiment the present invention is directed to a compound represented by Structural Formula 1:

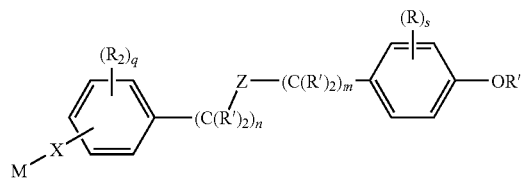

Z is —C(O)NR'—, —NR'C(O)—, —NR'—, —CR'=N—, —C(O)—, —C(O)O—, —OC(O)—, —O—, —S—, —C(O)OC(O)— or a bond.

Each R' is independently —H or optionally substituted alkyl.

Each R is independently an optionally substituted alkyl, optionally substituted aryl, optionally substituted alkoxycarbonyl, optionally substituted ester, —OH, —$NH_2$, —SH, or

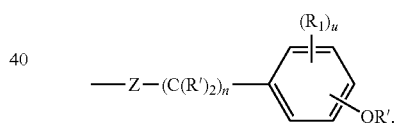

In certain embodiments at least one R adjacent to the —OH group is a bulky alkyl group (e.g., butyl, sec-butyl, tert-butyl, 2-propyl, 1,1-dimethylhexyl, and the like). In certain other embodiments both R groups adjacent to —OH are bulky alkyl groups (e.g., butyl, sec-butyl, tert-butyl, 2-propyl, 1,1-dimethylhexyl, and the like). In another embodiment, both R groups are tert-butyl. In another embodiment, both R groups are tert-butyl adjacent to the OH group.

Each $R_1$ is independently an optionally substituted alkyl, optionally substituted aryl, optionally substituted alkoxycarbonyl, optionally substituted ester, —OH, —$NH_2$ or —SH. In certain embodiments at least one $R_1$ adjacent to the —OH group is a bulky alkyl group (e.g., butyl, sec-butyl, tert-butyl, 2-propyl, 1,1-dimethylhexyl, and the like). In certain other embodiments both $R_1$ groups adjacent to —OH are bulky alkyl groups (e.g., butyl, sec-butyl, tert-butyl, 2-propyl, 1,1-dimethylhexyl, and the like). In another embodiment, both $R_1$ groups are tert-butyl. In another embodiment, both $R_1$ groups are tert-butyl adjacent to the OH group.

Each $R_2$ is independently an optionally substituted alkyl, optionally substituted aryl, optionally substituted alkoxycarbonyl, optionally substituted ester, —OH, —$NH_2$ or —SH.

X is —C(O)O—, —OC(O)—, —C(O)NR'—, —NR'C(O)—, —NR'—, —CH=N—, —C(O)—, —O—, —S—, —NR'— or —C(O)OC(O)—. Optionally an additional value of X is a bond.

M is an alkyl or

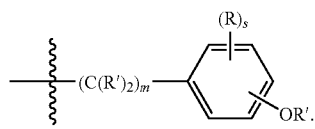

Each n and m are independently integers from 0 to 6.
Each s, q and u are independently integers from 0 to 4. In certain embodiments for compounds of Structural Formula 1 M is not:

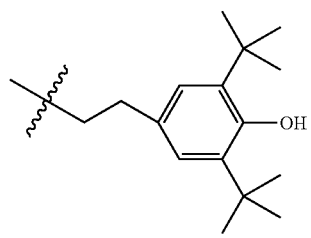

when X is —C(O)O— or —OC(O)—.

In a second embodiment of the present invention directed to a compound represented by Structural Formula 1:
Z is —C(O)O—, —OC(O)—, —C(O)NH—, —NHC(O)—, —NH—, —O— or —C(O)—.
R' is —H.
Each R is independently an optionally substituted alkyl or optionally substituted alkoxycarbonyl.
Each $R_2$ is independently an optionally substituted alkyl.
X is —O—.
M is an alkyl. In certain embodiments M is a C1-C20 alkyl.

Each n and m are independently integers from 0 to 2.
each s and q are independently integers from 0 to 2, and the remainder of the variables are as described above in the first embodiment.

In a third embodiment of the present invention directed to a compound represented by Structural Formula 1:
Z is —C(O)NH— or —NHC(O)—.
Each R is independently an alkyl or an alkoxycarbonyl.
Each $R_2$ is independently an alkyl.
s is 2, and the remainder of the variables are as described above in the second embodiment.

In a fourth embodiment of the present invention directed to a compound represented by Structural Formula 1:
Each R is independently an alkyl group, and the remainder of the variables are as described above in the third embodiment. In certain embodiments each R is a bulky alkyl group. In certain embodiments two R groups are bulky alkyl groups adjacent to the —H group. In certain embodiments the two R groups are tert-butyl groups adjacent to the —OH group.

In a fifth embodiment of the present invention directed to a compound represented by Structural Formula 1, the compound is represented by Structural Formula III:

III

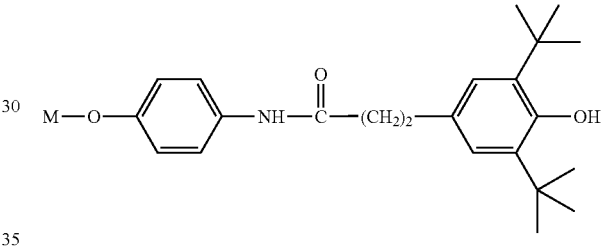

M is a C1 to C20 linear or branched alkyl chain.

In a sixth embodiment of the present invention directed to a compound represented by Structural Formula 1, the compound is represented by a Structural Formula selected from:

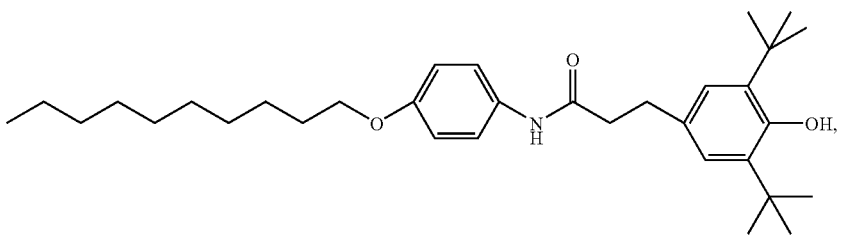

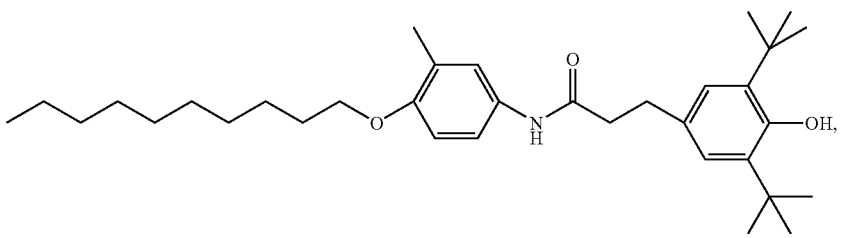

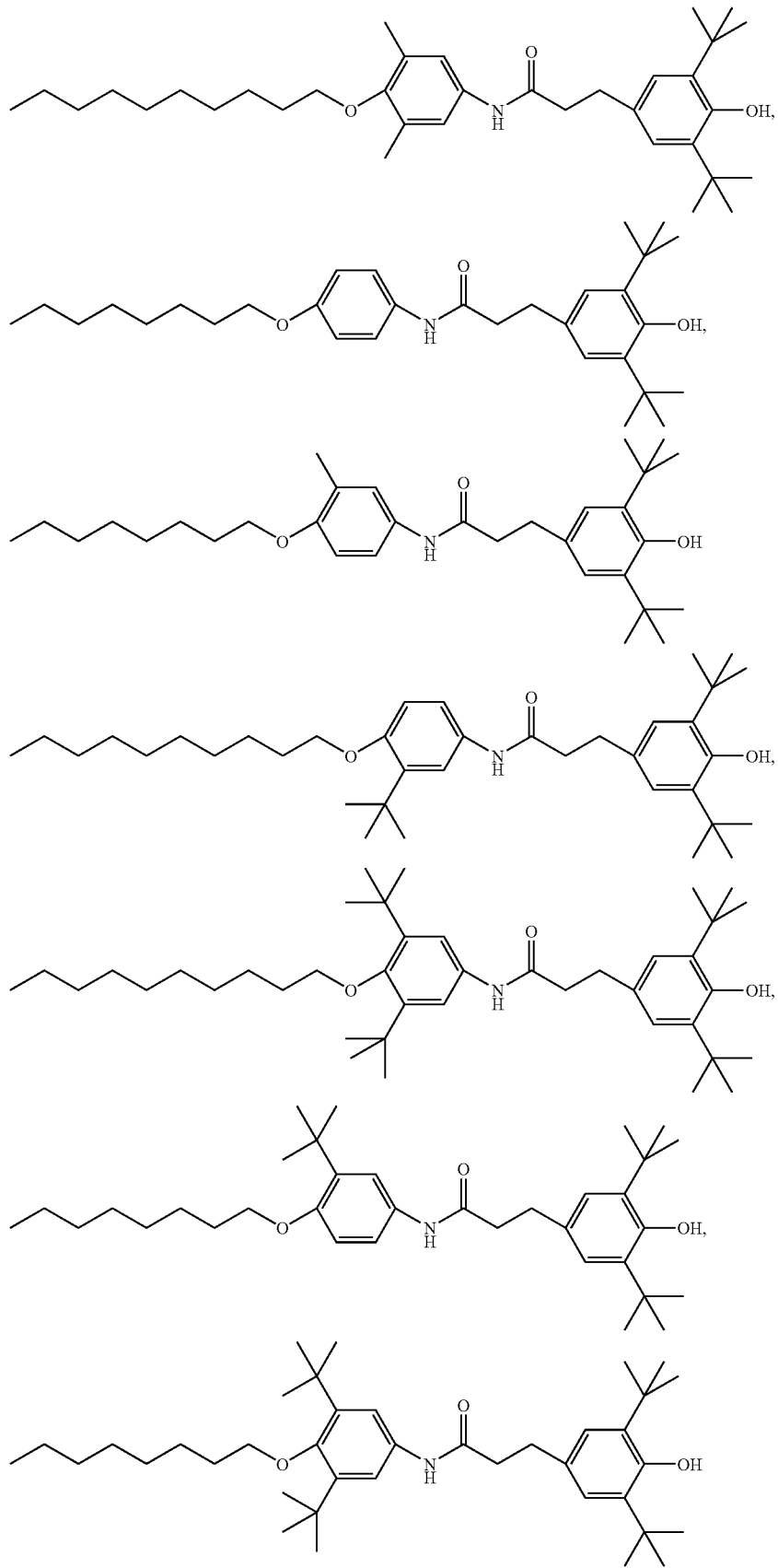

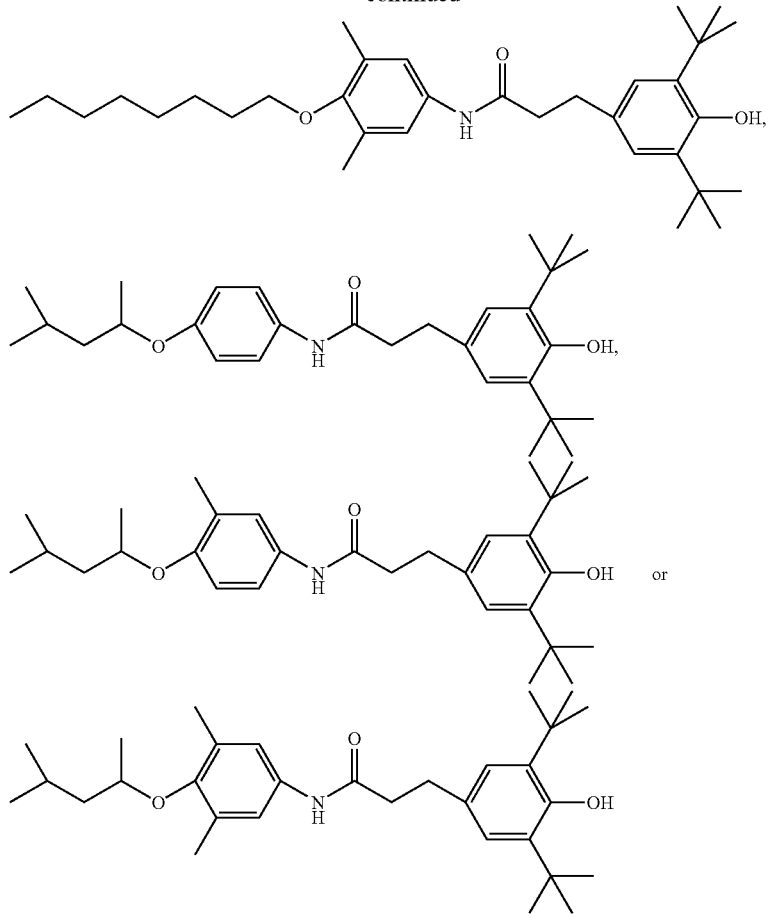

In certain embodiment the present invention is directed to polymers comprising at least two repeat units at least one of which is represented by Structural Formula 1. In certain other embodiments the present invention is directed to polymers comprising at least two repeat units at least one of which is Structural Formula 1 where an additional value for M can be —H and the repeat units are connected by at least one methylene group.

In a first embodiment of the present invention directed to a polymer represented by Structural Formula 2:

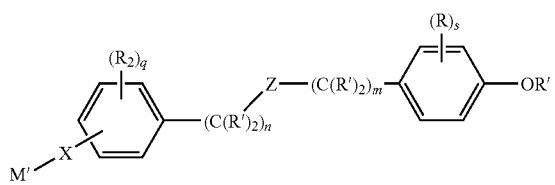

Z is —C(O)NR'—, —NR'C(O)—, —NR'—, —CR'=N—, —C(O)—, —C(O)O—, —OC(O)—, —O—, —S—, —C(O)OC(O)— or a bond.

Each R' is independently —H or optionally substituted alkyl.

Each R is independently an optionally substituted alkyl, optionally substituted aryl, optionally substituted alkoxycarbonyl, optionally substituted ester, —OH, —NH$_2$, —SH, or

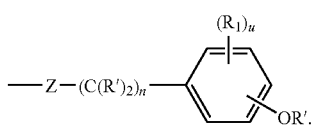

In certain embodiments at least one R adjacent to the —OH group is a bulky alkyl group (e.g., butyl, sec-butyl, tert-butyl, 2-propyl, 1,1-dimethylhexyl, and the like). In certain other embodiments both R groups adjacent to —OH are bulky alkyl groups (e.g., butyl, sec-butyl, tert-butyl, 2-propyl, 1,1-dimethylhexyl, and the like). In another embodiment, both R groups are tert-butyl. In another embodiment, both R groups are tert-butyl adjacent to the OH group.

Each $R_1$ is independently an optionally substituted alkyl, optionally substituted aryl, optionally substituted alkoxycarbonyl, optionally substituted ester, —OH, —NH$_2$ or —SH. In certain embodiments at least one $R_1$ adjacent to the —OH group is a bulky alkyl group (e.g., butyl, sec-butyl, tert-butyl, 2-propyl, 1,1-dimethylhexyl, and the like). In certain other embodiments both $R_1$ groups adjacent to —OH are bulky alkyl groups (e.g., butyl, sec-butyl, tert-butyl, 2-propyl, 1,1-dimethylhexyl, and the like). In another embodiment, both $R_1$ groups are tert-butyl. In another embodiment, both $R_1$ groups are tert-butyl adjacent to the OH group.

Each $R_2$ is independently an optionally substituted alkyl, optionally substituted aryl, optionally substituted alkoxycarbonyl, optionally substituted ester, —OH, —$NH_2$, —SH or

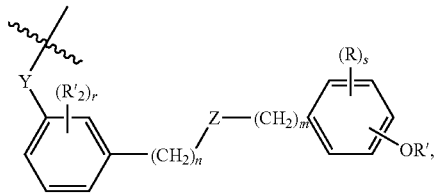

wherein at least one $R_2$ is

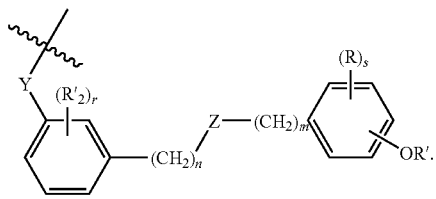

Each $R'_2$ is independently —M'—X, an optionally substituted alkyl, optionally substituted aryl, optionally substituted alkoxycarbonyl, optionally substituted ester, —OH, —$NH_2$, —SH or

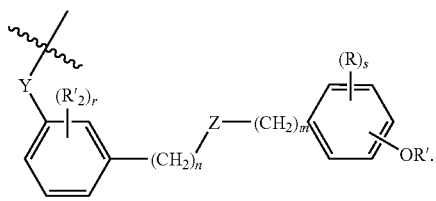

X is —C(O)O—, —OC(O)—, —C(O)NR'—, —NR'C(O)—, —NR'—, —CR'=N—, —C(O)—, —O—, —S—, —NR'— or —C(O)OC(O)—. Optionally an additional value for X is a bond.

Each Y is independently Q—W—Q'.

Each Q is independently an optionally substituted C1-C20 alkylene group.

Each Q' is independently a bond or an optionally substituted C1-C20 alkylene group.

Each W is independently arylene, —O—, —S—, —NR'—, —N(OR')—, —C(=N(OR'))—, —C(O)NR'—, —NR'C(O)—, —CR'=N—, —C(O)—, —C(O)O—, —OC(O)—, —C(O)OC(O)—, or a bond.

Each M' is independently —H, alkyl, or

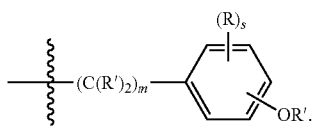

Each n and m are independently integers from 0 to 6.
Each s, q and u are independently integers from 0 to 4.
r is an integer from 0 to 4.

In a second embodiment of the present invention directed to a polymer represented by Structural Formula 2:

Z is —C(O)O—, —OC(O)—, —C(O)NH—, —NHC(O)—, —NH—, —O— or —C(O)—.

R' is —H.

Each R is independently an optionally substituted alkyl or optionally substituted alkoxycarbonyl.

Each $R_2$ is independently an optionally substituted alkyl or

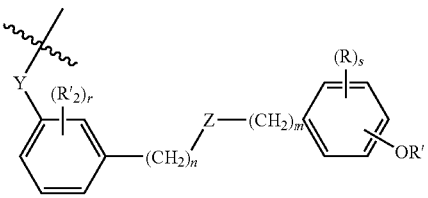

wherein one $R_2$ is:

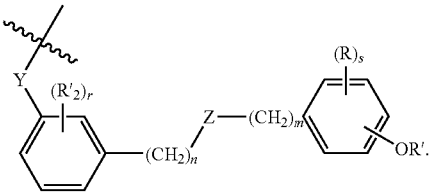

Each $R'_2$ is independently —M—X or an optionally substituted alkyl.

Each M' is independently —H or alkyl.

X is —O—.

Each Q is independently an optionally substituted C1-C10 alkylene group.

Each Q' is independently a bond or an optionally substituted C1-C10 alkylene group.

Each W is independently arylene, —O—, —S—, —NH—, —N(OH)—, —C(=N(OH))—, or a bond.

Each n and m are independently integers from 0 to 2.
Each s and r are independently integers from 0 to 2.
q is an integer from 1 to 3, and the remainder of the variables are as described above in the first embodiment.

In a third embodiment of the present invention directed to a polymer represented by Structural Formula 2:

Z is —C(O)NH— or —NHC(O)—.

Each R is independently an alkyl or an alkoxycarbonyl.

s is 2 and the remainder of the variables are as described above in the second embodiment.

In a fourth embodiment of the present invention directed to a polymer represented by Structural Formula 2:

Each R is independently an alkyl group. In certain embodiments R is a bulky alkyl group. In certain embodiments the two R groups are bulky alkyl groups adjacent to the —OH group. In certain embodiments the two R groups are tert-butyl groups adjacent to the —OH group.

Y is —C(R'')$_2$—, —(C(R'')$_2$)$_p$-phenylene-(C(R'')$_2$)$_p$— or —(C(R'')$_2$)$_p$N(OH)(C(R'')$_2$)$_p$.

Each R'' is —H or alkyl.

Each p is independently an integer of 1 to 5, and the remainder of the variables are as described above in the third embodiment.

In a fifth embodiment of the present invention directed to a polymer represented by Structural Formula 2, the polymer is represented by a Structural Formula selected from:

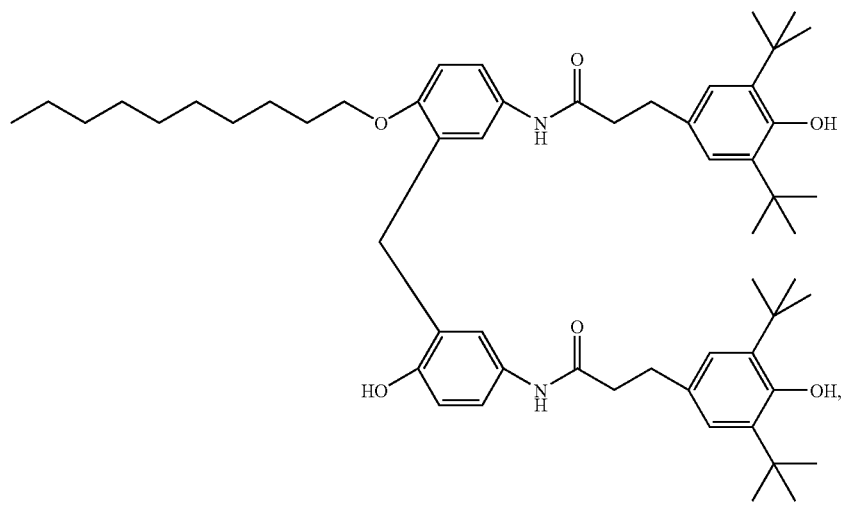
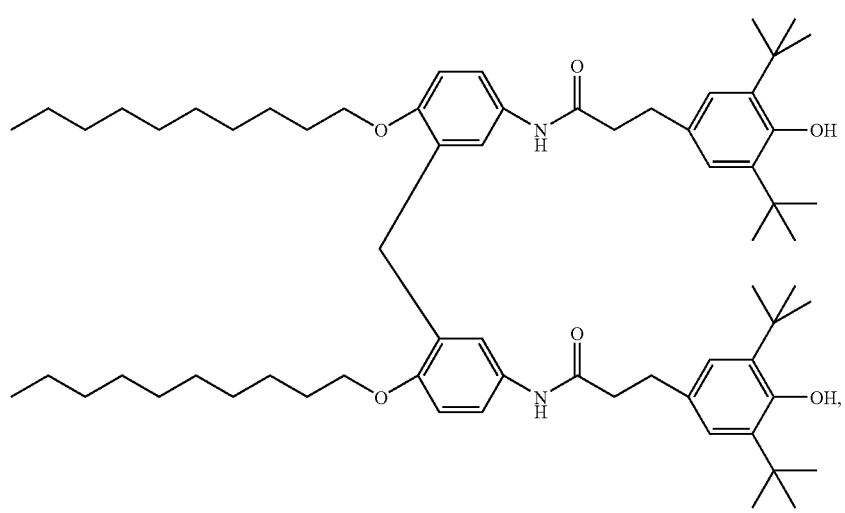
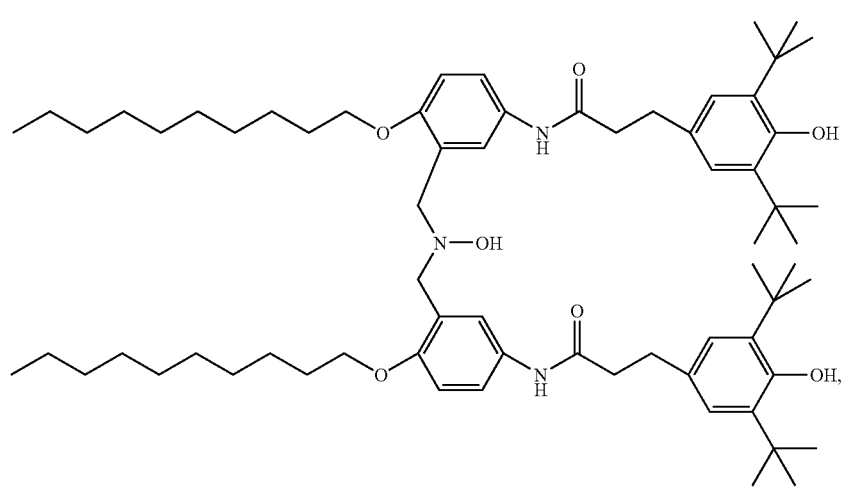

-continued
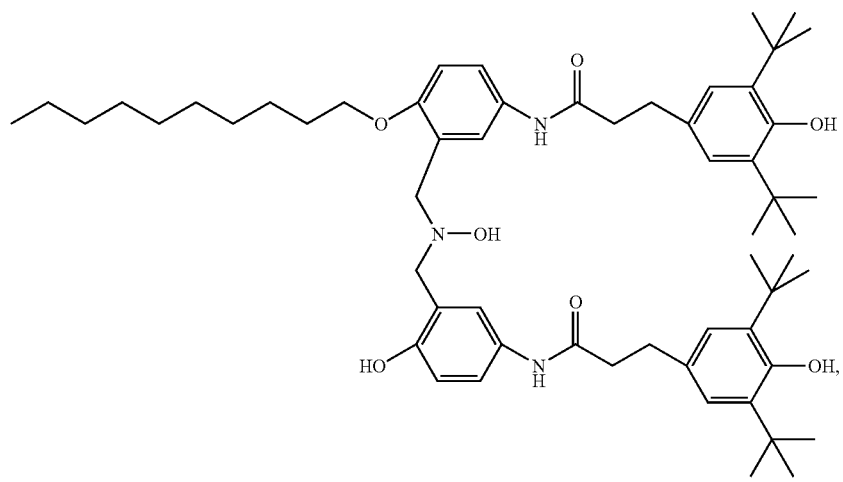
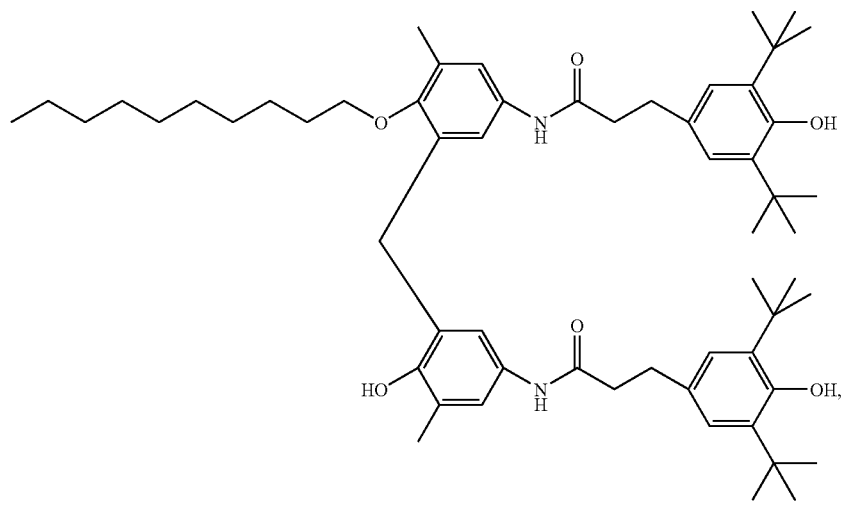
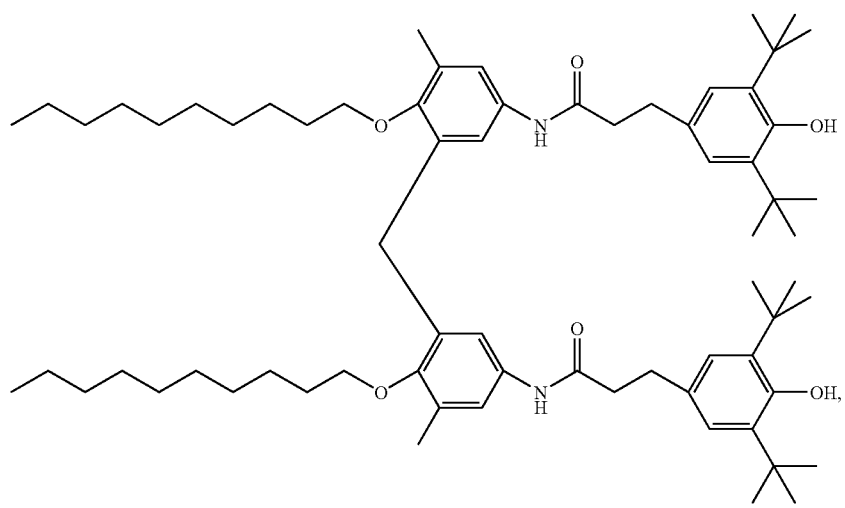

-continued
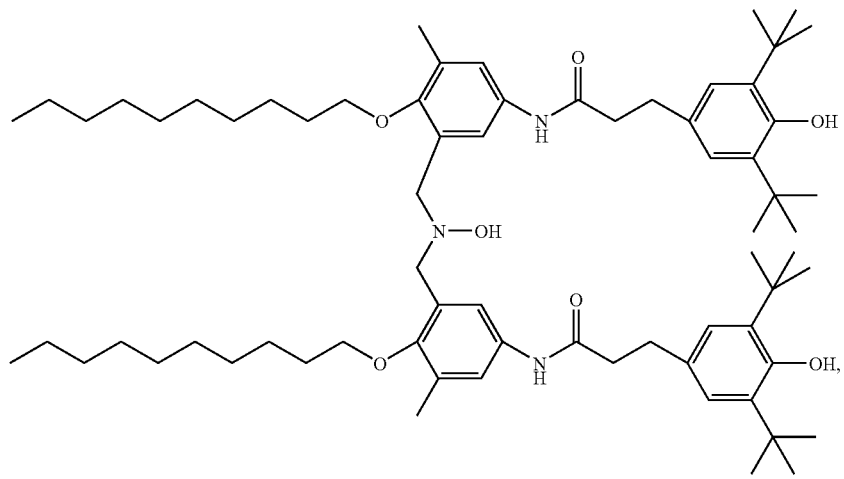
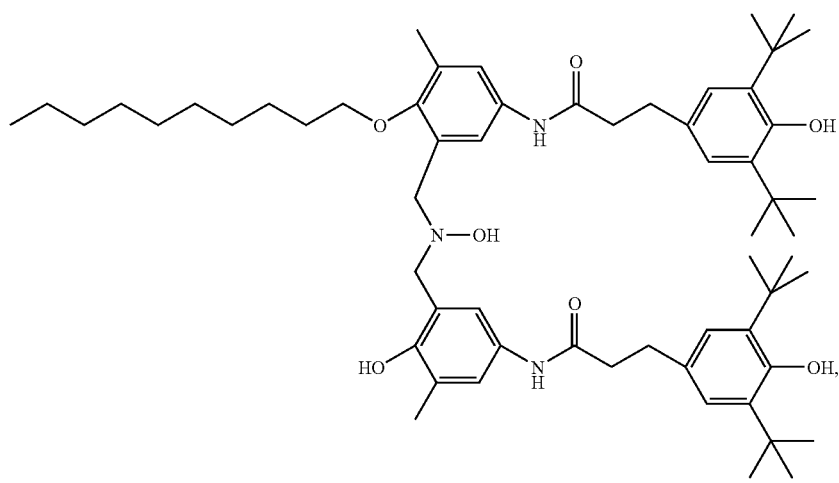
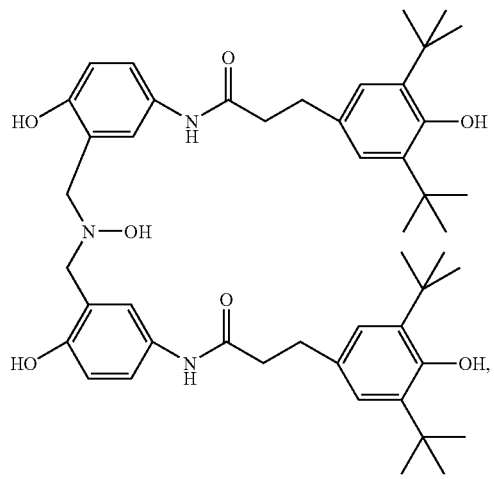
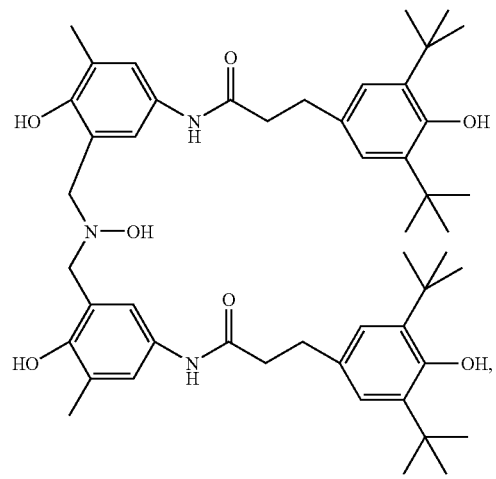

-continued
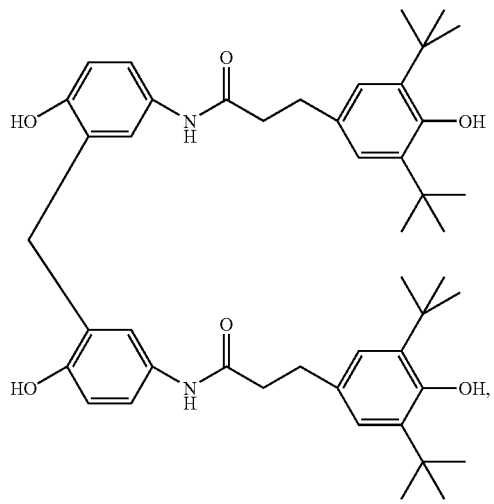 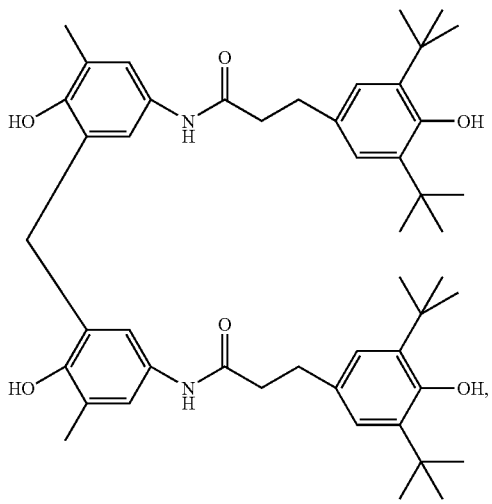
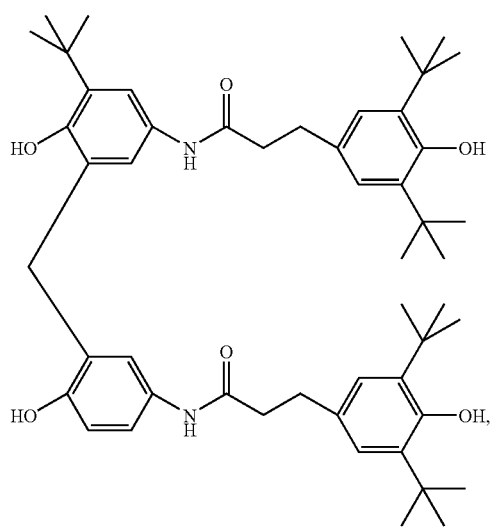 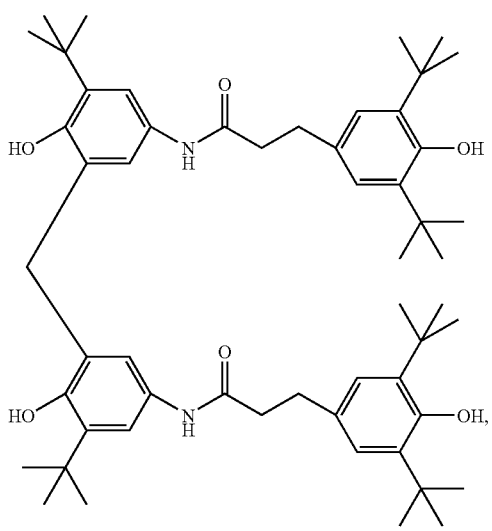
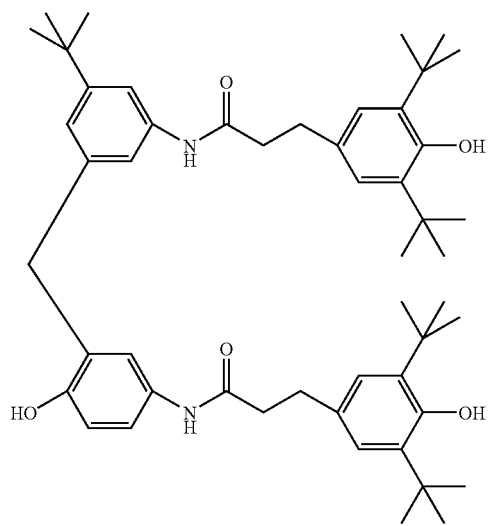 and 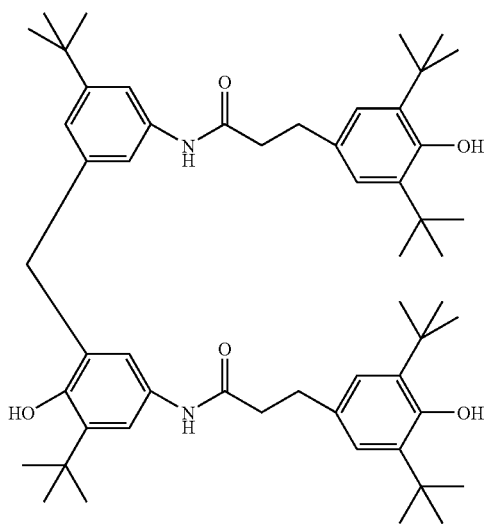

In a sixth embodiment of the present invention directed to a polymer represented by Structural Formula 2:

Z is —C(O)O—, —OC(O)—, —C(O)NH—, —NHC(O)—, —NH—, —O— or —C(O)—.

R' is —H.

Each R is independently an optionally substituted alkyl or optionally substituted alkoxycarbonyl.

Each R$_2$ is independently an optionally substituted alkyl or

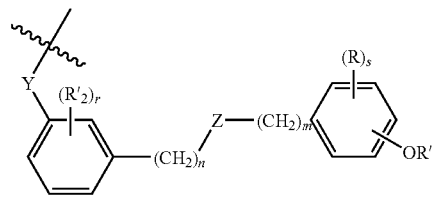

wherein at least one R$_2$ is

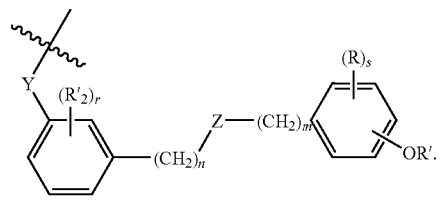

Each R'$_2$ is independently —M'—X, an optionally substituted alkyl or

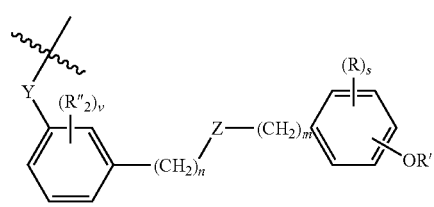

wherein at least one R'$_2$ is:

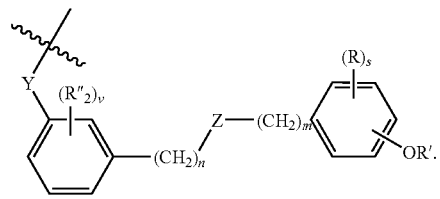

Each R"$_2$ is independently —M'—X, an optionally substituted alkyl or

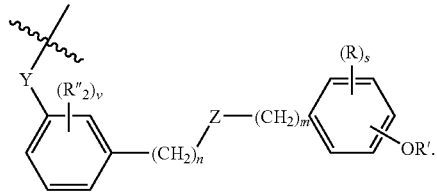

Each M' is independently —H or alkyl.

X is —O—.

Each Q is independently an optionally substituted C1-C10 alkylene group.

Each Q' is independently a bond or an optionally substituted C1-C10 alkylene group.

Each W is independently arylene, —O—, —S—, —NH—, —N(OH)—, —C(=N(OH))—, or a bond.

Each n and m are independently integers from 0 to 2.

Each s and v are independently integers from 0 to 2.

Each r and q are independently integers from 1 to 3, and the remainder of the variables are as described above in the first embodiment.

In a seventh embodiment of the present invention directed to a polymer represented by Structural Formula 2:

Z is —C(O)NH— or —NHC(O)—.

Each R is independently an alkyl or an alkoxycarbonyl.

s is 2, and the remainder of the variables are as described above in the sixth embodiment.

In an eighth embodiment of the present invention directed to a polymer represented by Structural Formula 2:

Each R is independently an alkyl group and the remainder of the variables are as described above in the seventh embodiment. In certain embodiments R is a bulky alkyl group. In certain embodiments the two R groups are bulky alkyl groups adjacent to the —OH group. In certain embodiments the two R groups are tert-butyl groups adjacent to the —OH group.

In a ninth embodiment of the present invention directed to a polymer represented by Structural Formula 2 the polymer comprises a repeat unit represented by the following Structural Formula:

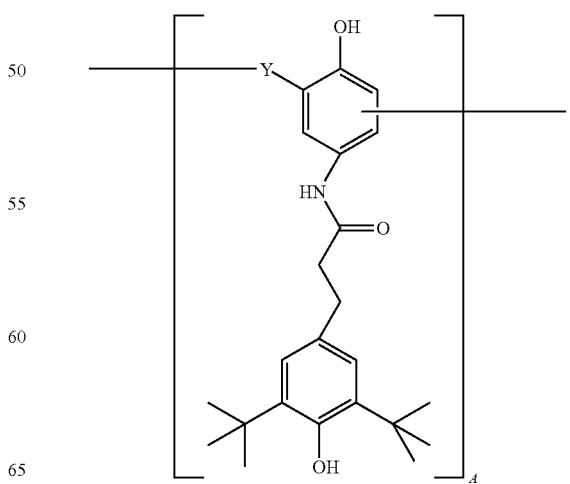

A is an integer of 3 or greater.

Y is —C(R")$_2$—, —(C(R")$_2$)$_p$-phenylene-(C(R")$_2$)$_p$— or —(C(R")$_2$)$_p$N(OH)(C(R")$_2$)$_p$.

Each R" is —H or alkyl. In certain embodiments R" is a linear or branched C1-C10 alkyl.

Each p is independently an integer of 1 to 5, and the remainder of the variables are as described above in the eighth embodiment.

In a tenth embodiment of the present invention directed to a polymer represented by Structural Formula 2:

Y is —CH$_2$, —CH$_2$N(OH)CH$_2$— or

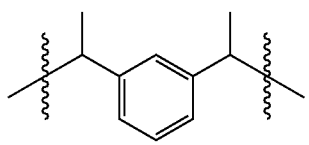

and the remainder of the variables are as described above in the ninth embodiment.

In an eleventh embodiment of the present invention directed to a polymer represented by Structural Formula 2 the polymer comprises repeat units represented by the following Structural Formulas:

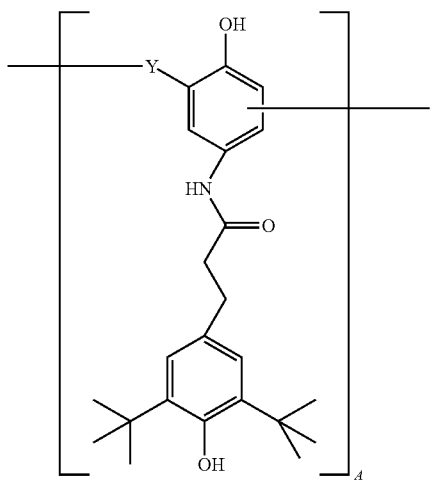

and

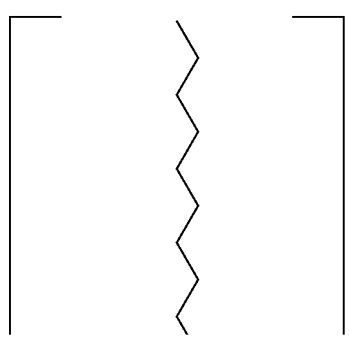

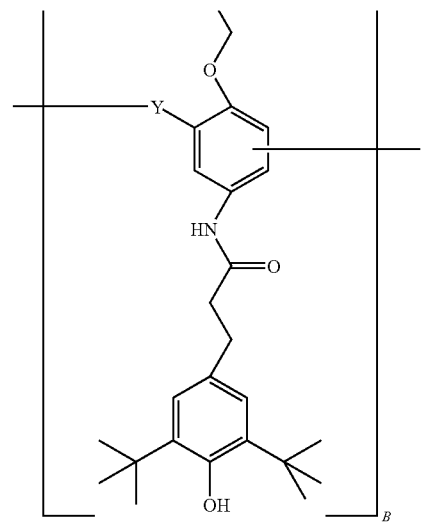

A and B are integers of 1 or greater and the sum of A and B is 3 or greater.

Y is —C(R")$_2$—, —(C(R")$_2$)$_p$-phenylene-(C(R")$_2$)$_p$— or —(C(R")$_2$)$_p$N(OH)(C(R")$_2$)$_p$.

Each R" is —H or alkyl.

Each p is independently an integer of 1 to 5, and the remainder of the variables are as described above in the eighth embodiment.

In a twelfth embodiment of the present invention directed to a polymer represented by Structural Formula 2:

Y is —CH$_2$, —CH$_2$N(OH)CH$_2$— or

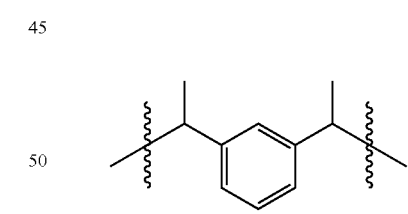

and the remainder of the variables are as described above in the eleventh embodiment.

In certain embodiments the molar ratios of A:B are 1:1, 1:2, 1:3, 1:4, 1: or 1:10. In certain embodiments the molar ratios are 1:1 or 1:2.

In an thirteenth embodiment of the present invention directed to a polymer represented by Structural Formula 2 the polymer comprises repeat units represented by the following Structural Formulas:

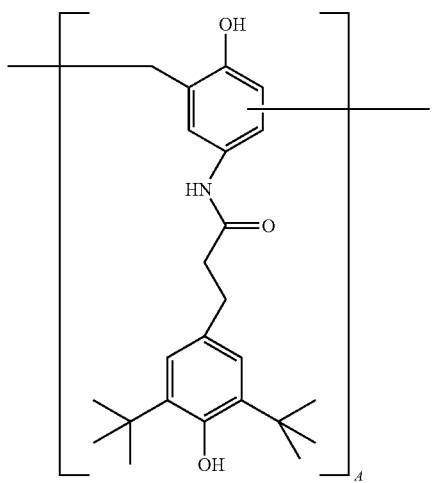

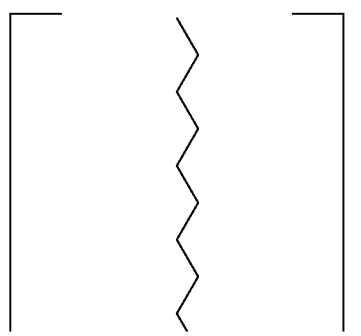

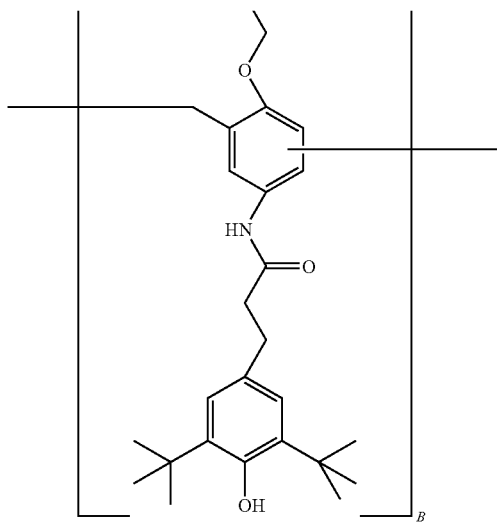

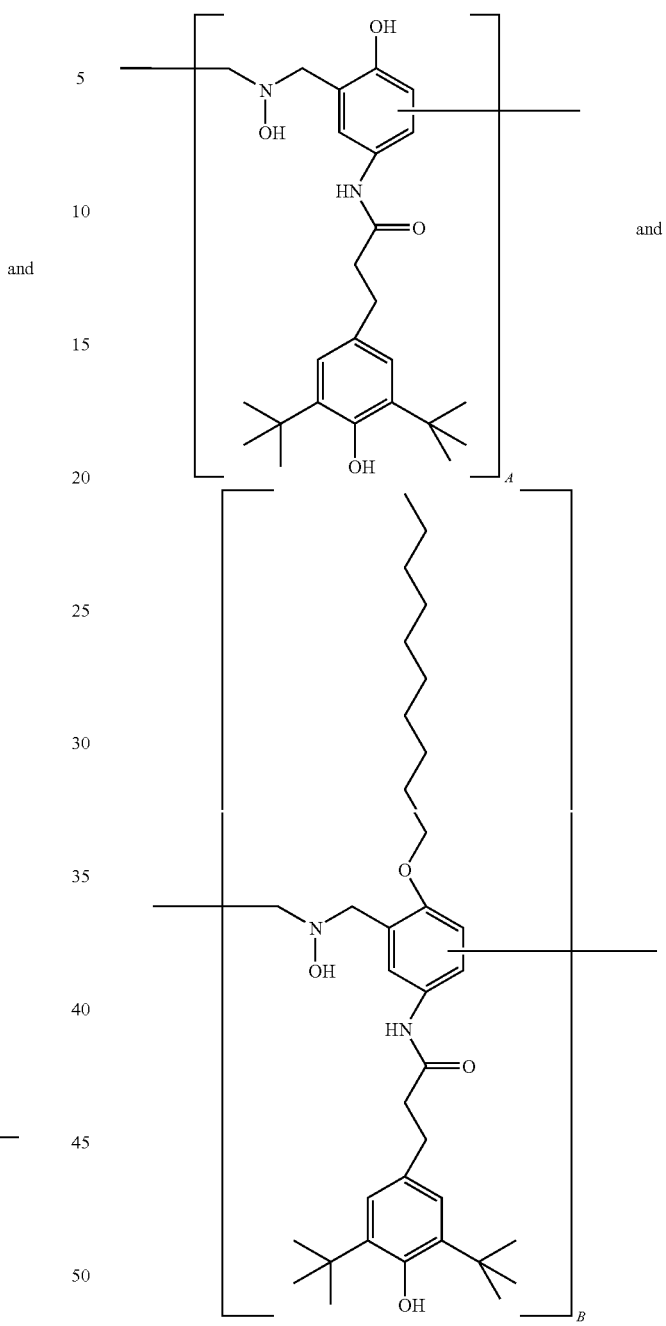

In an fourteenth embodiment of the present invention directed to a polymer represented by Structural Formula 2 the polymer comprises repeat units represented by the following Structural Formulas:

In certain embodiments, it is understood that where a repeat unit forms the end of a polymer chain the linking group Y is not present. In certain embodiments when a repeat unit form the end of a polymer chain the linking group Y can be replaced by an alkyl group such a methyl, ethyl, tert-butyl etc., i.e., an alkyl group which is meta to where the phenyl ring joins the rest of the molecule.

In another embodiment the present invention is directed to a composition comprising a compound represented by Structural Formula 1 and a compound represented by Structural Formula 3.

In a first embodiment for the composition comprising a compound represented by Structural Formula 1 and a compound represented by Structural Formula 3:

Each Z is —C(O)NR'—, —NR'C(O)—, —NR'—, —CR'=N—, —C(O)—, —C(O)O—, —OC(O)—, —O—, —S—, —C(O)OC(O)— or a bond.

Each R' is independently —H or optionally substituted alkyl.

Each R is independently an optionally substituted alkyl, optionally substituted aryl, optionally substituted alkoxycarbonyl, optionally substituted ester, —OH, —NH$_2$, —SH, or

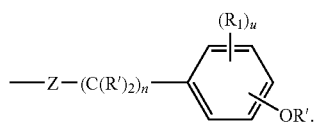

In certain embodiments at least one R adjacent to the —OH group is a bulky alkyl group (e.g., butyl, sec-butyl, tert-butyl, 2-propyl, 1,1-dimethylhexyl, and the like). In certain other embodiments both R groups adjacent to —OH are bulky alkyl groups (e.g., butyl, sec-butyl, tert-butyl, 2-propyl, 1,1-dimethylhexyl, and the like). In another embodiment, both R groups are tert-butyl. In another embodiment, both R groups are tert-butyl adjacent to the OH group.

Each $R_1$ is independently an optionally substituted alkyl, optionally substituted aryl, optionally substituted alkoxycarbonyl, optionally substituted ester, —OH, —NH$_2$ or —SH. In certain embodiments at least one $R_1$ adjacent to the —OH group is a bulky alkyl group (e.g., butyl, sec-butyl, tert-butyl, 2-propyl, 1,1-dimethylhexyl, and the like). In certain other embodiments both $R_1$ groups adjacent to —OH are bulky alkyl groups (e.g., butyl, sec-butyl, tert-butyl, 2-propyl, 1,1-dimethylhexyl, and the like). In another embodiment, both $R_1$ groups are tert-butyl. In another embodiment, both $R_1$ groups are tert-butyl adjacent to the OH group.

Each $R_2$ is independently an optionally substituted alkyl, optionally substituted aryl, optionally substituted alkoxycarbonyl, optionally substituted ester, —OH, —NH$_2$ or —SH.

Each X is —C(O)O—, —OC(O)—, —C(O)NR'—, —NR'C(O)—, —NR'—, —CH=N—, —C(O)—, —O—, —S—, —NR'— or —C(O)OC(O)—. Optionally an additional values for X is a bond.

M is an alkyl or

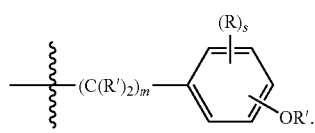

M' is a —H, alkyl or

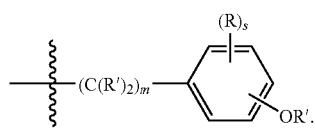

Each n and m are independently integers from 0 to 6.

Each s, q and u are independently integers from 0 to 4.

In a second embodiment for the composition comprising a compound represented by Structural Formula 1 and a compound represented by Structural Formula 3:

Each Z is —C(O)O—, —OC(O)—, —C(O)NH—, —NHC(O)—, —NH—, —O— or —C(O)—.

R' is —H.

Each R is independently an optionally substituted alkyl or optionally substituted alkoxycarbonyl.

Each $R_2$ is independently an optionally substituted alkyl.

X is —O—.

M is an alkyl. In certain embodiments M is a C1-C20 alkyl.

M' is —H or alkyl. In certain embodiments M' is —H or C1-C20 alkyl.

Each n and m are independently integers from 0 to 2.

Each s and q are independently integers from 0 to 2, and the remainder of the variables are as described above for the first embodiment.

In a third embodiment for the composition comprising a compound represented by Structural Formula 1 and a compound represented by Structural Formula 3:

Z is —C(O)NH— or —NHC(O)—.

Each R is independently an alkyl or an alkoxycarbonyl.

Each $R_2$ is independently an alkyl.

s is 2, and the remainder of the variables are as described above for the second embodiment.

In a fourth embodiment for the composition comprising a compound represented by Structural Formula 1 and a compound represented by Structural Formula 3:

Each R is independently an alkyl group, and the remainder of the variables are as described above for the third embodiment. In certain embodiments R is a bulky alkyl group. In certain embodiments the two R groups are bulky alkyl groups adjacent to the —OH group. In certain embodiments the two R groups are tert-butyl groups adjacent to the —OH group.

In a fifth embodiment for the composition comprising a compound represented by Structural Formula 1 as described above and a compound represented by Structural Formula 3 the compound represented by Structural Formula 1 is represented by the following Structural Formula:

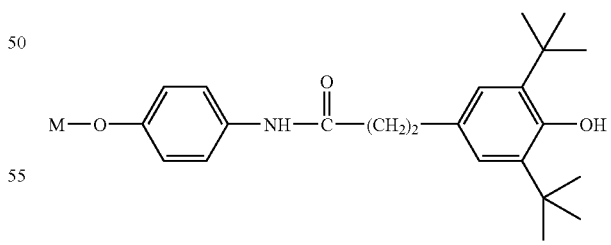

M is a C1 to C20 linear or branched alkyl chain, and the remainder of the variables are as described above for the fourth embodiment.

In a sixth embodiment for the composition comprising a compound represented by Structural Formula 1 as described above and a compound represented by Structural Formula 3 the compound represented by Structural Formula 1 is represented a Structural Formula selected from:

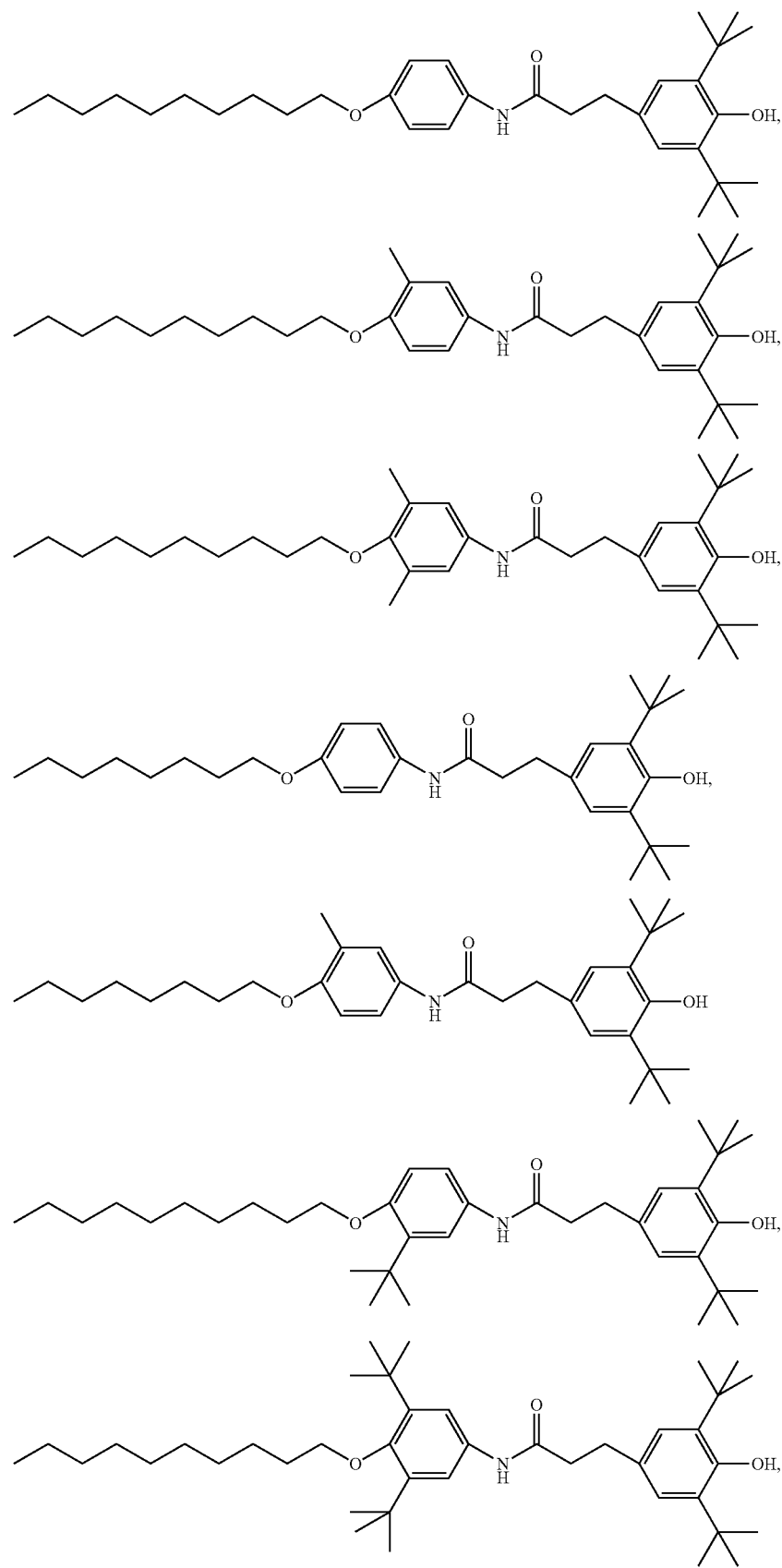

-continued
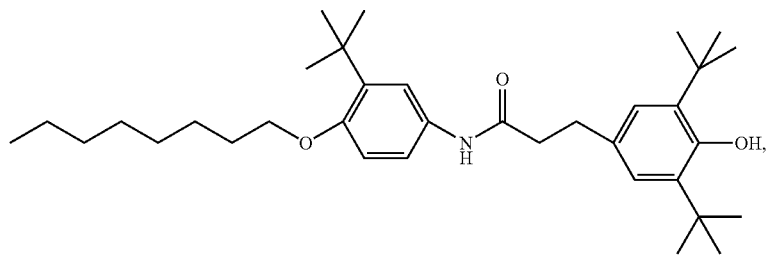
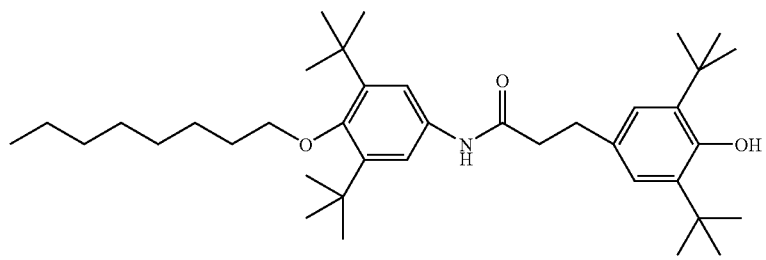
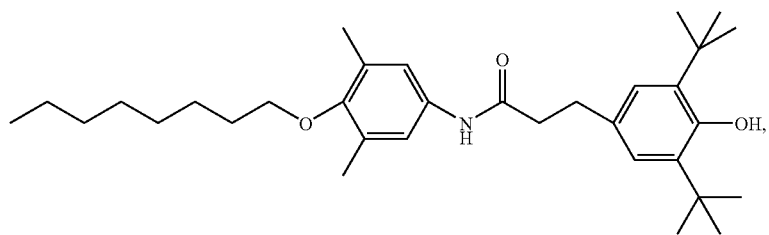
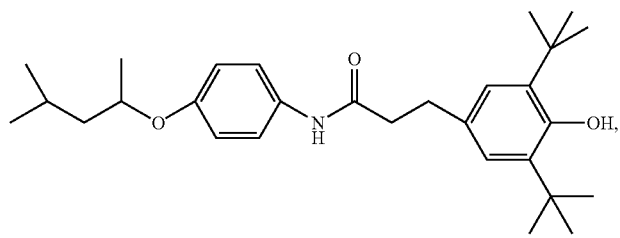
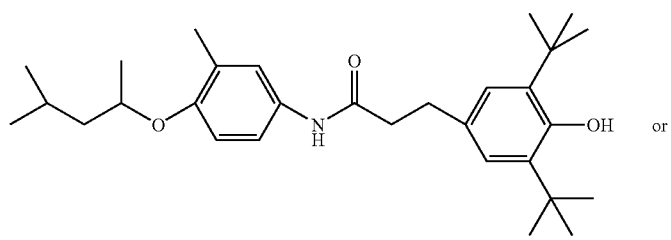 or
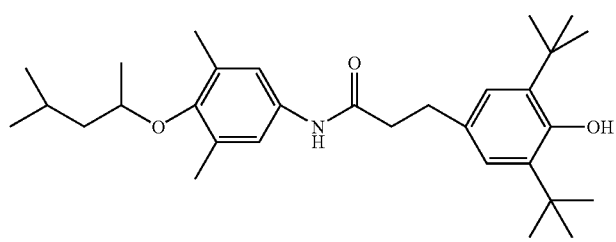

In a seventh embodiment for the composition comprising a compound represented by Structural Formula 1 and a compound represented by Structural Formula 3 the compound represented by Structural Formula 3 is represented a Structural Formula selected from:

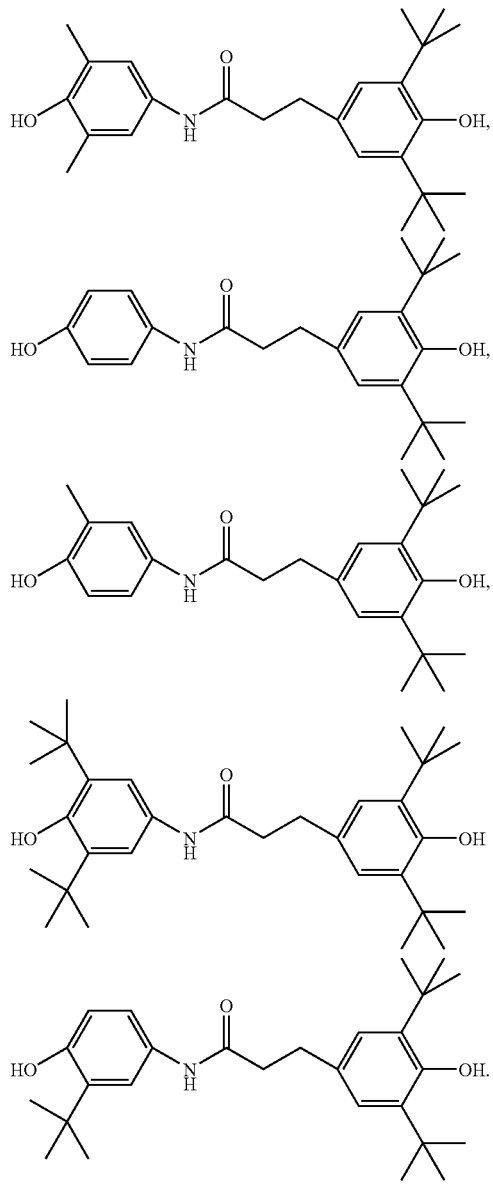

In an eighth embodiment for the composition comprising a compound represented by Structural Formula 1 and a compound represented by Structural Formula 3 the weight:weight ratio of compound 1:compound 3 is 1:1, 1:2, 1:3, 1:5 or 1:10.

In an eighth embodiment for the composition comprising a compound represented by Structural Formula 1 and a compound represented by Structural Formula 3 the weight:weight ratio of compound 1:compound 3 is 1:2.

In a ninth embodiment of the present invention the composition comprising a compound represented by Structural Formula 1 and a compound represented by Structural Formula 3 is represented as follows:

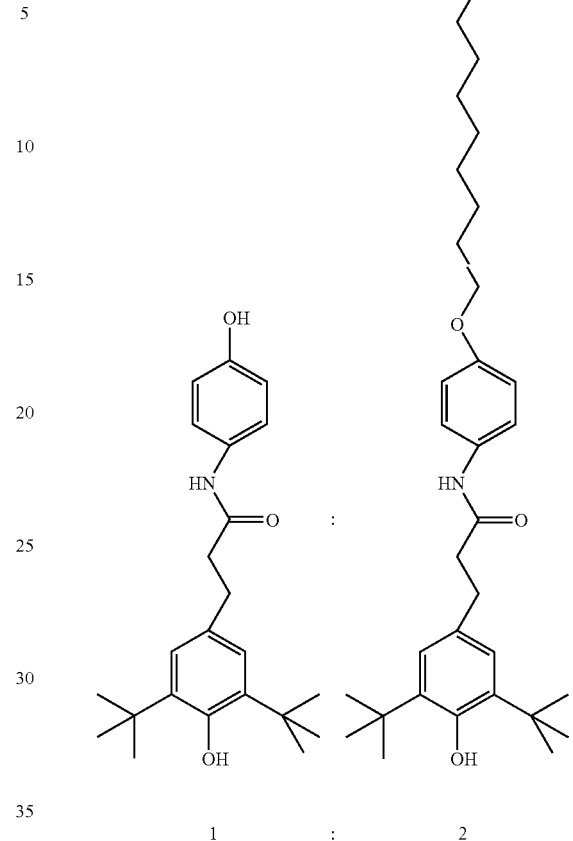

In particular, the present invention pertains to novel and effective alkylated antioxidant macromolecules having formula I:

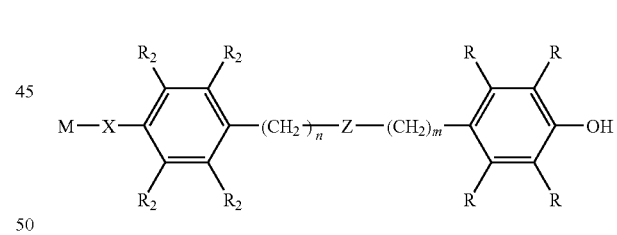

wherein, independently for each occurrence,
n and m are integers from 0 to 6, inclusive;
Z is —C(O)O—, —OC(O)—, —C(O)NH—, —NHC(O)—, —NH—, —CH=N—, —C(O)—, —O—, —S—, —C(O)OC(O)—, or a bond;
R is H, $C_{1-6}$ alkyl, —OH, —NH$_2$, —SH, aryl, ester, or

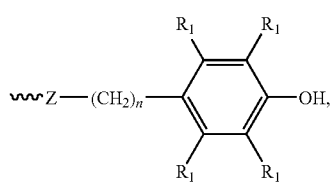

wherein at least one R adjacent to the —OH group is a bulky alkyl group (e.g., butyl, sec-butyl, tert-butyl, 2-propyl, 1,1-dimethylhexyl, and the like);

$R_1$ is H, $C_{1-6}$ alkyl, aryl, aralkyl, —OH, —NH$_2$, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like); and $R_2$ is H, $C_{1-6}$ alkyl, aryl, aralkyl, —OH, —NH$_2$, —SH, or ester, wherein at least one $R_1$ adjacent to the —OH group is a bulky alkyl group (e.g., butyl, sec-butyl, tert-butyl, 2-propyl, 1,1-dimethylhexyl, and the like);

X is —C(O)O—, —OC(O)—, —C(O)NH—, —NHC(O)—, —NH—, —CH=N—, —C(O)—, —O—, —S—, —C(O)OC(O)—, or a bond;

M is H, aryl, C-1 to C-20 linear or branched alkyl chain with or without any functional group anywhere in the chain, or

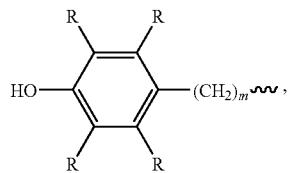

wherein m and each R is independently as described above; wherein $R_2$ is H, $C_{1-6}$ alkyl, —OH, —NH$_2$, —SH, aryl, ester, or

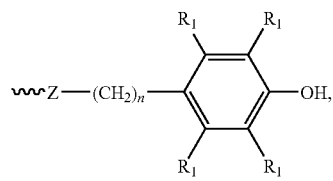

wherein at least one $R_2$ is —OH and n, Z, and each R1 are independently as described above.

In various embodiments, the present invention relates to a compound of formula I and the attendant definitions, wherein Z is —OC(O)—. In another embodiment, Z is —C(O)O—. In another embodiment, Z is —C(O)NH—. In another embodiment, Z is —NHC(O)—. In another embodiment, Z is —NH—. In another embodiment, Z is —CH=N—. In another embodiment, Z is —C(O)—. In another embodiment, Z is —O—. In another embodiment, Z is —C(O)OC(O)—. In another embodiment, Z is a bond.

In another embodiment, the present invention relates to a compound of formula I and the attendant definitions, wherein both R groups adjacent to —OH are bulky alkyl groups (e.g., butyl, sec-butyl, tert-butyl, 2-propyl, 1,1-dimethylhexyl, and the like). In another embodiment, both R groups are tert-butyl.

In another embodiment, the present invention relates to a compound of formula I and the attendant definitions, wherein M is

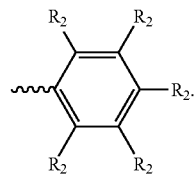

In another embodiment, the present invention relates to a compound of formula I and the attendant definitions, wherein at least one R is

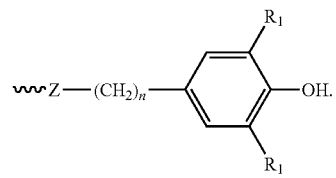

In another embodiment, the present invention relates to a compound of formula I and the attendant definitions, wherein n is 0.

In another embodiment, the present invention relates to a compound of formula I and the attendant definitions, wherein m is 1.

In another embodiment, the present invention relates to a compound of formula I and the attendant definitions, wherein n is 0 and m is 1.

In another embodiment, the present invention relates to a compound of formula I and the attendant definitions, wherein n is 0, m is 1, and Z is —C(O)O—.

In another embodiment, the present invention relates to a compound of formula I and the attendant definitions, wherein n is 0, m is 1, Z is —C(O)O—, and the two R groups adjacent to the OH are tert-butyl.

In another embodiment, the present invention relates to a compound of formula I and the attendant definitions, wherein n is 0, m is 1, Z is —C(O)O—, the two R groups adjacent to the OH are t-butyl, and M is

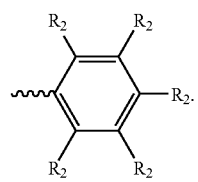

In another embodiment, the present invention relates to a compound of formula I and the attendant definitions, wherein n is 0, m is 1, Z is —C(O)O—, the two R groups adjacent to the OH are t-butyl, M is

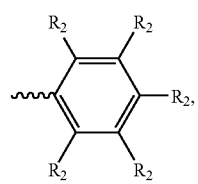

and the $R_2$ in the para position is OH.

In another embodiment, the present invention relates to a compound of formula I and the attendant definitions, wherein n is 0, m is 1, Z is —C(O)O—, the two R groups adjacent to the OH are t-butyl, M is

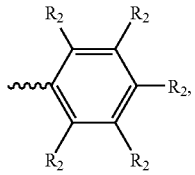

the R$_2$ in the para position is OH, and an adjacent R$_2$ is OH.

In another embodiment, the present invention relates to a compound of formula I and the attendant definitions, wherein n is 0, m is 1, Z is —C(O)O—, the two R groups adjacent to the OH are t-butyl, M is

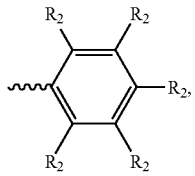

the R$_2$ in the para position is OH, and the two adjacent R$_2$ groups are —OH.

In some embodiments, the present invention relates to compounds that are alkylated macromolecular antioxidants of the formula III.

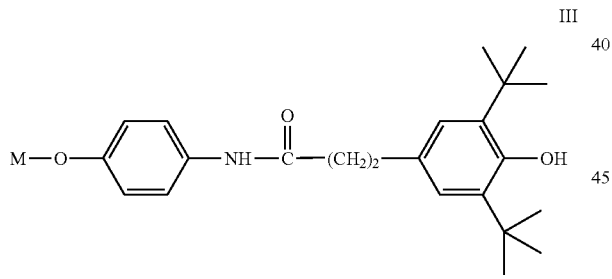

where M is C1 to C20-linear or branched alkyl chains. The compounds of formula III can have antioxidant properties.

In certain embodiments the present invention relates to a compound represented by Structural Formula I:

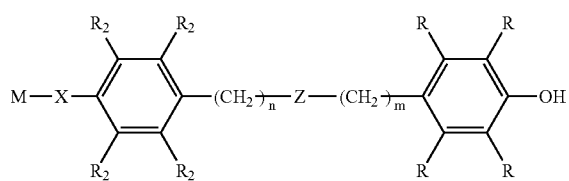

wherein, independently for each occurrence, n and m are integers from 0 to 6, inclusive;

Z is —C(O)O—, —OC(O)—, —C(O)NH—, —NHC(O)—, —NH—, —CH═N—, —C(O)—, —O—, —S—, —C(O)OC(O)—, or a bond;

R is H, C$_{1-6}$ alkyl, —OH, —NH$_2$, —SH, aryl, ester, or

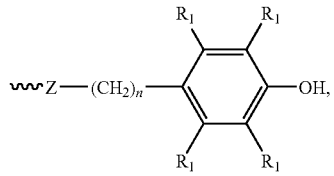

wherein at least one R adjacent to the —OH group is a bulky alkyl group (e.g., butyl, sec-butyl, tert-butyl, 2-propyl, 1,1-dimethylhexyl, and the like);

R$_1$ is H, C$_{1-6}$ alkyl, aryl, aralkyl, —OH, —NH$_2$, —SH, or C1-C6 alkyl ester wherein at least one R$_1$ adjacent to the —OH group is a bulky alkyl group (e.g., butyl, sec-butyl, tert-butyl, 2-propyl, 1,1-dimethylhexyl, and the like); and R$_2$ is H, C$_{1-6}$ alkyl, aryl, aralkyl, —OH, —NH$_2$, —SH, or ester, wherein at least one R$_1$ adjacent to the —OH group is a bulky alkyl group (e.g., butyl, sec-butyl, tert-butyl, 2-propyl, 1,1-dimethylhexyl, and the like);

X is —C(O)O—, —OC(O)—, —C(O)NH—, —NHC(O)—, —NH—, —CH═N—, —C(O)—, —O—, —S—, —C(O)OC(O)—, or a bond;

M is H, aryl, C-1 to C-20 linear or branched alkyl chain with or without any functional group anywhere in the chain, or

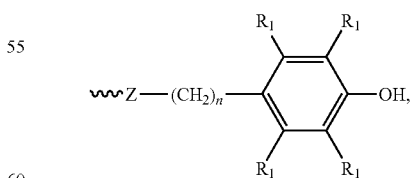

wherein m and each R is independently as described above;

wherein

R$_2$ is H, C$_{1-6}$ alkyl, —OH, —NH$_2$, —SH, aryl, ester, or

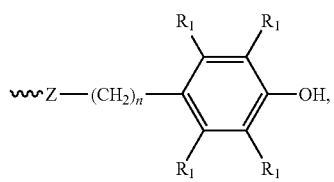

wherein at least one R$_2$ is —OH and n, Z, and each R1 are independently as described above.

In certain embodiments the present invention relates to a compound represented by Structural Formula I wherein Z is —OC(O)—.

In certain embodiments the present invention relates to a compound represented by Structural Formula I wherein Z is —C(O)O—.

In certain embodiments the present invention relates to a compound represented by Structural Formula I wherein Z is —C(O)NH—.

In certain embodiments the present invention relates to a compound represented by Structural Formula I wherein Z is —NHC(O)—.

In certain embodiments the present invention relates to a compound represented by Structural Formula I wherein Z is —NH—.

In certain embodiments the present invention relates to a compound represented by Structural Formula I wherein Z is —CH=N—.

In certain embodiments the present invention relates to a compound represented by Structural Formula I wherein Z is —C(O)—.

In certain embodiments the present invention relates to a compound represented by Structural Formula I wherein Z is —O—.

In certain embodiments the present invention relates to a compound represented by Structural Formula I wherein Z is —C(O)OC(O)—.

In certain embodiments the present invention relates to a compound represented by Structural Formula I wherein Z is a bond.

In certain embodiments the present invention relates to a compound represented by Structural Formula I wherein the R groups adjacent to —OH are both bulky alkyl groups.

In certain embodiments the present invention relates to a compound represented by Structural Formula I wherein the R groups adjacent to —OH are both tert-butyl.

In certain embodiments the present invention relates to a compound represented by Structural Formula I wherein M is

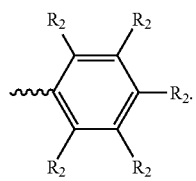

In certain embodiments the present invention relates to a compound represented by Structural Formula I wherein at least one R is

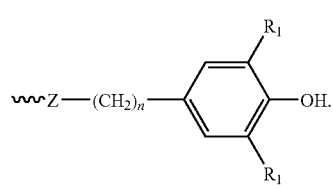

In certain embodiments the present invention relates to a compound represented by Structural Formula I wherein n is 0.

In certain embodiments the present invention relates to a compound represented by Structural Formula I wherein m is 1.

In certain embodiments the present invention relates to a compound represented by Structural Formula I wherein n is 0.

In certain embodiments the present invention relates to a compound represented by Structural Formula I wherein Z is —C(O)O—, wherein the R groups adjacent to —OH are both tert-butyl, wherein M is

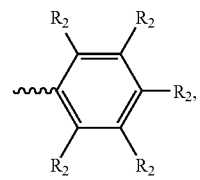

wherein the $R_2$ in the para position of the

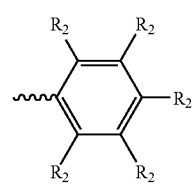

represented by M is —OH, wherein the $R_2$ adjacent to the $R_2$ in the para position of the

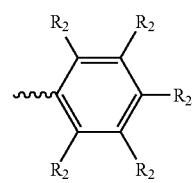

represented by M are —OH.

In certain embodiments the present invention relates to a compound represented by Structural Formula I wherein the compound is represented by Structural Formula III:

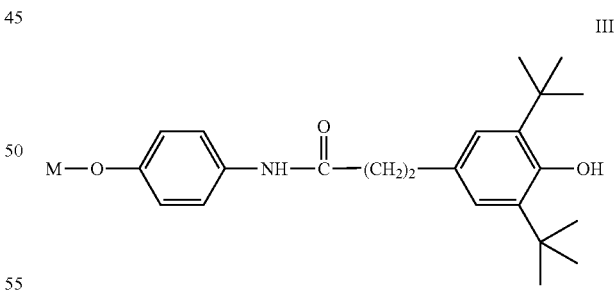

where M is a C1 to C20-linear or branched alkyl chain.

The term "alkyl" as used herein means a saturated straight-chain, branched or cyclic hydrocarbon. When straight-chained or branched, an alkyl group is typically C1-C20, more typically C1-C10; when cyclic, an alkyl group is typically C3-C12, more typically C3-C7. Examples of alkyl groups include methyl, ethyl, n-propyl, iso-propyl, n-butyl, sec-butyl and tert-butyl and 1,1-dimethylhexyl.

The term "alkoxy" as used herein is represented by —OR, wherein R is an alkyl group as defined above.

The term "carbonyl" as used herein is represented by —C(=O)R, wherein R is an alkyl group as defined above.

The term "alkoxycarbonyl" as used herein is represented by —C(=O)OR, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

An "arylene" group as defined herein is a bivalent group represented by —Ar—, wherein Ar is an aromatic group as defined above.

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or contain one or more units of unsaturation. Examples of heterocyclic groups include piperidinyl, piperizinyl, pyrrolidinyl, pyrazolidinyl, imidazolidinyl, tetrahydroquinolinyl, inodolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below. Preferably the nitrogen is unsubstituted.

As used herein the term non-aromatic carbocyclic ring as used alone or as part of a larger moiety refers to a non-aromatic carbon containing ring which can be saturated or contain one or more units of unsaturation, having three to fourteen atoms including monocyclic and polycyclic rings in which the carbocyclic ring can be fused to one or more non-aromatic carbocyclic or heterocyclic rings or one or more aromatic (carbocyclic or heterocyclic) rings An optionally substituted aryl group as defined herein may contain one or more substitutable ring atoms, such as carbon or nitrogen ring atoms. Examples of suitable substituents on a substitutable ring carbon atom of an aryl group include halogen (e.g., —Br, Cl, I and F), —OH, C1-C4 alkyl, C1-C4 haloalkyl, —NO$_2$, C1-C4 alkoxy, C1-C4 haloalkoxy, —CN, —NH$_2$, C1-C4 alkylamino, C1-C4 dialkylamino, —C(O)NH$_2$, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)$_2$, —NHC(O)O—(C1-C4 alkyl), —C(O)OH, —C(O)O—(C1-C4 alkyl), —NHC(O)NH$_2$, —NHC(O)NH(C1-C4 alkyl), —NHC(O)N(C1-C4 alkyl)$_2$, —NH—C(=NH)NH$_2$, —SO$_2$NH$_2$—SO$_2$NH(C1-C3 alkyl), —SO$_2$N(C1-C3 alkyl)$_2$, NHSO$_2$H, NHSO$_2$(C1-C4 alkyl) and aryl. Preferred substituents on aryl groups are as defined throughout the specification. In certain embodiments aryl groups are unsubstituted.

Examples of suitable substituents on a substitutable ring nitrogen atom of an aryl group include C1-C4 alkyl, NH$_2$, C1-C4 alkylamino, C1-C4 dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3 alkyl), —SO$_2$N(C1-C3 alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, An optionally substituted alkyl group or non-aromatic carbocyclic or heterocyclic group as defined herein may contain one or more substituents. Examples of suitable substituents for an alkyl group include those listed above for a substitutable carbon of an aryl and the following: =O, =S, =NNHR, =NN(R)$_2$, =NNHC(O)R, =NNHCO$_2$(alkyl), =NNHSO$_2$(alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

In yet another embodiment, the present invention is a method of producing a compound or a polymer described herein using methods know in the art of organic and polymer chemistry.

In certain embodiments this invention can allow synthesizing macromolecular antioxidants cost effectively. In these embodiments these methods also reports an improved, highly efficient and economical process for the synthesis of alkylated macromolecular antioxidants.

In various embodiments, the alkylated macromolecular antioxidants of the present invention can be prepared by the modification of compounds represented by the following Structural Formula:

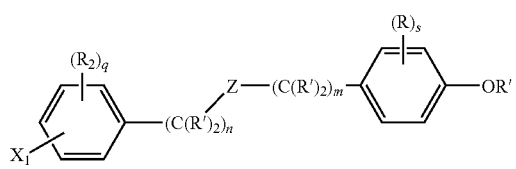

wherein $X_1$ is —C(O)OH, —OH, —NH$_2$ or —SH and the remainder of the variables are as described above.

In various embodiments, the alkylated macromolecular antioxidants of the present invention can be prepared as shown in the following Scheme:

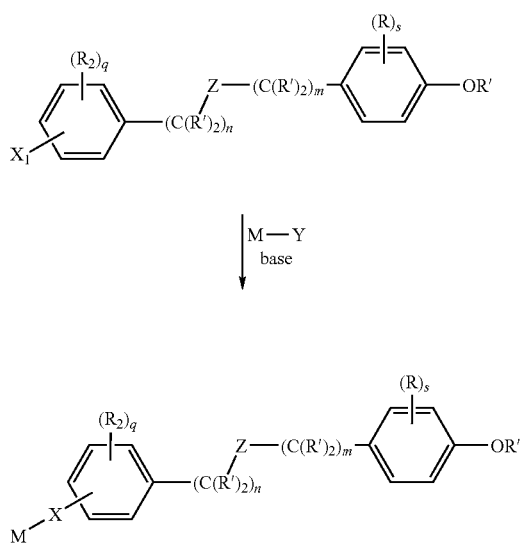

where Y is halogen (Cl, Br, or I) and M—Y can be dimethyl sulphate and the remainder of the variables are as described above.

In various embodiments, the alkylated macromolecular antioxidants of the present invention can be prepared as shown in the following Scheme:

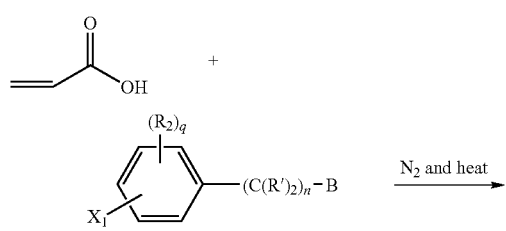

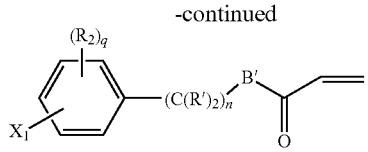

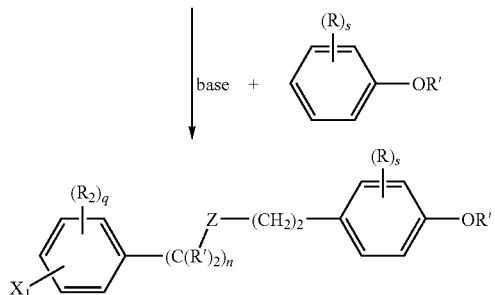

where Y is halogen (Cl, Br, or I), B is —NH$_2$, —OH etc., B' is —NH—, —O— etc., which together with =C(O)— forms Z, and the remainder of the variables are as described above.

In various embodiments, the alkylated macromolecular antioxidants of the present invention can be prepared as shown in the following Scheme:

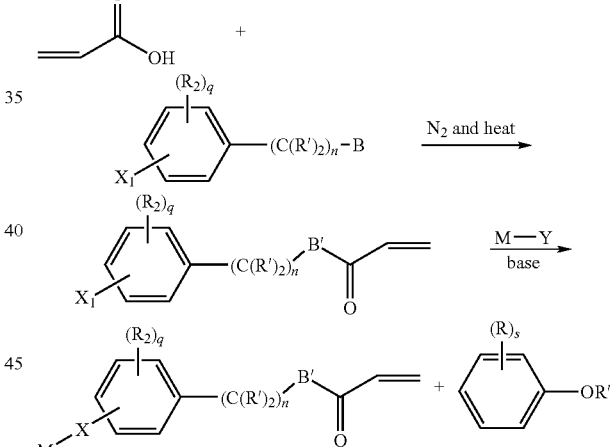

where Y is halogen (Cl, Br, or I), B is —NH$_2$, —OH etc., B' is —NH—, —O— etc., which together with =C(O)— forms Z, and the remainder of the variables are as described above.

In various embodiments, the alkylated macromolecular antioxidants of the present invention can be prepared as shown in the following Scheme:

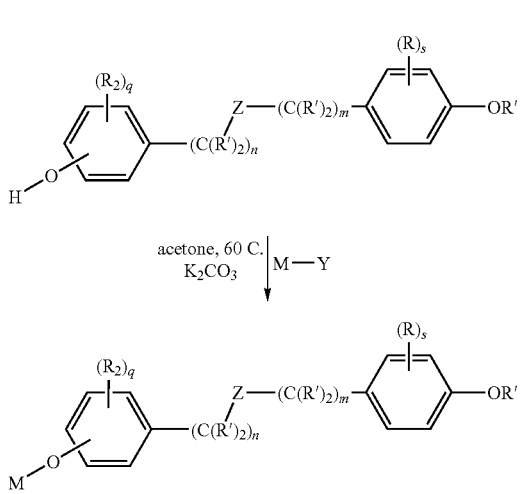

acetone, 60 C. | M—Y
K₂CO₃ where Y is halogen (Cl, Br, or I) and the remainder of the variables are as described above.

In certain embodiments the compounds are made by, for example, dissolving the phenolic starting material in a suitable solvent, such as, for example, acetone, and adding for example potassium carbonate. In these embodiments the mixture is stirred and a haloalkane for example bromodecane added, over a period of time for example 1 min to 24 hours, 10 minutes to 15 hours, 30 minutes to 2 hours, or 55 minutes to 65 minutes. In these embodiments the mixture is then refluxed and progress of the reaction is monitored by thin layer chromatography. After completion of the reaction, potassium carbonate is filtered and the solvent is removed under vacuum to get the crude solid. The solid is obtained was re-dissolved in hexane and filtered to obtain the pure solid.

In various embodiments, the alkylated macromolecular antioxidants of the present invention can be prepared as shown in the following Scheme:

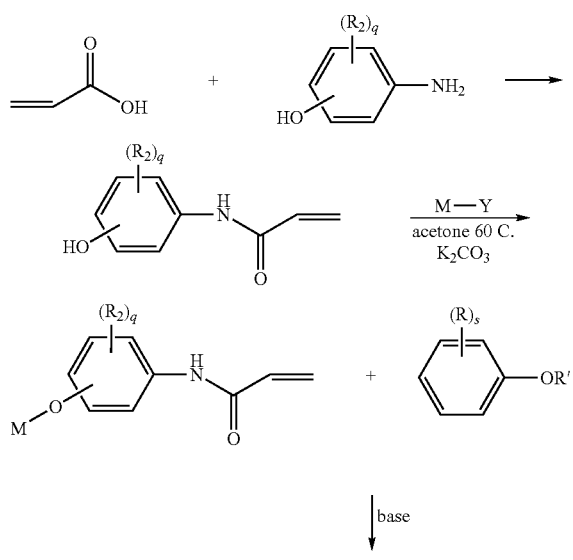

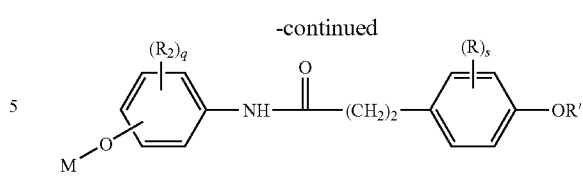

where Y is halogen (Cl, Br, or I) and the remainder of the variables are as described above.

In various embodiments, intermediates in the compounds of the present invention can be prepared by methods described in U.S. Publication No.s: 2006/0041094 and 2006/0041087 U.S. application Ser. No.s: 11/292,813, 11/293,050, 11/293,049 and 11/293,844 the entire teachings of each of these references are incorporated herein by reference. In various embodiments, compounds represented by Structural Formula 3 can be prepared by methods described in U.S. Publication No.s: 2006/0041094 and 2006/0041087 U.S. application Ser. No.s: 11/292,813, 11/293,050, 11/293,049 and 11/293,844 the entire teachings of each of these references are incorporated herein by reference.

The compositions comprising a compound of Structural Formula 1 and a compound of Structural Formula 2 are prepared in certain embodiments by physically mixing the two compounds in certain ratios using a vortex mixture. The compositions comprising a compound of Structural Formula 1 and a compound of Structural Formula 2 are prepared in certain embodiments by dissolving the compounds in an organic solvent, homogenizing it and removing the organic solvent. Suitable organic solvents are any solvents known in the art in which the compounds can be dissolved or suspended. The compounds can be mixed or dissolved under a range of temperatures including from 0 to 100° C., from 10 to 50° C. or from 15 to 30° C. The temperature at which the compounds are mixed will vary depending on the starting material, for example, powder starting material can be physically mixed at room temperature, alternatively powder or liquid starting material can be heated to dissolve in suitable solvents.

In various embodiments, the alkylated macromolecular antioxidants of formula I can be prepared by the modification of the compounds of formula II.

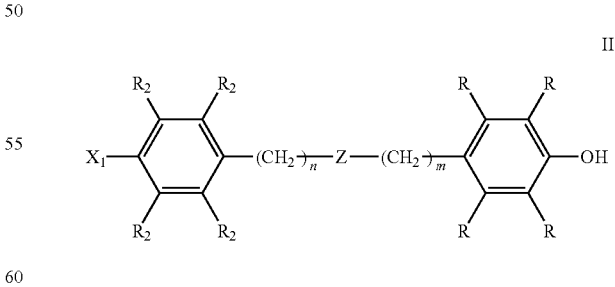

wherein, independently for each occurrence, n and m are integers from 0 to 6, inclusive;

Z is —C(O)O—, —OC(O)—, —C(O)NH—, —NHC(O)—, —NH—, —CH=N—, —C(O)—, —O—, —S—, —C(O)OC(O)—, or a bond;

R is H, $C_{1-6}$ alkyl, —OH, —NH₂, —SH, aryl, ester, or

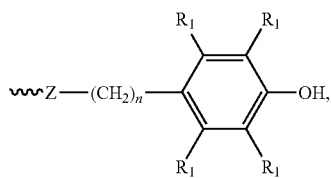

wherein at least one R adjacent to the —OH group is a bulky alkyl group;

R$_1$ is H, C$_{1-6}$ alkyl, aryl, aralkyl, —OH, —NH$_2$, —SH, or ester wherein at least one R$_1$ adjacent to the —OH group is a bulky alkyl group; and R$_2$ is H, C$_{1-6}$ alkyl, aryl, aralkyl, —OH, —NH$_2$, —SH, or ester wherein at least one R$_1$ adjacent to the —OH group is a bulky alkyl group;

X$_1$ is —C(O)OH, —OH, —NH$_2$, CHO, —SH, or C1-C6 alkyl ester.

In various embodiments, the compounds of formula I can be prepared by the modification of compound of formula II as shown in Scheme-2.

Scheme-2

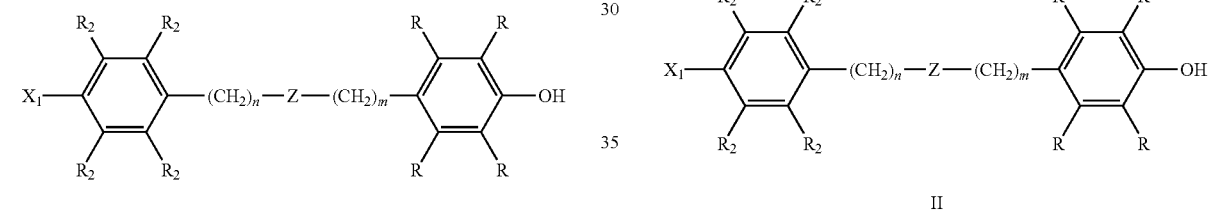

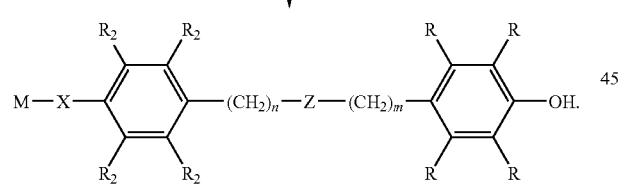

In various embodiments, the compounds of formula II can be prepared by methods described in U.S. Provisional Application No. 60/590,575, filed Jul. 23, 2004, Title: Antioxidant Macromonomers and Polymers and methods of making and using the same; U.S. Provisional Application No. 60/590,646, filed Jul. 23, 2004; Title: Antioxidant Macromonomers and Polymers and methods of making and using the same; Ser. No. 60/632,893, U.S. Provisional Application filed Dec. 3, 2004; Ser. No. 60/633,252 U.S. Provisional Application filed Dec. 3, 2004, Title: ONE POT PROCESS FOR MAKING POLYMERIC ANTIOXIDANTS by Kumar, et al. The entire teachings of these references are incorporated herein by reference.

In various embodiments, the compounds of formula II can also be prepared by the method shown in Scheme 1.

Scheme-1

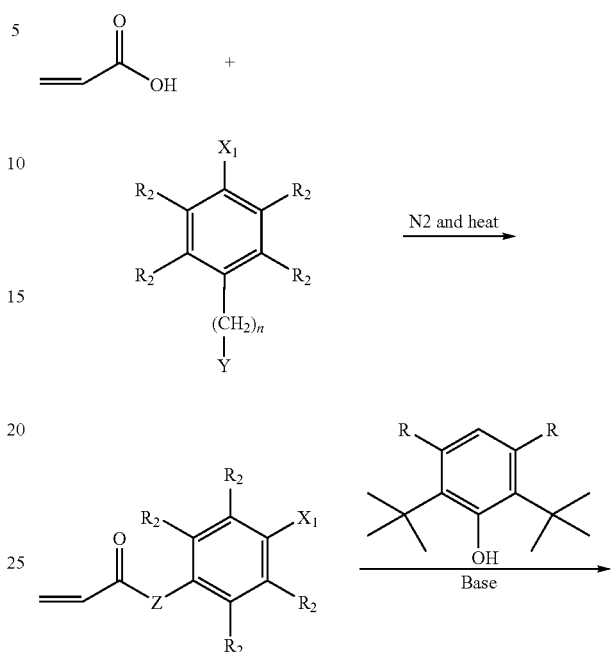

II

In various embodiments, the compounds of formula II can also be prepared by the method shown in scheme-3

Scheme-3

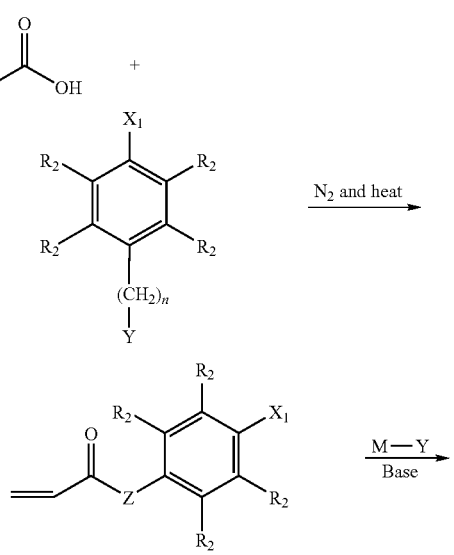

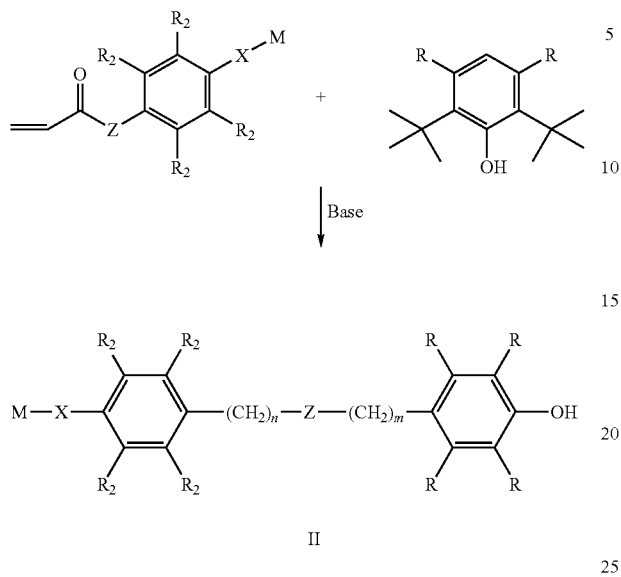
In various embodiments, the compounds of formula III can be prepared by a method shown in scheme 4 or scheme 5:
Scheme 4
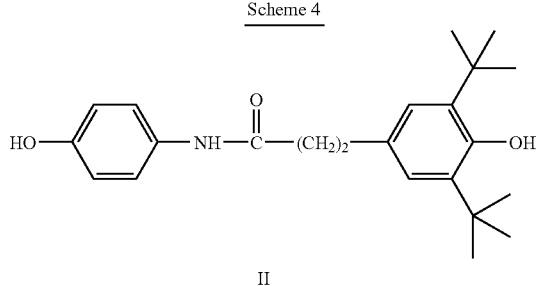
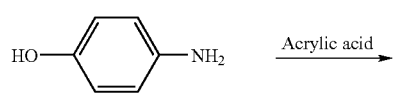
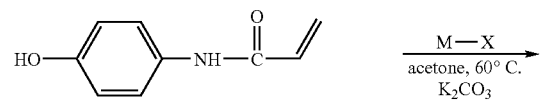
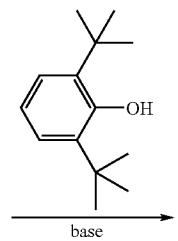
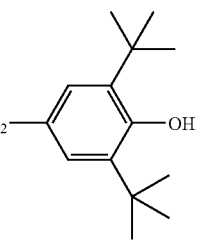
III
Where M is C1-C20 long linear or branched alkyl chains, and X is a halogen Cl, Br or I.
In various embodiments, the polymers of the present invention can be prepared as shown in the following Scheme:
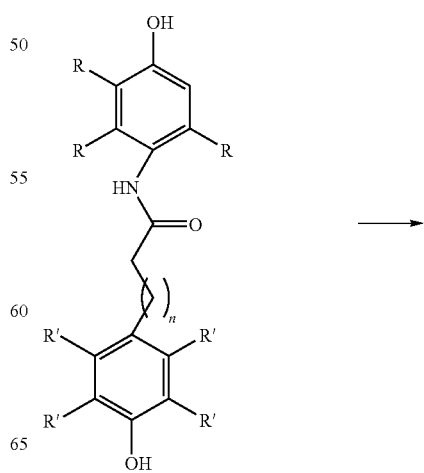

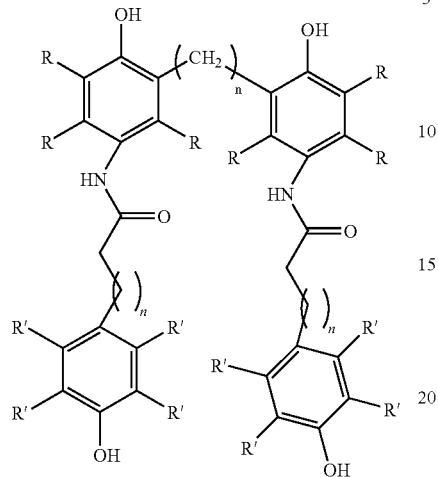

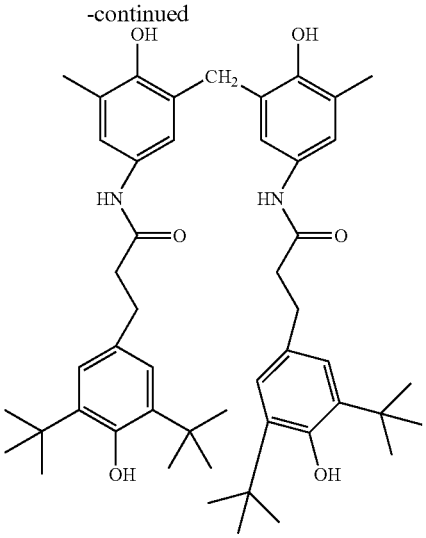

In various embodiments, the polymers of the present invention can be prepared as shown in the following Scheme:

In certain embodiments the present invention is a method of making the polymers of the present invention comprising the steps of dissolving or suspending the starting material in a suitable solvent, such as, methanol or ethanol; adding a suitable reagent, such as, an aldehyde, for example, paraformaldehyde under suitable acidic conditions, such as, for example in the presence of hydrochloric acid. The mixture of the starting material, solvent acid and reagent can then be refluxed at between 0 and 100° C., between 10 and 90° C., between 20 and 80° C., between 40 and 70° C. or between 60 and 70° C. The progress of the reaction can be monitored by thin-layer chromatography. After completion of the reaction the solvent can be removed by distillation under vacuum. The remaining solid can then be washed with water and dried to obtain the polymer.

In various embodiments, the polymers of the present invention can be prepared as shown in the following Scheme:

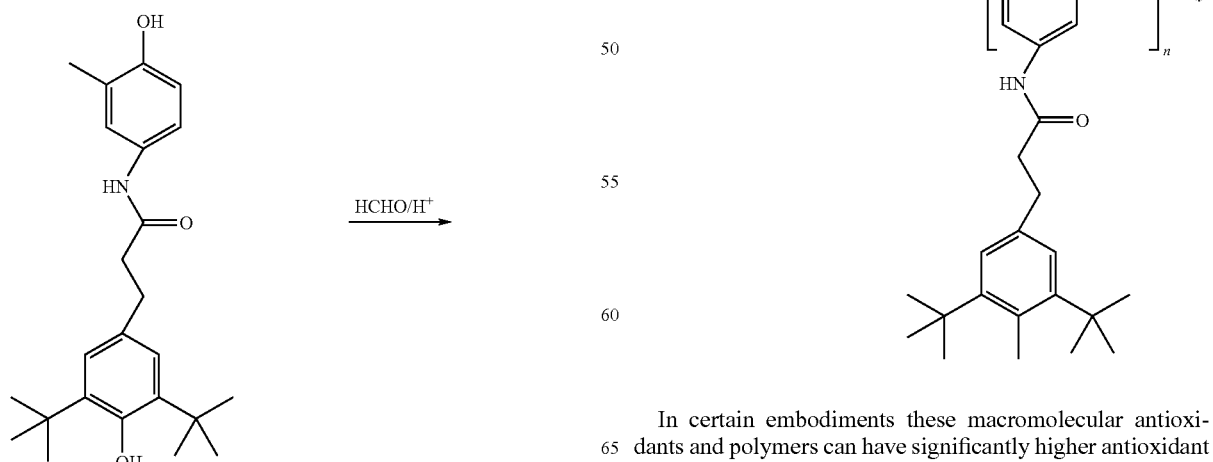

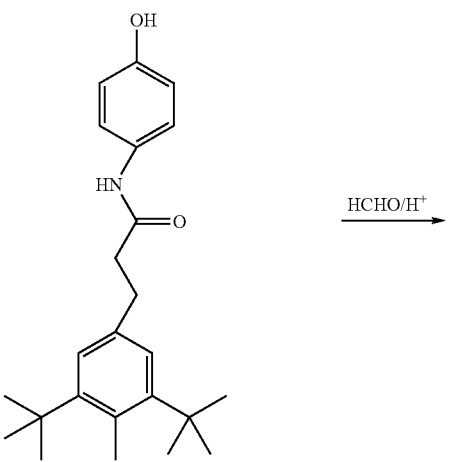

In certain embodiments these macromolecular antioxidants and polymers can have significantly higher antioxidant activities along with improved thermal stability and performance in a wide range of materials including but not limited to plastics, elastomers, lubricants, petroleum based products (lubricants, gasoline, aviation fuels, and engine oils), cooking oil, cosmetics, processed food products, compared to commercially available antioxidants. In certain embodiments the present invention also discloses the superior performance of macromolecules of the formula I in materials including but not limited to polyolefins.

The compounds and polymers of the present invention can be used as antioxidants to inhibit oxidation of an oxidizable material. Such as, for example to increase the shelf life of an oxidizable material.

The antioxidant compounds and polymers of the present invention can be employed to inhibit the oxidation of an oxidizable material, for example by contacting the material with an antioxidant compound or polymer of the present invention.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof.

In certain embodiments, the oxidizable material is an organic polymer or plastic. In certain embodiments, the oxidizable material is an elastomer. In certain embodiments, the oxidizable material is a lubricant. In certain embodiments, the oxidizable material is a petroleum based product. In certain embodiments, the oxidizable material is an edible oil or cooking oil. In certain embodiments, the oxidizable material is a cosmetic. In certain embodiments, the oxidizable material is a processed food product.

In particular the oxidizable material is a lubricant or a mixture of lubricants.

The shelf life of many materials and substances contained within the materials, such as packaging materials, are enhanced by the presence of the antioxidants of the present invention. The addition of an antioxidant of the present invention to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant (e.g., by spraying the antioxidant or by applying as a thin film coating), blended with or mixed with an antioxidant, or otherwise have an antioxidant present within it. In one example, a thermoplastic such as polyethylene, polypropylene or polystyrene can be melted in the presence of an antioxidant in order to minimize its degradation during the polymer processing.

The lifetime of lubricants, lubricant oils, mixtures thereof and compositions comprising lubricants and lubricant oils in general can be improved by contacting the lubricant, lubricant oil, mixtures thereof or composition comprising the lubricant or lubricant oil or mixtures thereof with compounds of the present invention, as described herein.

In certain embodiments of the present invention, polyolefins and mixtures of polyolefins can be stabilized by contacting the polyolefin or mixture of polyolefins with a compound or polymer of the present invention. These polyolefins and mixtures of polyolefins, include, but are not limited to substituted polyolefins, polyacrylates, polymethacrylates and copolymers of polyolefins. The following are examples of some types of polyolefins which can be stabilized by the methods of the present invention:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE) and ultra low density polyethylene (ULDPE).

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1., for example, mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Blends of polymers mentioned under 1. with impact modifiers such as ethylene-propylene-diene monomer copolymers (EPDM), copolymers of ethylene with higher alpha-olefins (such as ethylene-octene copolymers), polybutadiene, polyisoprene, styrene-butadiene copolymers, hydrogenated styrene-butadiene copolymers, styrene-isoprene copolymers, hydrogenated styrene-isoprene copolymers. These blends are commonly referred to in the industry as TPO's (thermoplastic polyolefins).

In certain particular embodiments polyolefins of the present invention are for example polypropylene homo- and copolymers and polyethylene homo- and copolymers. For instance, polypropylene, high density polyethylene (HDPE), linear low density polyethylene (LLDPE) and polypropylene random and impact (heterophasic) copolymers.

In certain embodiments of the present invention, 50% to 20% by weight of the antioxidants of the present invention are added to the polyolefin. In certain other embodiments of the present invention, 10% to 5% by weight of the antioxidants of the present invention are added to the polyolefin. In certain other embodiments of the present invention, 0.1% to 2% by weight of the antioxidants of the present invention are added to the polyolefin. In certain other embodiments of the present invention, 0.001% to 0.5% by weight of the antioxidants of the present invention are added to the polyolefin. This percentage varies depending upon their end application and type of the polyolefin.

In certain embodiments of the present invention the antioxidants of the present invention are usually added to the polyolefin with stirring at between 0 and 100° C., between 10 and 80° C., between 20-30° C. or at room temperature.

In certain embodiments the antioxidants of the present invention can be mixed with other antioxidants or additives to produce formulations, such as those described in Provisional Patent Application No. 60/742,150, filed Dec. 2, 2005, Title: Lubricant Composition, by Kumar, Rajesh, et al., and Provisional Patent Application No. 60/731,325, filed Oct. 27, 2005, Title: Stabilized Polyolefin Composition, by Kumar, Rajesh, et al., the entire contents of each of which are incorporated herein by reference.

Without wishing to be bound be theory it is believed that alkylation at the phenolic oxygen or ortho to the phenolic hydroxy (or alkoxy) group increases secondary properties of the antioxidants such as maintaining the melt flow index (MFI), decreasing the yellowing index (YI).

In certain embodiments the present invention relates to a method of preventing oxidation comprising combining an oxidizable material with a compound represented by Structural Formula I:

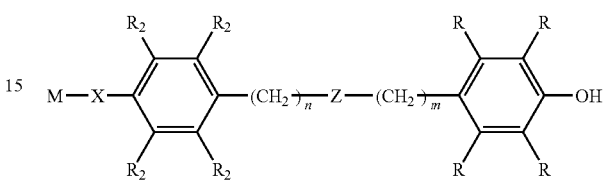

wherein, independently for each occurrence, n and m are integers from 0 to 6, inclusive;

Z is —C(O)O—, —OC(O)—, —C(O)NH—, —NHC(O)—, —NH—, —CH=N—, —C(O)—, —O—, —S—, —C(O)OC(O)—, or a bond;

R is H, $C_{1-6}$ alkyl, —OH, —NH$_2$, —SH, aryl, ester, or

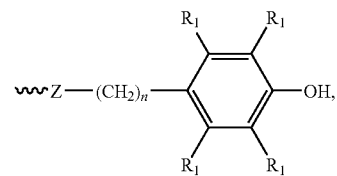

wherein at least one R adjacent to the —OH group is a bulky alkyl group (e.g., butyl, sec-butyl, tert-butyl, 2-propyl, 1,1-dimethylhexyl, and the like);

$R_1$ is H, $C_{1-6}$ alkyl, aryl, aralkyl, —OH, —NH$_2$, —SH, or C1-C6 alkyl ester wherein at least one $R_1$ adjacent to the —OH group is a bulky alkyl group (e.g., butyl, sec-butyl, tert-butyl, 2-propyl, 1,1-dimethylhexyl, and the like); and —$R_2$ is H, $C_{1-6}$ alkyl, aryl, aralkyl, —OH, —NH$_2$, —SH, or ester, wherein at least one $R_1$ adjacent to the —OH group is a bulky alkyl group (e.g., butyl, sec-butyl, tert-butyl, 2-propyl, 1,1-dimethylhexyl, and the like);

X is —C(O)O—, —OC(O)—, —C(O)NH—, —NHC(O)—, —NH—, —CH=N—, —C(O)—, —O—, —S—, —C(O)OC(O)—, or a bond;

M is H, aryl, C-1 to C-20 linear or branched alkyl chain with or without any functional group anywhere in the chain, or

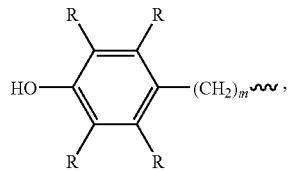

wherein m and each R is independently as described above; wherein $R_2$ is H, $C_{1-6}$ alkyl, —OH, —NH$_2$, —SH, aryl, ester, or

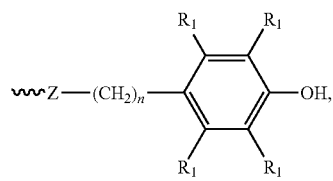

wherein at least one $R_2$ is —OH and n, Z, and each R1 are independently as described above.

In certain embodiments, the oxidizable material is an organic polymer or plastic. In certain embodiments, the oxidizable material is an elastomer. In certain embodiments, the oxidizable material is a lubricant. In certain embodiments, the oxidizable material is a petroleum based product. In certain embodiments, the oxidizable material is an edible oil or cooking oil. In certain embodiments, the oxidizable material is a cosmetic. In certain embodiments, the oxidizable material is a processed food product.

EXEMPLIFICATION

Example 1

Improved Oxidation Induction Times of the Antioxidants of the Present Invention in Plastics The synthesized alkylated macromolecular antioxidants of formula I and in particular of formula III were evaluated and found to have desirable antioxidant properties in plastics. The antioxidant properties of these novel compounds were studied by mixing 5000 ppm of these novel antioxidants in polypropylene and extruding the mixture with a single screw extruder. The oxidative induction time (OIT) values were determined using ASTM D3895 method by differential scanning calorimetry (DSC). The value of OITs in minutes obtained is listed in Table 1.

TABLE 1

Comparison of performance and properties of various cantioxidants of the present invention (AO's)

| Compound III M | M.P (° C.) | Hexane solubility | OIT @ 5000 ppm in PP (mins) |
|---|---|---|---|
| M = $C_{10}H_{21}$ | 100-105 | 5.7 mg/ml | 63-75 |
| M = $CH_3$ | 170-175 | 1.2 mg/ml | 52 |
| M = $C_4H_9$ | 135-140 | 2 mg/ml | 30 |

FIG. 1 is a graph showing superior performance of alkylated macromolecules of Formula III with M=$C_{10}H_{21}$, compared with commercially available antioxidants.

Figure 2:
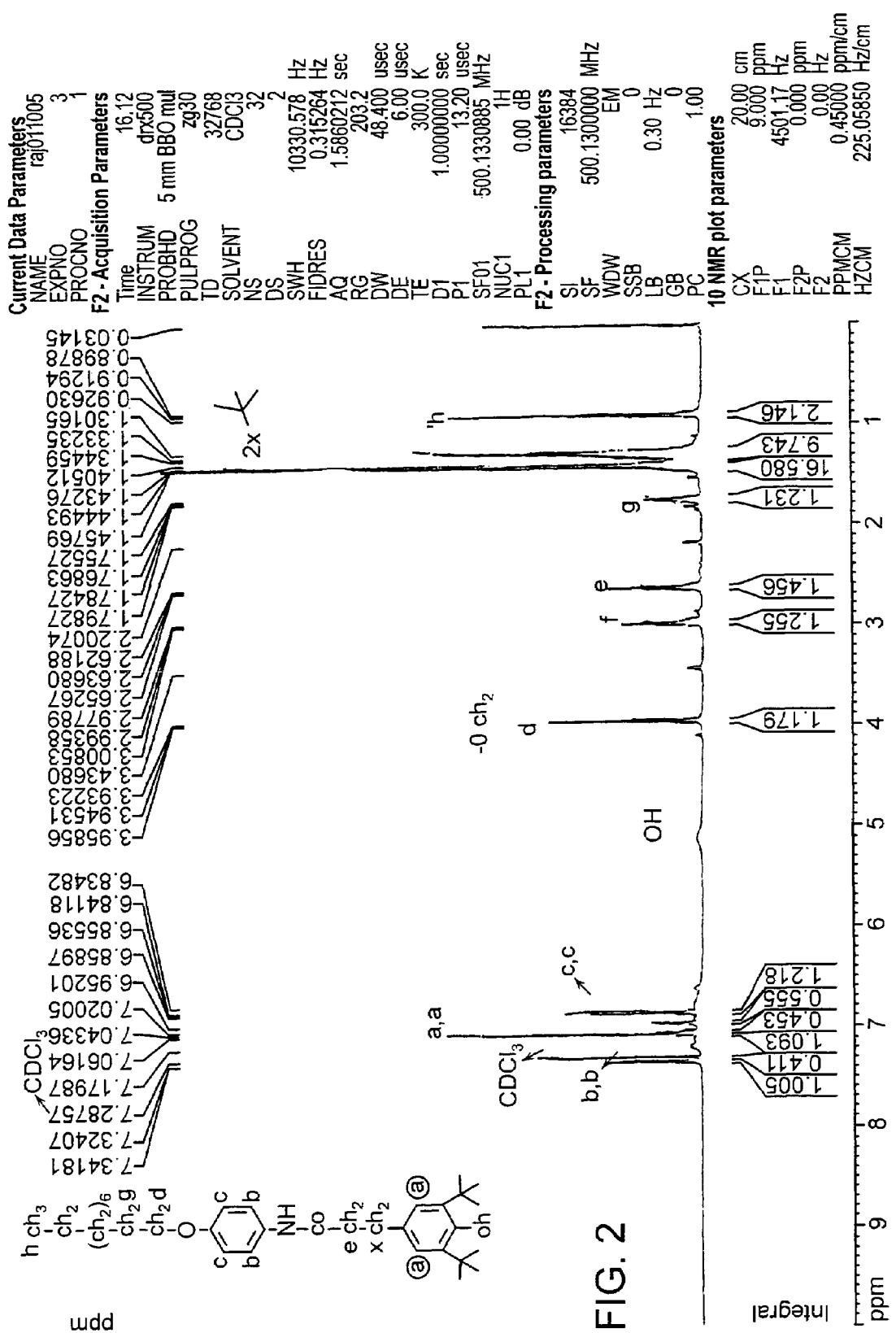
FIG. 2 is a high resolution nuclear magnetic resonance (NMR) spectrum of a compound of Formula III of the present invention having M=$C_{10}H_{21}$.

FIG. 2 is a high resolution nuclear magnetic resonance (NMR) spectrum of the compound of Formula III having M=$C_{10}H_{21}$.

Figure 3:
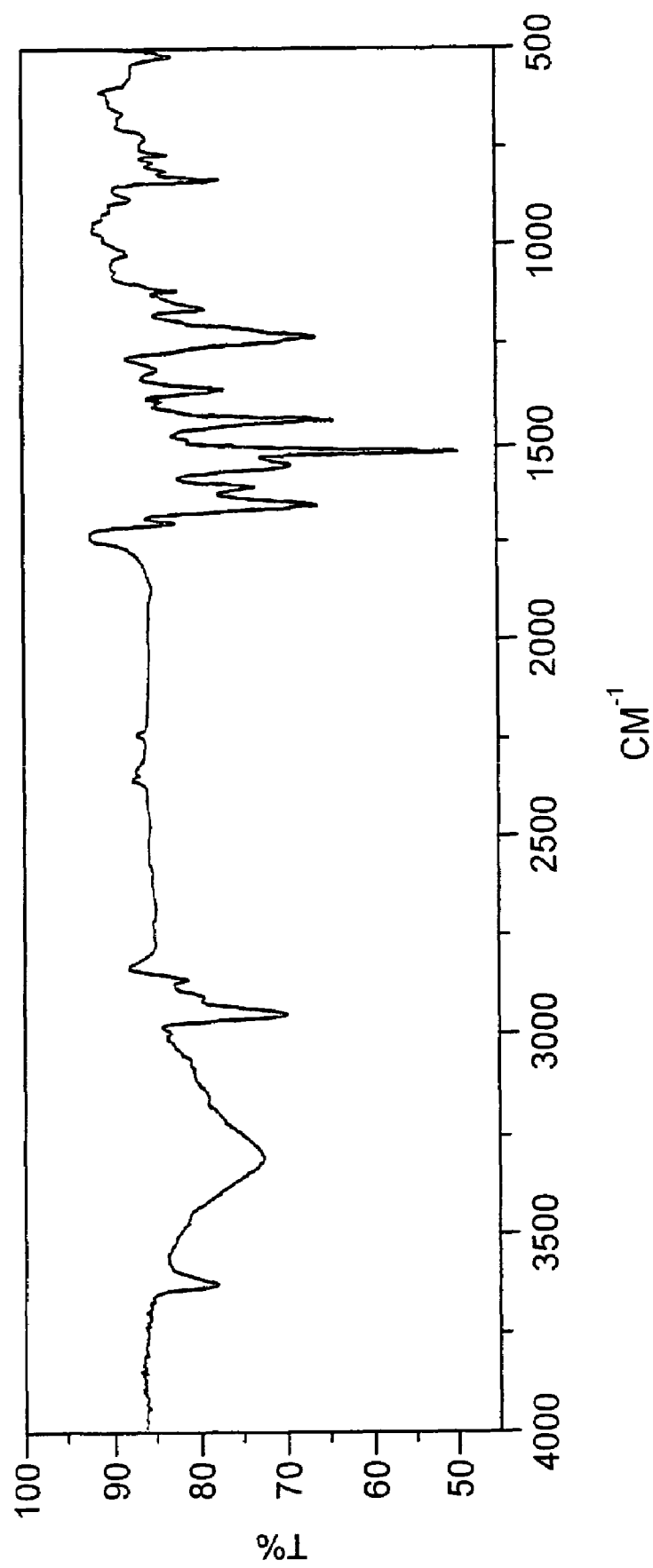
FIG. 3 is a Fourier Transform Infrared (FT-IR) spectrum of a compound of Formula III of the invention having M=$C_{10}H_{21}$. The assignments of the peaks in FIG. 3 are consistent with the structure of the compound.

FIG. 3 is a Fourier Transform Infrared (FT-IR) spectrum of the compound of Formula III having M=$C_{10}H_{21}$. The assignments of the peaks in FIG. 3 are consistent with the structure of the compound.

This data suggests that proposed antioxidants in this disclosure have nearly 2.8 times better when compared with commercially available antioxidant Irganox 1010, and 1.8 times better when compared with commercially available antioxidant Irganox 1330. In this comparison test, each sample was prepared by combining 5000 ppm of antioxidant in polypropylene and extruding using a single screw extruder.

Example 2

Improved Secondary Properties of the Polymeric Antioxidants of the Present Invention in Plastics The macromolecular antioxidants i and ii:

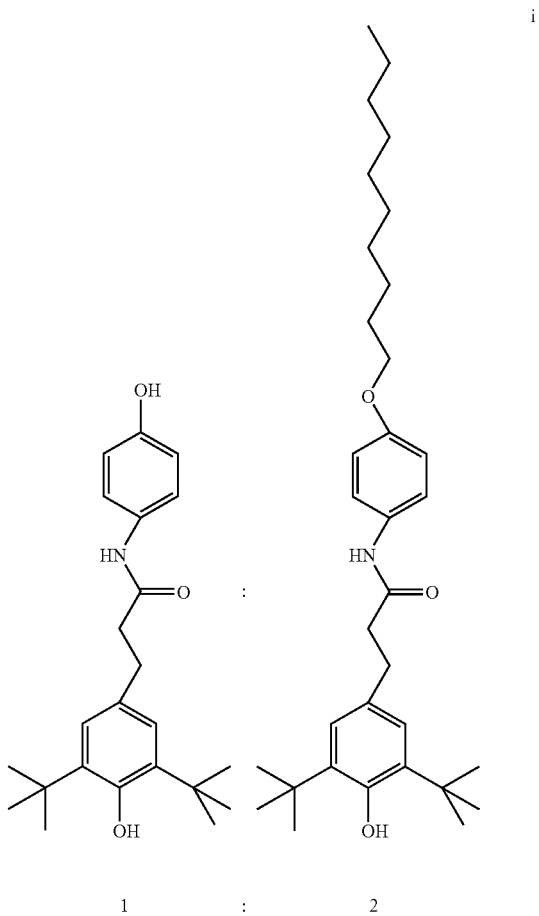

-continued

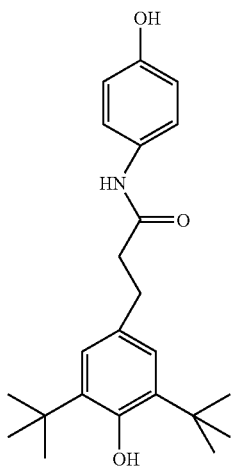

ii were evaluated for the antioxidant activity in polypropylene homopolymer (PP) (nominal MFI 4 dg/min) and found to have desirable secondary antioxidant properties. The macromolecular antioxidant i is a composition comprising a 1:2 mixture of the two compounds depicted above. The macromolecular antioxidants i (1000 ppm), ii (1000 ppm) and commercially available Irganox® 1010 (1000 ppm) were formulated with secondary antioxidants (selected from Irgafos® 168 and Irgafos® 126 (1000 ppm)) and acid neutralizer calcium sterate (1000 ppm). The formulations were dry blended in the PP and extruded with a single screw extruder at zone temperatures of 200, 230, 250, 250° C. The melt flow index (MFI) was measured using ASTM D 1238, the yellowing index (YI) was measured on extruded granules packed in a quartz cuvette.

Figure 4:
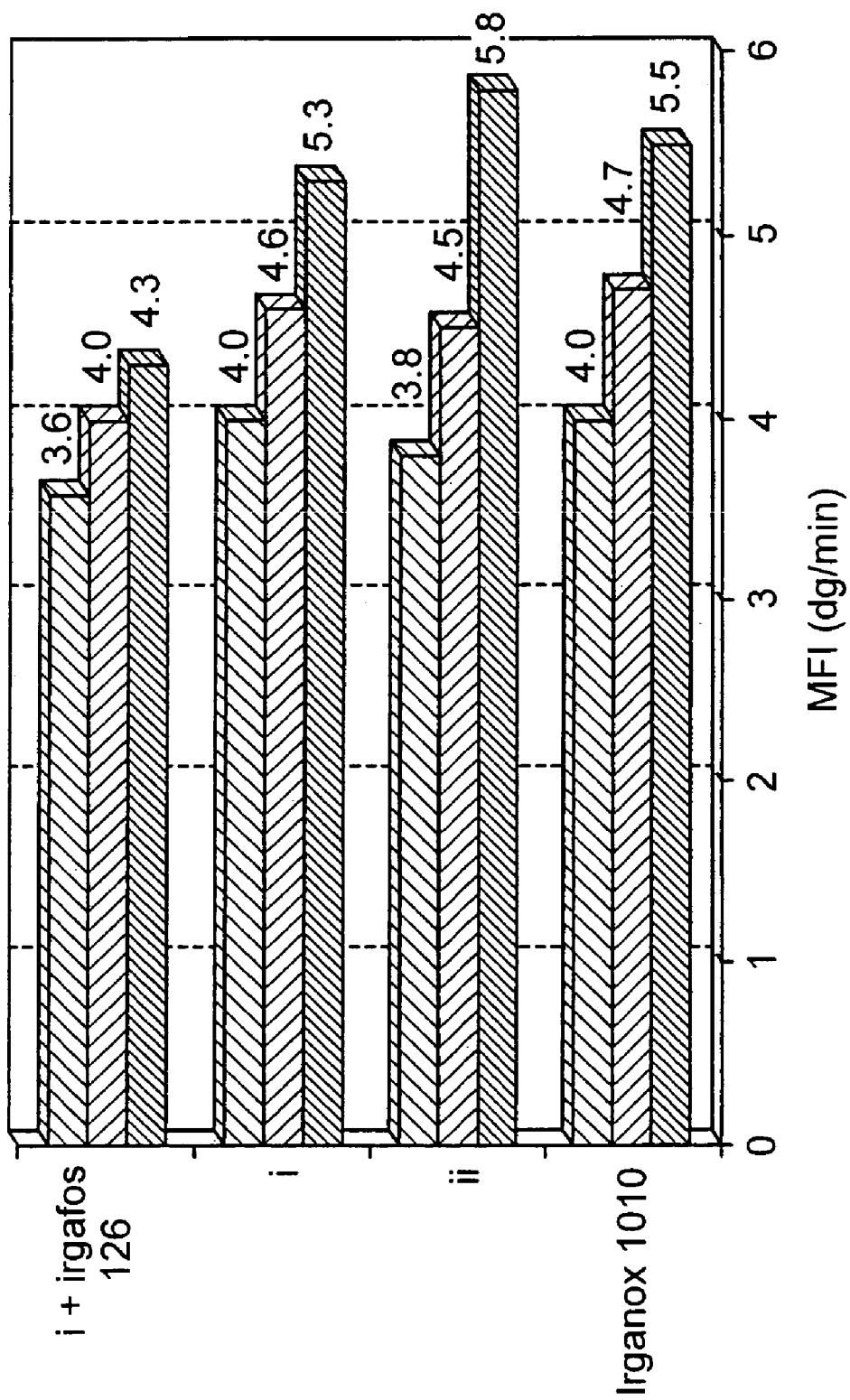
FIG. 4 and FIG. 5 are graphs showing the melt flow index (MFI) results for antioxidants of the present invention versus Irganox® 1010.
Figure 5:
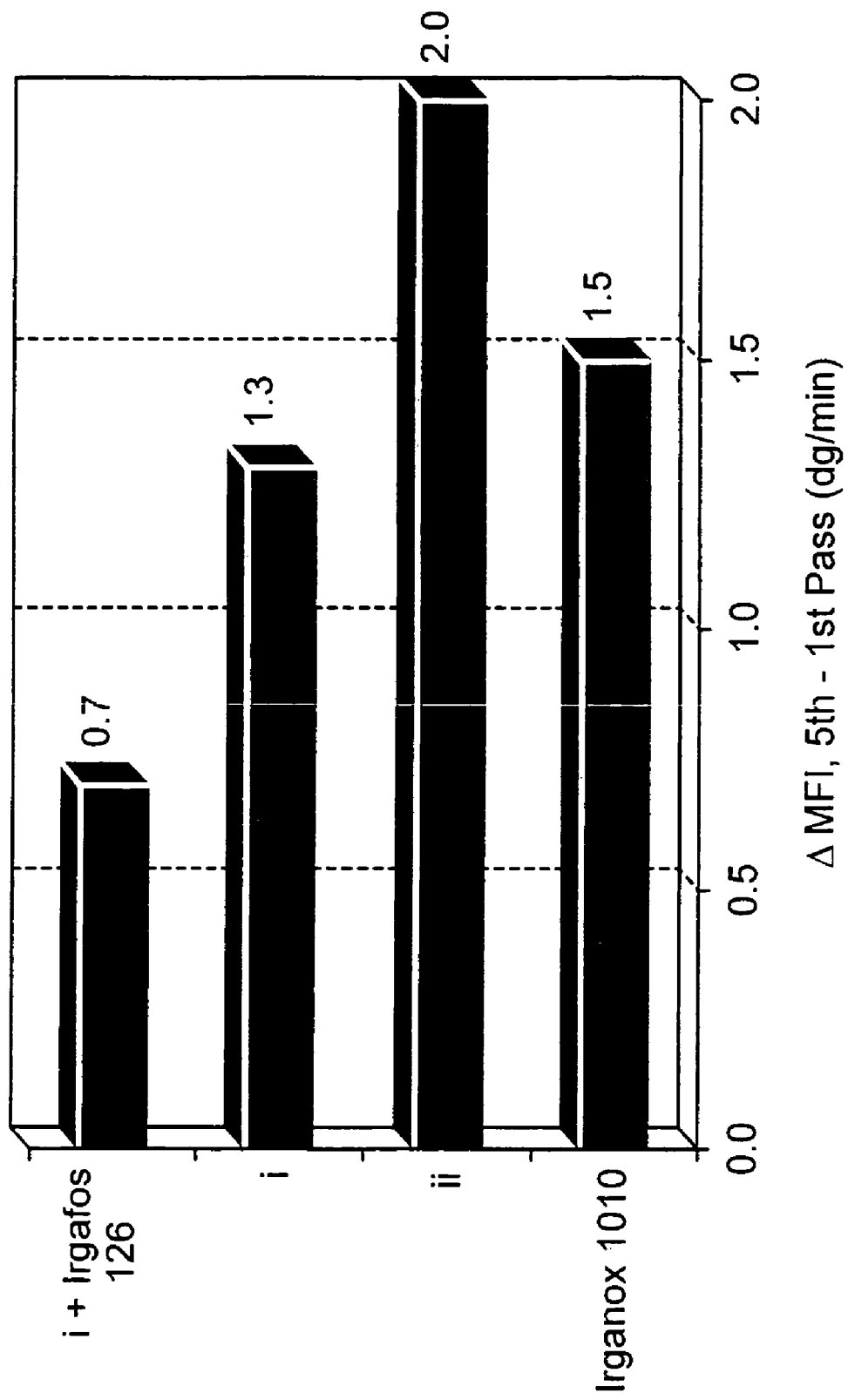

The MFI results are shown in FIG. 4 and FIG. 5, which demonstrate that the maintenance of melt flow index over five extruder passes for the antioxidant i matches and is slightly superior to commercially available Irganox® 1010 and to the antioxidant ii. These figures also show that substituting Irgafos® 126 for Irgafos® 168 improves the ability of the antioxidant i to maintain the MFI. In FIGS. 4 and 5 all formulations contain 1000 ppm AO (antioxidant), 1000 ppm Irgafos® 168 (except where noted) and 1000 ppm calcium sterate.

Figure 6:
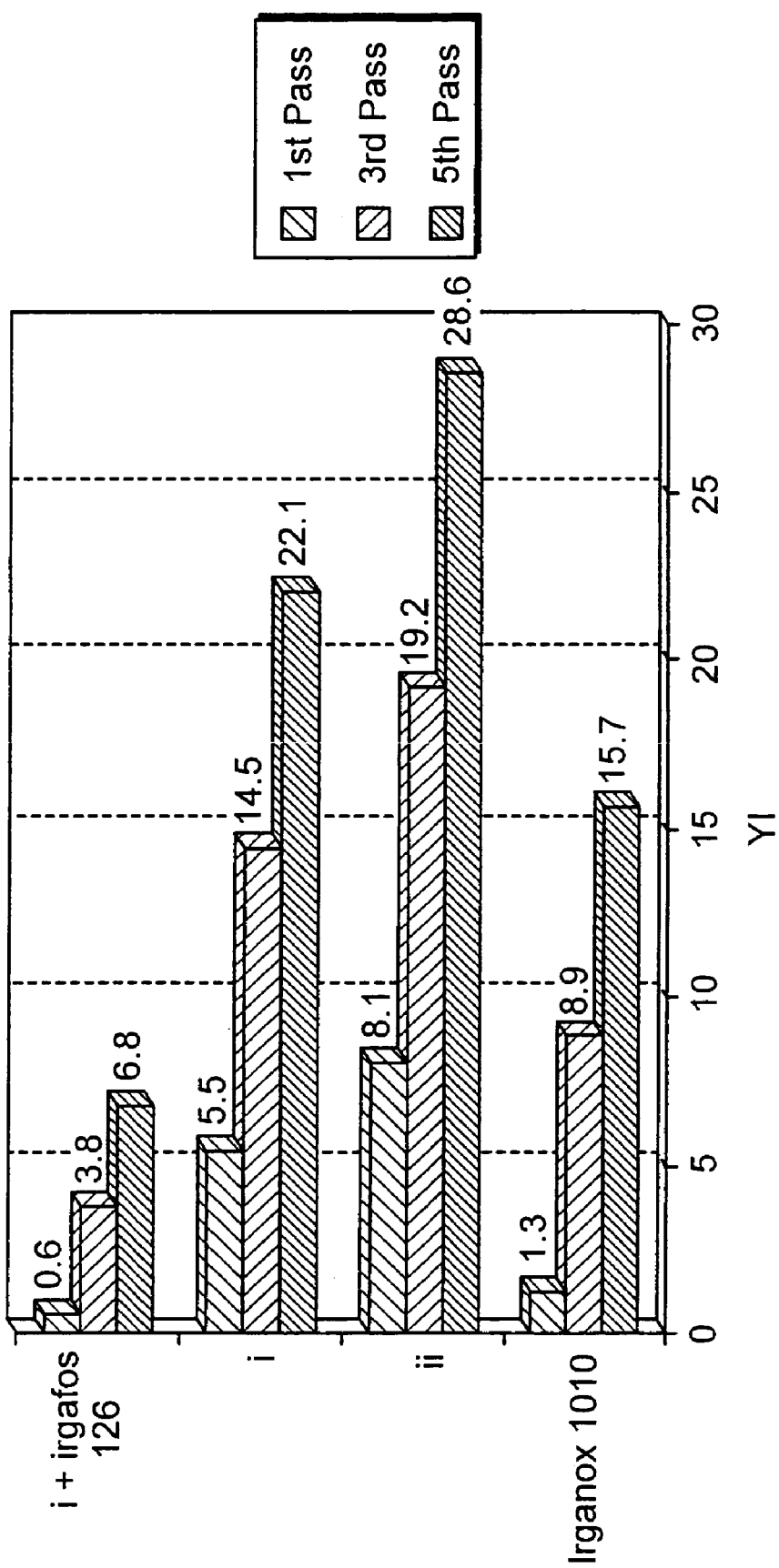
FIG. 6 and FIG. 7 are graphs showing the color development results for antioxidants of the present invention versus Irganox® 11010.
Figure 7:
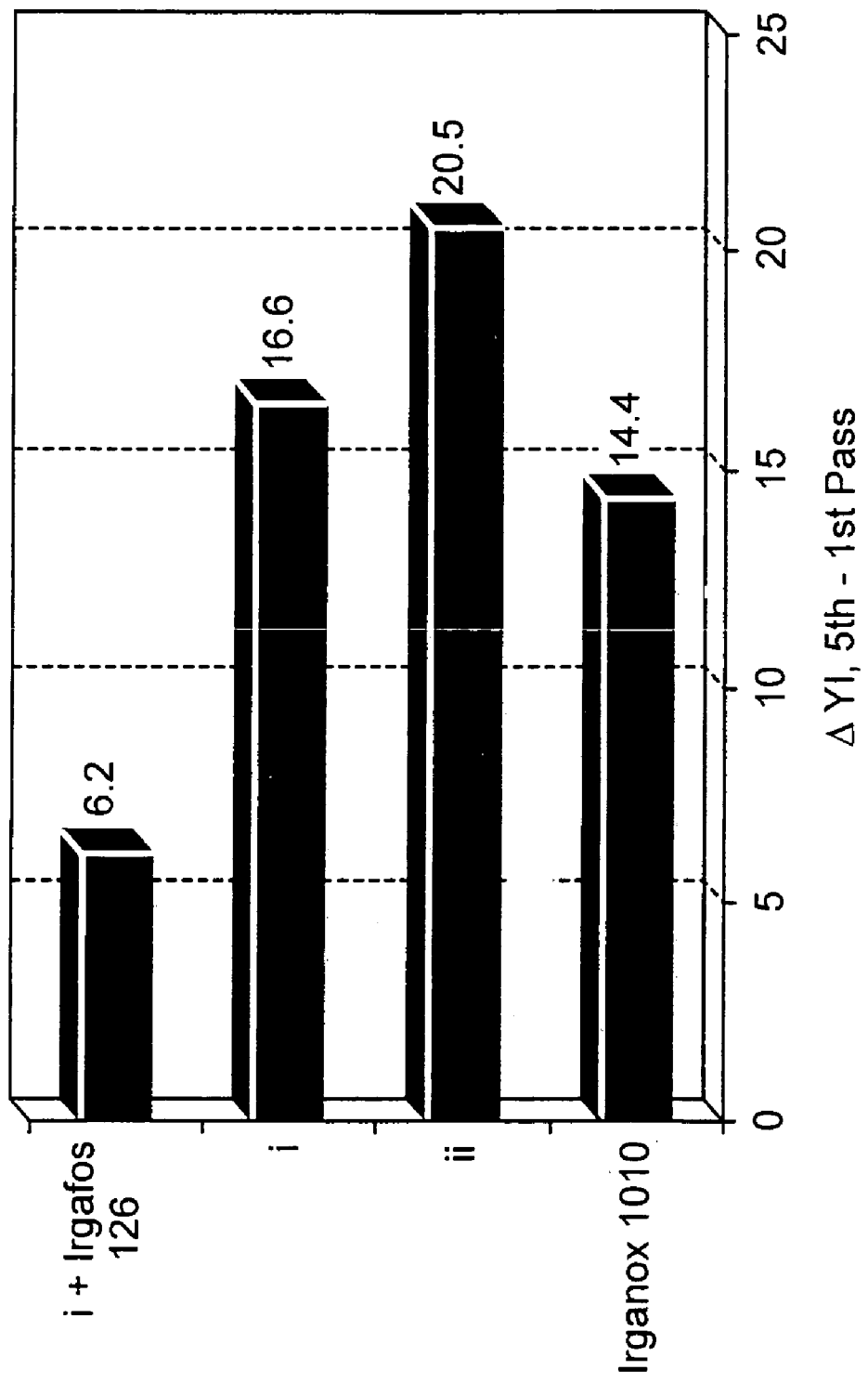

The YI results are shown in FIG. 6 and FIG. 7, which demonstrate that the YI is much improved for antioxidant i over antioxidant ii and also substituting Irgafos® 126 for Irgafos® 168 improves the secondary antioxidant properties of antioxidant i. In FIGS. 6 and 7 all formulations contain 1000 ppm AO, 1000 ppm Irgafos 168 (except where noted) and 1000 ppm calcium sterate.

Example 3

Improved Oxidation Induction Times of the Polymeric Antioxidants of the Present Invention in Plastics The macromolecular antioxidants i and ii:

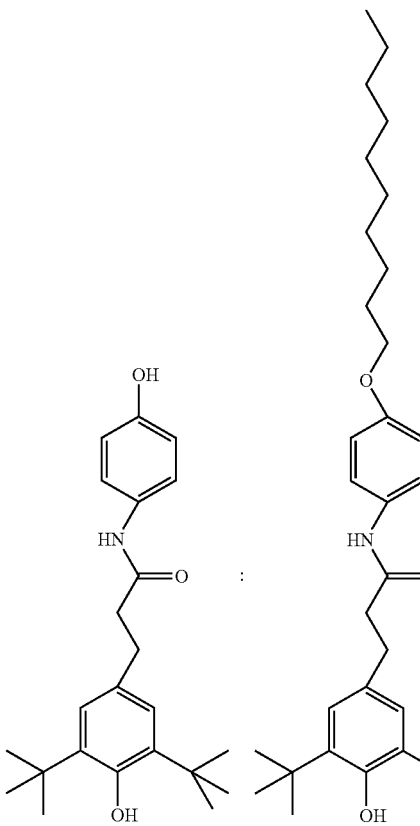

1 : 2

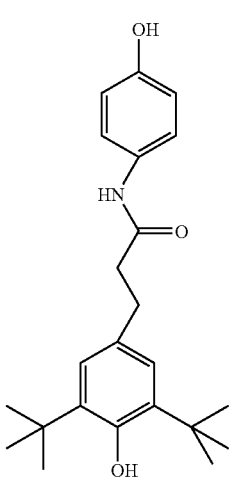

ii were evaluated for the antioxidant activity in polypropylene homopolymer (PP) (nominal MFI 4 dg/min) and found to have desirable secondary antioxidant properties. The antioxidants macromolecular antioxidants i (1000 ppm), ii (1000 ppm) and commercially available Irganox® 11010 (1000 ppm) were formulated with secondary antioxidants (selected from Irgafos® 168 and Irgafos® 126 (1000 ppm)) and acid neutralizer calcium sterate (1000 ppm). The formulations were dry blended in the PP and extruded with a single screw extruder at zone temperatures of 200, 230, 250, 250° C. The oxidative induction time (OIT) values were determined using ASTM D3895 method by differential scanning calorimetry (DSC).

Figure 8:
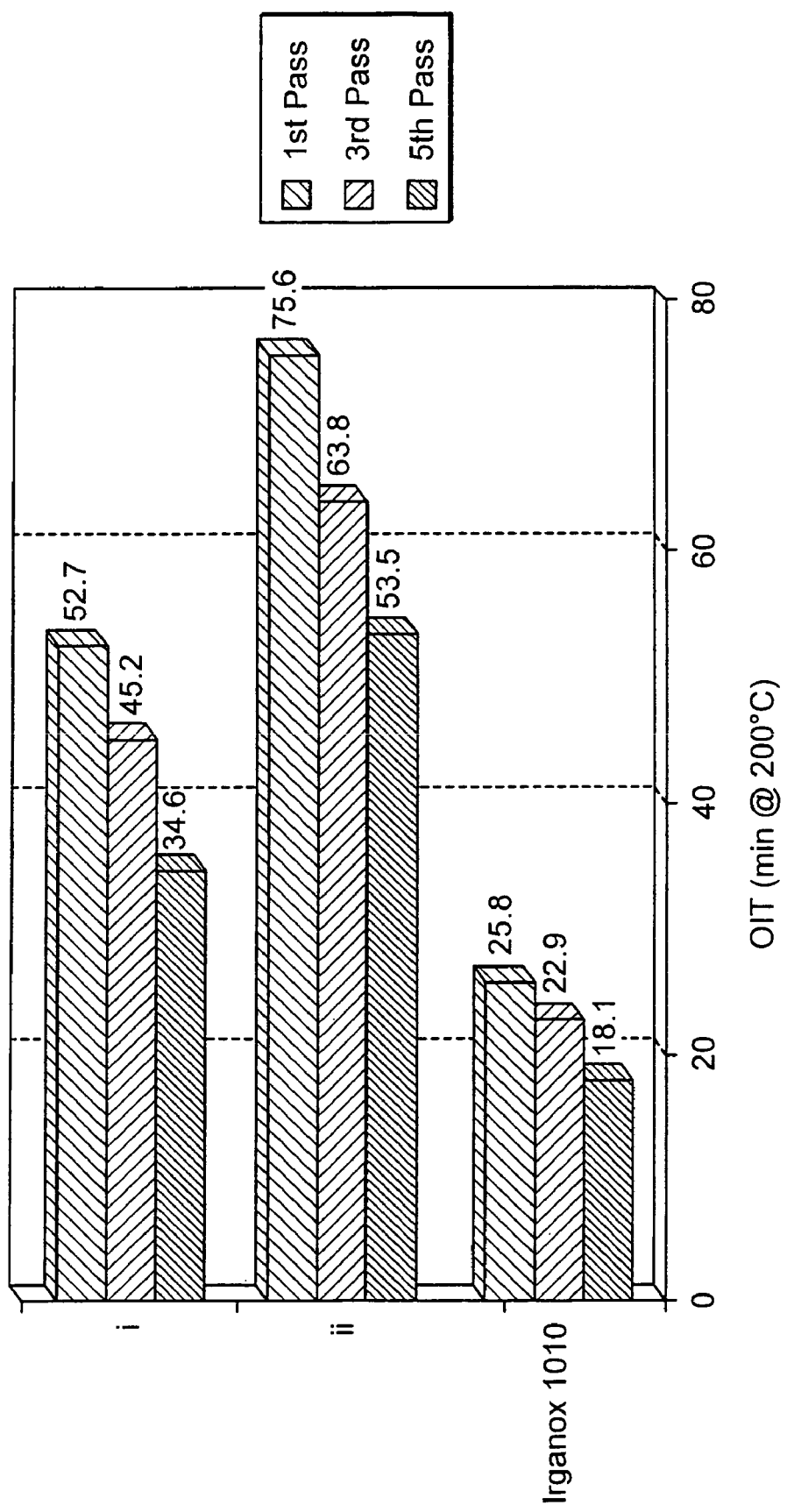
FIG. 8 is a graph showing the oxidative induction time (OIT) results for antioxidants of the present invention versus Irganox® 1010.

The OIT results are shown in FIG. 8, which demonstrates that the oxidative induction times for antioxidant i is far superior to commercially available Irganox® 1010. Even after five extruder passes PP samples mixed with antioxidant i show higher OIT values that PP samples mixed with Irganox® 1010 after one extruder pass. All formulations in FIG. 8 contain 1000 ppm AO, 1000 ppm Irgafos® 168 and 1000 ppm calcium stearate.

Example 4

Heat Aging of the Polymeric Antioxidants of the Present Invention in Plastics The macromolecular antioxidants i and ii:

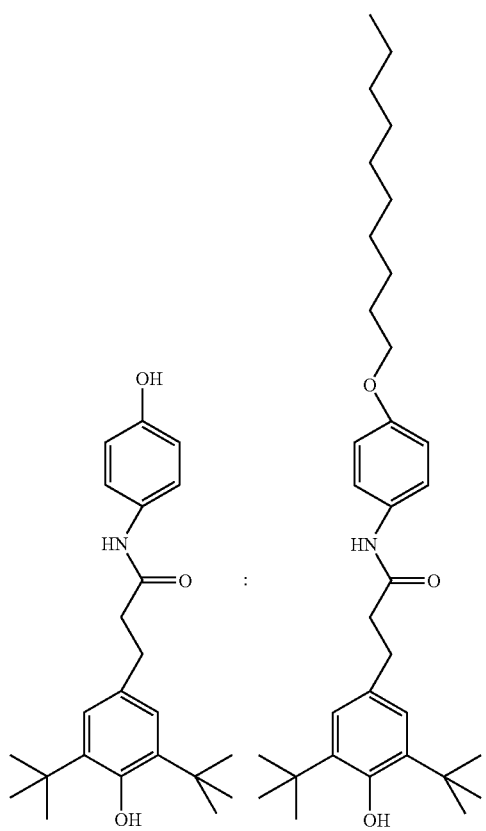

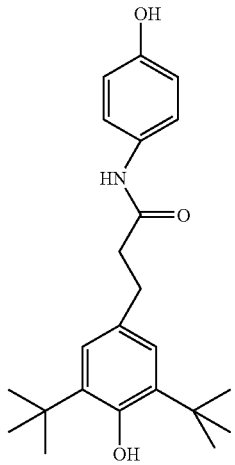

were evaluated for the antioxidant activity in polypropylene homopolymer (PP) (nominal MFI 4 dg/min) and found to have desirable secondary antioxidant properties. The antioxidants macromolecular antioxidants i (1000 ppm), ii (1000 ppm), commercially available Irganox® 1010 (1000 ppm), Irganox® 1330 (1000 ppm) and Irganox® 1076 (1000 ppm) were formulated with secondary antioxidants (Irgafos® 168 (1000 ppm)) and acid neutralizer (calcium sterate (1000 ppm)). The formulations were dry blended in the PP and extruded with a single screw extruder at zone temperatures of 200, 230, 250, 250° C. The heat aging was measured by placing a 1.6 mm film of the PP formulations in an oven at 150° C. and checking the films daily. The films were considered to have failed when cracks appeared on the films when they were subjected to a force, such as, bending.

Figure 9:
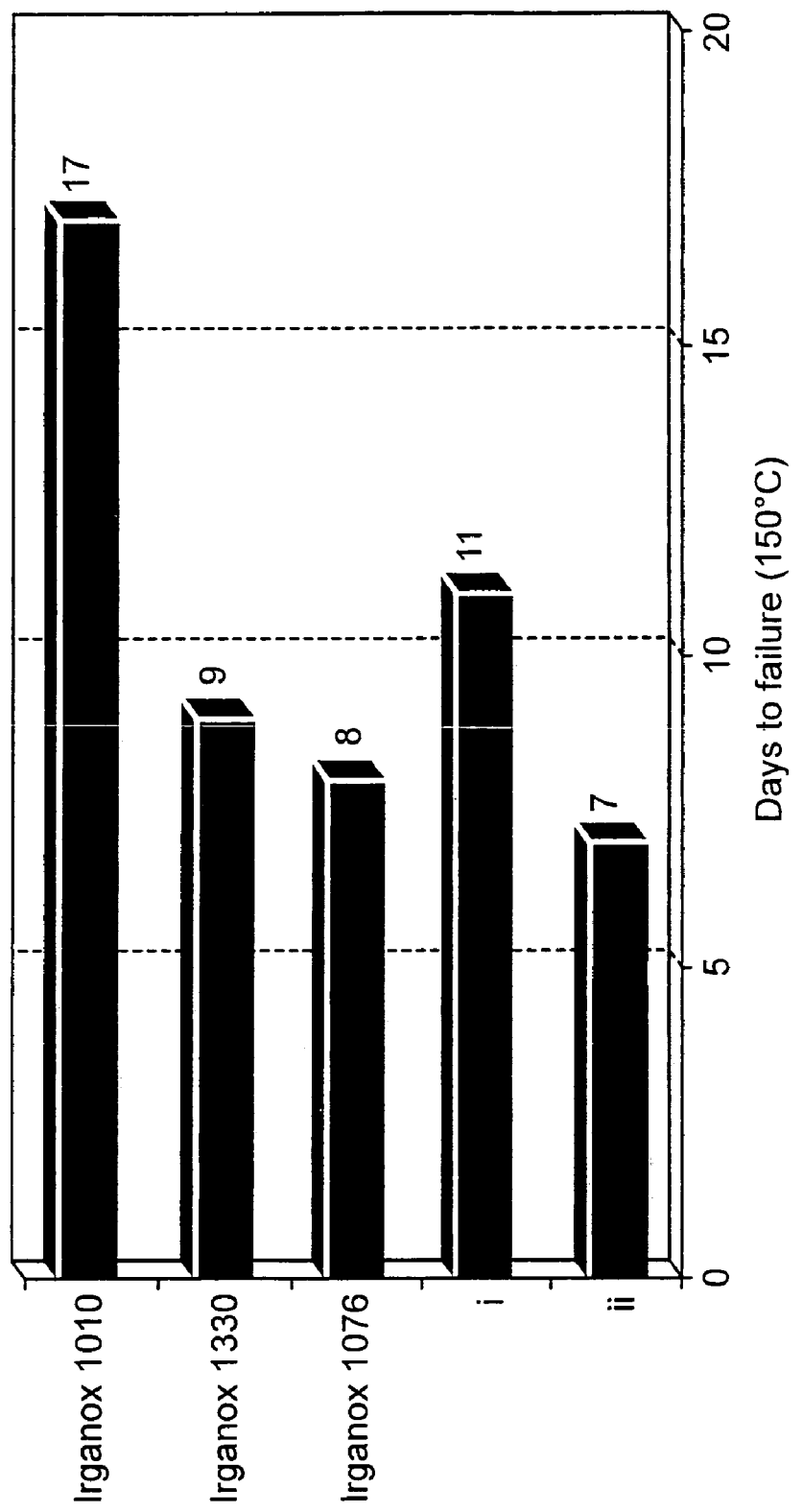
FIG. 9 is a graph showing the heat aging results for antioxidants of the present invention versus Irganox® 1010, Irganox® 1330 and Irganox® 1076.

The heat aging results are shown in FIG. 9, which demonstrate that the antioxidant i is superior to antioxidant ii and to commercially available Irganox® 1330 and Irganox® 1076 and is above the typical industry standard of 8-9 days. All formulations in FIG. 9 are in the form of a substrate extruded film of 1.6 mm thick. All formulations contain 1000 ppm AO, 1000 ppm calcium stearate and 1000 ppm Irgafos 168.

Example 5

Synthesis of Compounds of the Present Invention Represented by Formula III where M is $C_{10}H_{21}$

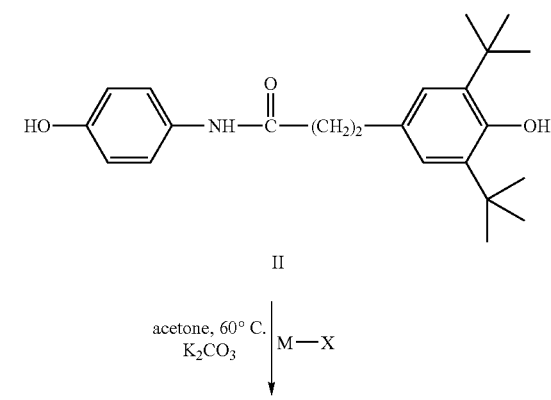

-continued

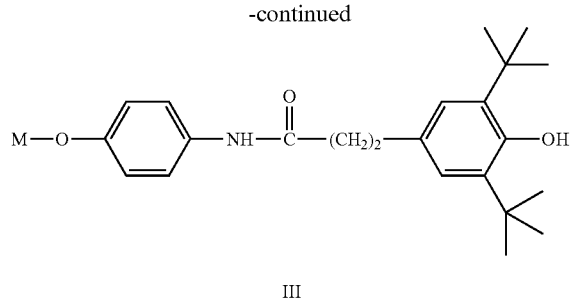

III 369 g of phenolic starting material above was dissolved in 1.5 L of anhydrous acetone and to that added 136 g of fused potassium carbonate. The reaction mixture was stirred for some time and to that added 220 g of bromodecane over a period of 60 minutes. The reaction mixture was refluxed and progress of the reaction was monitored by thin layer chromatography. After completion of the reaction, potassium carbonate was filtered and the solvent was removed under vacuum to get the crude solid. The solid was obtained was re-dissolved in hexane and filtered to obtain the pure solid.

Example 6

Synthesis of Compounds of the Present Invention Represented by Formula III where M is $C_1H_3$

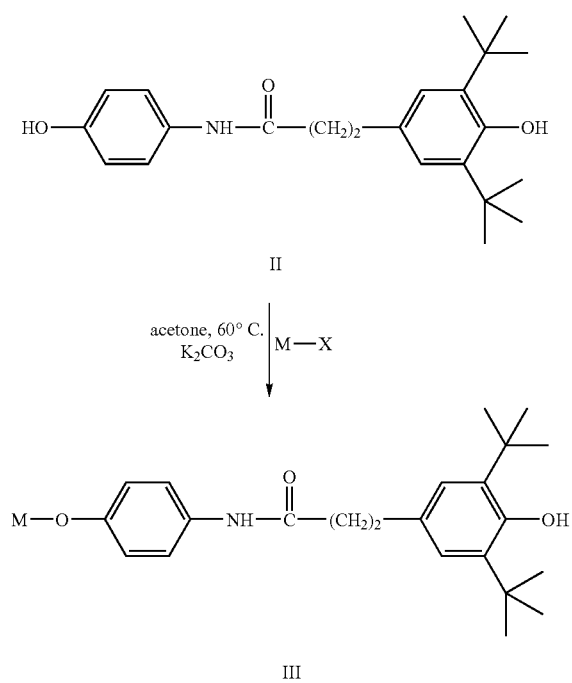

75 g of phenolic compound represented II was dissolved in 200 ml of anhydrous acetone and to that added 25 g of fused potassium carbonate. The resultant reaction mixture was stirred for 10 minutes followed by the addition of 30 g of methyl iodide and refluxed for a predetermined time period. The product methylated II was isolated by filtration of potassium carbonate and drying the filtrate by removing the solvent under vacuum.

Example 7

Synthesis of Polymers of the Present Invention

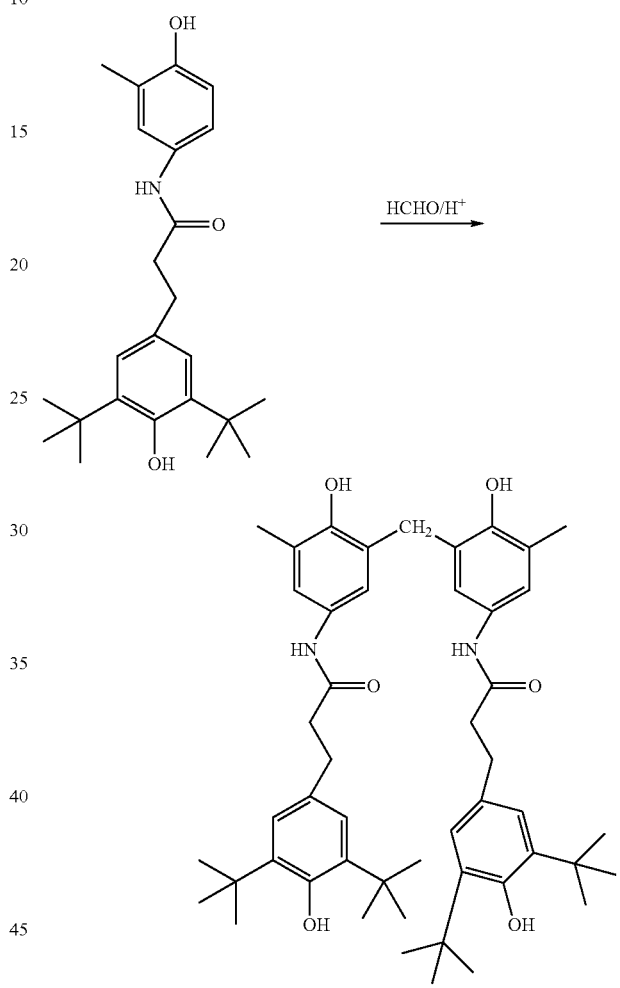

1.5 g of 3,5-bis(1,1-dimethylethyl)-4-hydroxy-N-(4-hydroxy-3-Methyl phenyl)-benzenepropanamide, and paraformaldehyde were dissolved in 20 ml of methanol. To that added 0.1 ml of hydrochloric acid and the reaction mixture was refluxed at 65° C. The progress of the reaction was monitored by thin layer chromatography. After completion of the reaction, the solvent was removed by distillation under vacuum. The solid obtained after distillation of the solvent was washed with water and dried to obtain the resultant product.

The entire contents of each of the following are incorporated herein by reference.

Provisional Patent Application No. 60/632,893, filed Dec. 3, 2004, Title: Process For The Synthesis Of Polyalkylphenol Antioxidants, by Suizhou Yang, et al;

patent application Ser. No. 11/292,813 filed Dec. 2, 2005, Title: Process For The Synthesis Of Polyalkylphenol Antioxidants, by Suizhou Yang, et al;

Provisional Patent Application No. 60/633,197, filed Dec. 3, 2004, Title: Synthesis Of Sterically Hindered Phenol Based Macromolecular Antioxidants, by Ashish Dhawan, et al.;

patent application Ser. No. 11/293,050; filed Dec. 2, 2005, Title: Synthesis Of Sterically Hindered Phenol Based Macromolecular Antioxidants, by Ashish Dhawan, et al.;

Provisional Patent Application No. 60/633,252, filed Dec. 3, 2004, Title: One Pot Process For Making Polymeric Antioxidants, by Vijayendra Kumar, et al.;

patent application Ser. No. 11/293,049; filed Dec. 2, 2005, Title: One Pot Process For Making Polymeric Antioxidants, by Vijayendra Kumar, et al.;

Provisional Patent Application No. 60/633,196, filed Dec. 3, 2004, Title: Synthesis Of Aniline And Phenol-Based Macromonomers And Corresponding Polymers, by Rajesh Kumar, et al.;

patent application Ser. No. 11/293,844; filed Dec. 2, 2005, Title: Synthesis Of Aniline And Phenol-Based Macromonomers And Corresponding Polymers, by Rajesh Kumar, et al.;

patent application Ser. No. 11/184,724, filed Jul. 19, 2005, Title: Anti-Oxidant Macromonomers And Polymers And Methods Of Making And Using The Same, by Ashok L. Cholli;

patent application Ser. No. 11/184,716, filed Jul. 19, 2005, Title: Anti-Oxidant Macromonomers And Polymers And Methods Of Making And Using The Same, by Ashok L. Cholli;

patent application Ser. No. 11/360,020, filed Feb. 22, 2006, Title: Nitrogen And Hindered Phenol Containing Dual Functional Macromolecules: Synthesis And Their Antioxidant Performances In Organic Materials, by Rajesh Kumar, et al.

Provisional Patent Application No. 60/655,638, filed Mar. 25, 2005, Title: Alkylated Macromolecular Antioxidants And Methods Of Making, And Using The Same, by Rajesh Kumar, et al.

Provisional Patent Application No. 60/731,125, filed Oct. 27, 2005, Title: Macromolecular Antioxidants And Polymeric Macromolecular Antioxidants, by Ashok L. Cholli, et al.

Provisional Patent Application No. 60/731,021, filed Oct. 27, 2005, Title: Macromolecular Antioxidants Based On Sterically Hindered Phenols And Phosphites, by Ashok L. Cholli, et al.

Provisional Patent Application No. 60/742,150, filed Dec. 2, 2005, Title: Lubricant Composition, by Kumar, Rajesh, et al.

Provisional Patent Application No. 60/731,325, filed Oct. 27, 2005, Title: Stabilized Polyolefin Composition, by Kumar, Rajesh, et al.

patent application Ser. No.: 11/040,193, filed Jan. 21, 2005, Title: Post-Coupling Synthetic Approach For Polymeric Antioxidants, by Ashok L. Cholli, et al.;

Patent Application No.: PCT/US2005/001948, filed Jan. 21, 2005, Title: Post-Coupling Synthetic Approach For Polymeric Antioxidants, by Ashok L. Cholli et al.;

Patent Application No.: PCT/US2005/001946, filed Jan. 21, 2005, Title: Polymeric Antioxidants, by Ashok L. Choll, et al.;

Patent Application No.: PCT/US03/10782, filed Apr. 4, 2003, Title: Polymeric Antioxidants, by Ashok L. Choll, et al.;

patent application Ser. No. 10/761,933, filed Jan. 21, 2004, Title: Polymeric Antioxidants, by Ashish Dhawan, et al.;

patent application Ser. No. 10/408,679, filed Apr. 4, 2003, Title: Polymeric Antioxidants, by Ashok L. Choll, et al.;

U.S. Pat. No. 6,770,785 B1

U.S. Pat. No. 5,834,544

Neftekhimiya (1981), 21(2): 287-298.

While this invention has been particularly shown and described with references to preferred embodiments thereof, it will be understood by those skilled in the art that various changes in form and details may be made therein without departing from the scope of the invention.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A compound represented by the following Structural Formula:

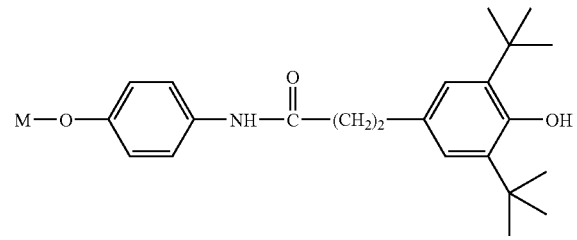

wherein M is a C1 to C20 linear or branched alkyl chain.

2. A compound represented by the following Structural Formula:

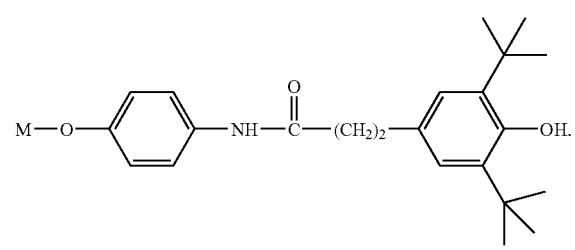

3. A method of making a compound represented by the following Structural Formula:

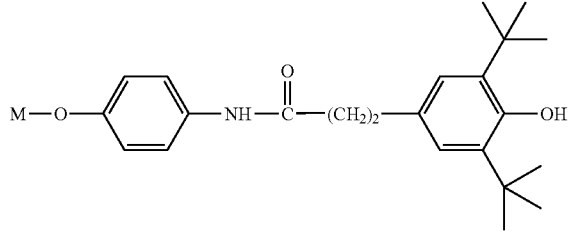

wherein M is a C1 to C20 linear or branched alkyl chain comprising the steps of:
 a) alkylating a compound represented by the following structural formula:

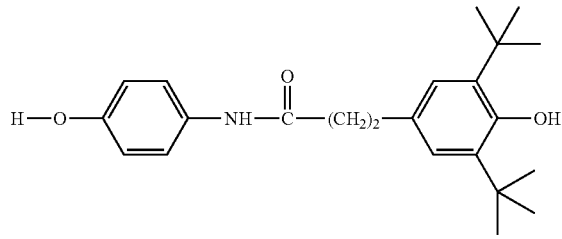

with a haloalkyl, wherein the alkyl component of the haloalkyl is a C1 to C20 linear or branched alkyl chain; and
 b) isolating the alkylated compound.

4. The method of claim 3, wherein the compound is represented by the following Structural Formula:

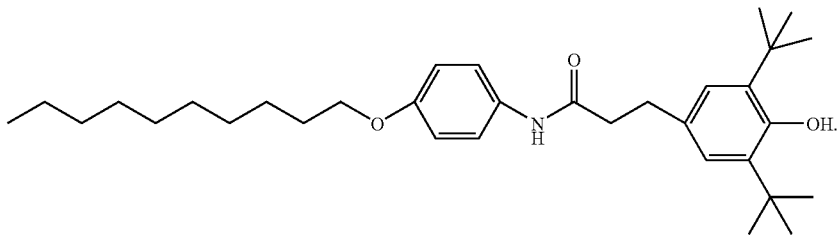

\* \* \* \* \*

UNITED STATES PATENT AND TRADEMARK OFFICE
CERTIFICATE OF CORRECTION

PATENT NO. : 7,705,185 B2  
APPLICATION NO. : 11/389564  
DATED : April 27, 2010  
INVENTOR(S) : Rajesh Kumar and Ashok L. Cholli Page 1 of 1

It is certified that error appears in the above-identified patent and that said Letters Patent is hereby corrected as shown below:

In Column 82, Claim 2, lines 55 through 65, delete:

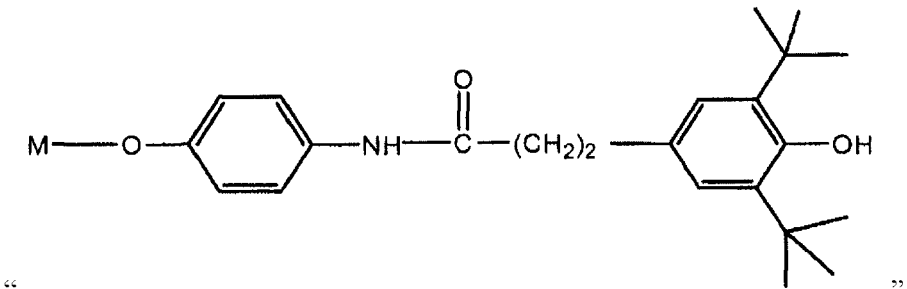

" "

and insert:

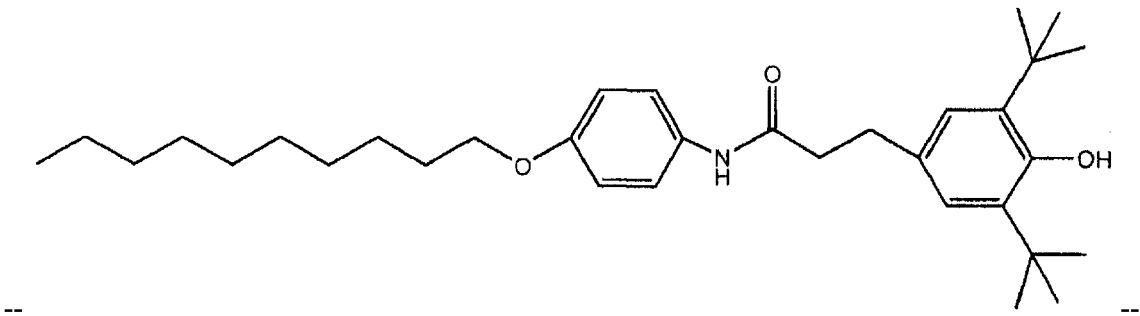

-- --

Signed and Sealed this

Fifteenth Day of June, 2010

David J. Kappos  
*Director of the United States Patent and Trademark Office*